United States Patent
Nishi et al.

Patent Number: 5,876,713
Date of Patent: Mar. 2, 1999

[54] GLUTAMINE: FRUCTOSE-6-PHOSPHATE AMIDOTRANSFERASE, ITS PRODUCTION AND USE

[76] Inventors: Kazunori Nishi, 16-1-402 Namiki 4-chome; Yukiko Hikichi, 21-2-1-504, Matsushiro 4-chome; Yasushi Shintani, 7-9-703, Kasuga 1-chome, all of Tsukuba, Ibaraki, Japan, 305

[21] Appl. No.: 911,445

[22] Filed: Aug. 12, 1997

[30] Foreign Application Priority Data

Aug. 13, 1996 [JP] Japan .................................. 8-213944

[51] Int. Cl.$^6$ .............................. C12N 9/10; A61K 38/45
[52] U.S. Cl. .......................... 424/94.5; 514/12; 435/193
[58] Field of Search .......................... 435/193; 424/94.5; 514/12

[56] References Cited

FOREIGN PATENT DOCUMENTS

WO 93/21330  10/1993  WIPO .

OTHER PUBLICATIONS

Nerlich AG, et al. Expression of glutamine:fructose–6–phosphateamidotransferase in human tissues: evidence for highly variability and distinct regulation in diabetes. Diabetes.1998 Feb.; 47(2): 470–178, Jan. 4, 1998.

Kornfeld R. Studies on L–glutamine D–fructose 6–phosphateamidotransferase. I. Feedback inhibition by uridine diphosphate–N–acetylglucosamine. J Biol Chem. 1967 Jul. 10; 242(13): 3135–3141, Jul. 10, 1967.

Chen H, et al. Effects of overexpression of glutamine:fructose–6–phosphateamidotransferase (GFAT) and glucosamine treatment on translocation of GLUT4 in rat adipose cells. Mol Cell Endocrinol. 1997 Nov. 30; 135(1): 66–77, Nov. 30, 1997.

Zhou J, et al. Human glutamine: fructose–6–phosphate amidotransferase: characterization of mRNA and Chromosomal assignment to 2p13. Hum Genet. 1995 Jul; 96(1): 99–101, Jul. 1, 1995.

Whitmore TE, et al. Physical mapping of the human glutamine:fructose–6–phosphate amidotransferase gene (GFPT) to chromosome 2p13. Genomics. 1995 Mar. 20; 26 (2): 422–423, Mar. 20, 1995.

McKnight GL, et al. Molecular cloning, cDNA sequence, and bacterial expression of human glutamine:fructose–6–phosphate amidotransferase. J Biol Chem. 1992 Dec. 15; 267(35): 25208–25212, Dec. 15, 1992.

Sayeski PP, et al. The murine glutamine:fructose–6–phosphate amidotransferase–encoding CDNA sequence. Gene 1994 Mar. 25; 140(2): 289–290. Mar. 25, 1994.

Daniels MC, et al. Glutamine:fructose–6–phosphateamidotransferase activity in cultures human skeletal muscle cells: relationship to glucose disposal rate in control and non–insulin–dependent diabetes mellitus subjects and regulation by glucose and insulin. J Clin Invest. 1996 Mar. 1; 97(5): 1235–1241, Mar. 1, 1996.

McClain DA, et al. Hexosamines and insulin resistance Diabetes. 1996 Aug; 45(8): 1003–1009. Aug. 4, 1996.

Crook ED, et al. Regulation of glycogen synthase and protein phosphatase–1 by hexosamines. Diabetes. 1996 Mar; 45(3): 322–327, Mar. 4, 1996.

Robinson KA, et al. Effects of diabetes and hyperglycemia on thehexosamine synthesis pathway in rat muscle and liver. Diabetes. 1995 Dec; 44(12): 1438–1446, Dec. 1, 1995.

Yki–Jarvinen H, et al. Increased glutamine:fructose–6–phosphateamidotransferase activity on skeletal mucsle of patients with NIDDM. Diabetes. 1996 Mar; 45(3): 302–307, Mar. 1, 1996.

Sayeski PP, et al. Glucose metabolism to glucosamine is necessary for glucose stimulation of transforming growth factor–alpha gene transcription. J Biol Chem. 1996 Jun. 21; 271(25): 15237–15243, Jun. 21, 1996.

McClain DA, et al. Hexosamines and insulin resistance. Diabetes. 1996 Aug; 45(8): 1003–1009. Aug. 4, 1996.

G. McKnight et al., The Journal of Biological Chemistry, 267(35):25208–25212 (1992).

P. Sayeski et al., Gene, 140:389–290 (1994).

*Primary Examiner*—Keith D. Hendricks
*Assistant Examiner*—Bradley S. Mayhew

[57] ABSTRACT

This invention relates to glutamine:fructose-6-phosphate amidotransferase, or its partial peptide or a salt thereof; a DNA coding for the protein; a recombinant vector; a transformant; a method for producing the protein; a pharmaceutical composition comprising the protein, its partial peptide or a salt thereof; and an antibody against the protein or its partial peptide. The protein, its partial peptide or a salt thereof, and the DNA are useful for a prophylactic or therapeutic agent for hypoglycemia. The antibody can be used in the assay of the protein, its partial peptide or a salt thereof. The protein, its partial peptide or a salt thereof is useful as a reagent for the screening for candidate medical compounds.

8 Claims, 19 Drawing Sheets

FIG. IA

```
ATGTGCGGAATCTTTGCCTACATGAACTACAGAGTCCCCC    40
MetCysGlyIlePheAlaTyrMetAsnTyrArgValProA

GGACGAGGAAGGAGATCTTCGAAACCCTCATCAAGGGCCT    80
rgThrArgLysGluIlePheGluThrLeuIleLysGlyLe

GCAGCGGCTGGAGTACAGAGGCTACGACTCGGCAGGTGTG   120
uGlnArgLeuGluTyrArgGlyTyrAspSerAlaGlyVal

GCGATCGATGGGAATAATCACGAAGTCAAAGAAAGACACA   160
AlaIleAspGlyAsnAsnHisGluValLysGluArgHisI

TTCAGCTGGTCAAGAAAAGGGGAAAGTCAAGGCTCTCGA    200
leGlnLeuValLysLysArgGlyLysValLysAlaLeuAs

TGAAGAACTTTACAAACAAGACAGCATGGACTTAAAAGTG   240
pGluGluLeuTyrLysGlnAspSerMetAspLeuLysVal

GAGTTTGAGACACACTTCGGCATTGCCCACACGCGCTGGG   280
GluPheGluThrHisPheGlyIleAlaHisThrArgTrpA

CCACCCACGGGGTCCCCAGTGCTGTCAACAGCCACCCTCA   320
laThrHisGlyValProSerAlaValAsnSerHisProGl

GCGCTCAGACAAAGGCAACGAATTTGTTGTCATCCACAAT   360
nArgSerAspLysGlyAsnGluPheValValIleHisAsn

GGGATCATCACAAATTACAAAGATCTGAGGAAATTTCTGG   400
GlyIleIleThrAsnTyrLysAspLeuArgLysPheLeuG
```

FIG. IB

```
AAAGCAAAGGCTACCAGTTTGAGTCAGAAACAGATACAGA    440
 luSerLysGlyTyrGluPheGluSerGluThrAspThrGl

GACCATCGCCAAGCTGATTAAATATGTGTTCGACAACAGA    480
 uThrIleAlaLysLeuIleLysTyrValPheAspAsnArg

GAAACTGAGGACATTACGTTTTCAACGTTGGTCGAGAGAG    520
 GluThrGluAspIleThrPheSerThrLeuValGluArgV

TCATTCAGCAGTTGGAAGGTGCATTCGCGCTGGTTTTCAA    560
 alIleGlnGlnLeuGluGlyAlaPheAlaLeuValPheLy

GAGTGTCCACTACCCAGGAGAAGCCGTTGCCACACGGAGA    600
 sSerValHisTyrProGlyGluAlaValAlaThrArgArg

GGCAGCCCCCTGCTCATCGGAGTCCGGAGCAAATACAAGC    640
 GlySerProLeuLeuIleGlyValArgSerLysTyrLysL

TCTCCACAGAACAGATCCCTATCTTATACAGGACGTGCAC    680
 euSerThrGluGlnIleProIleLeuTyrArgThrCysTh

TCTGGAGAATGTGAAGAATATCTGTAAGACACGGATGAAG    720
 rLeuGluAsnValLysAsnIleCysLysThrArgMetLys

AGGCTGGACAGCTCCGCCTGCCTCCATGCTGTGGGCGACA    760
 ArgLeuAspSerSerAlaCysLeuHisAlaValGlyAspL

AGGCCGTGGAATTCTTCTTTGCTTCTGATGCAAGCGCTAT    800
 ysAlaValGluPhePheAlaSerAspAlaSerAlaIl
```

FIG. IC

```
CATAGAGCACACCAACCGGGTCATCTTCCTGGAGGACGAT            840
 eIleGluHisThrAsnArgValIlePheLeuGluAspAsp

GACATCGCCGCAGTGGCTGATGGAAACTCTCCATTCACC             880
AspIleAlaAlaValAlaAspGlyLysLeuSerIleHisA

GGGTCAAGCGCTCGGCCAGTGATGACCCATCTCGAGCCAT            920
 rgValLysArgSerAlaSerAspAspProSerArgAlaIl

CCAGACCTTGCAGATGGAACTGCAGCAAATCATGAAAGGT            960
eGlnThrLeuGlnMetGluLeuGlnGlnIleMetLysGly

AACTTCAGTGCGTTTATGCAGAAGGAGATCTTCGAACAGC           1000
AsnPheSerAlaPheMetGlnLysGluIlePheGluGlnP

CAGAATCAGTTTTCAATACTATGAGAGGTCGGGTGAATTT           1040
 roGluSerValPheAsnThrMetArgGlyArgValAsnPh

TGAAACCAACACAGTGCTCCTGGGTGGCTTGAAGGACCAC           1080
eGluThrAsnThrValLeuLeuGlyGlyLeuLysAspHis

TTGAAGGAGATTCGACGATGCCGACGGCTCATCGTGATTG           1120
LeuLysGluIleArgArgCysArgArgLeuIleValIleG

GCTGTGGAACCAGCTACCACGCTGCCGTGGCTACGCGGCA           1160
lyCysGlyThrSerTyrHisAlaAlaValAlaThrArgGl

AGTTTTGGAGGAACTGACTGAGCTTCCTGTGATGGTTGAA           1200
nValLeuGluGluLeuThrGluLeuProValMetValGlu
```

FIG. 1D

```
CTTGCTAGTGATTTTCTGGACAGGAACACACCTGTGTTCA        1240
LeuAlaSerAspPheLeuAspArgAsnThrProValPheA

GGGATGACGTTTGCTTTTTCATCAGCCAGTCAGGCGAGAC        1280
rgAspAspValCysPhePheIleSerGlnSerGlyGluTh

CGCGGACACCCTCCTGGCGCTGCGCTACTGTAAGGACCGC        1320
rAlaAspThrLeuLeuAlaLeuArgTyrCysLysAspArg

GGCGCTCTCACCGTGGGCGTCACCAACACCGTGGGCAGCT        1360
GlyAlaLeuThrValGlyValThrAsnThrValGlySerS

CCATCTCTCGCGAGACCGACTGCGGCGTCCACATCAACGC        1400
erIleSerArgGluThrAspCysGlyValHisIleAsnAl

AGGGCCGGAGATCGGCGTGGCCAGCACCAAGGCTTATACC        1440
aGlyProGluIleGlyValAlaSerThrLysAlaTyrThr

AGTCAGTTCATCTCTCTGGTCATGTTTGGTTTGATGATGT        1480
SerGlnPheIleSerLeuValMetPheGlyLeuMetMetS

CTGAAGACCGAATTTCACTACAAAACAGGAGGCAAGAGAT        1520
erGluAspArgIleSerLeuGlnAsnArgArgGlnGluIl

CATCCGTGGCTTGAGATCTTTACCTGAGCTGATCAAGGAA        1560
eIleArgGlyLeuArgSerLeuProGluLeuIleLysGlu

GTGCTGTCTCTGGAGGAGAAGATCCACGACTTGGCCCTGG        1600
ValLeuSerLeuGluGluLysIleHisAspLeuAlaLeuG
```

FIG. IE

```
AGCTCTACACGCAGAGATCGCTGCTGGTGATGGGGCGGGG     1640
luLeuTyrThrGlnArgSerLeuLeuValMetGlyArgGl

CTACAACTATGCCACCTGCCTGGAAGGAGCCCTGAAAATT     1680
yTyrAsnTyrAlaThrCysLeuGluGlyAlaLeuLysIle

AAAGAGATAACCTACATGCACTCAGAAGGCATCCTGGCTG     1720
LysGluIleThrTyrMetHisSerGluGlyIleLeuAlaG

GGGAGCTGAAGCACGGCCCCTGGCACTGATTGACAAGCA     1760
lyGluLeuLysHisGlyProLeuAlaLeuIleAspLysGl

GATGCCCGTCATCATGGTCATTATGAAGGATCCTTGCTTC     1800
nMetProValIleMetValIleMetLysAspProCysPhe

GCCAAATGCCAGAACGCCCTGCAGCAAGTCACGGCCCGCC     1840
AlaLysCysGlnAsnAlaLeuGlnGlnValThrAlaArgG

AGGTTTGACTTCCCCAGAAATCTGGCCAAGTCTGTAACTG     1880
lnVal

TGGAATGAGGCTGAGACCGTGACAAGACCATCACCACCTT     1920
TCATCTGATTCCAGACCTGTCCAACAGCAGGGATGCTAC     1960
ATGGAAGAGAAGTGGACATCCACATGTTCTGCGTCCTC     2000
CTGTAGAGCTTGACAGCTTCCACGTGCCTTCTACCCAAGT     2040
GCTTTTCCTTACAGCAGATACTGTTTCTCTGTGTCCTGAA     2080
GTCGCCAGAGGAGAAGGCAATCATTGTTTACACATGGGA     2120
TCAGAGCAGACTTCTCCACTACTGTCCAATAGAGATACAG     2160
CTCTCTTCAGAGTAACTGTGAACCTTTTATAACCAACACT     2200
```

FIG. IF

```
AGAGTTAGTTTTAAAAGACAAGATATTTATAATGACGACT   2240
GTATAGCTTTTAAGTTATTTTTCTAGTATGTGGCTTTCTG   2280
TAGCCGTGGTAACGGCCAAACTGTTCATCCTAGCTACCCA   2320
TGCTCTGTGTCCAGGCTTGCTCCTGGCAGGTGGCATTCAT   2360
CTCAGATGTGAGCACAAGGCATTGGCCCTCTGGACTCCTT   2400
TCTCCTTTTCTTTCCTCTCTAGGCTGCTCCTGAATCCTGT   2440
TCTCTGACATCCGTGGAGCCCCTCCTGCATCCACCTATGC   2480
CTCCTATAAGTCCAGTTGAAATCTCAGCCTCCTTCAACAT   2520
TTTCTTCTCGTGTGTGGCCCACATCCCTCCACTTCTCCAA   2560
CTTCTGTTTAATCTGATCACGGCTCTTTTTAAGCCCTGGC   2600
AGCATTTGGTCCCTGCTCCTTGCCCATAGTAAAACAGCT   2640
TGAAATATCCATGCAAGAGAGTAGTTTCAAGTGGGCAAC   2680
TCTGCTCTCTATTTAAAAGCGTGCACAATCAAAAGTACTA   2720
TGCAATTTTAGGACAATAAGAACATACAGTTTTAAAAAA   2760
AAAAAAAAAAGG   2773
```

FIG. 2A

```
ACGATGTGCGGAATCTTTGCCTACATGAACTACAGAGTCC    40
  MetCysGlyIlePheAlaTyrMetAsnTyrArgValP

CCCGGACGAGGAAGGAGATCTTCGAAACCCTCATCAAGGG    80
 roArgThrArgLysGluIlePheGluThrLeuIleLysGl

CCTGCAGCGGCTGGAGTACAGAGGCTACGACTCGGCAGGT   120
 yLeuGlnArgLeuGluTyrArgGlyTyrAspSerAlaGly

GTGGCGATCGATGGAATAATCACGAAGTCAAAGAAAGAC    160
 ValAlaIleAspGlyAsnAsnHisGluValLysGluArgH

ACATTCAGCTGGTCAAGAAAAGGGGGAAAGTCAAGGCTCT   200
 isIleGlnLeuValLysLysArgGlyLysValLysAlaLe

CGATGAAGAACTTTACAAACAAGACAGCATGGACTTAAAA   240
 uAspGluGluLeuTyrLysGlnAspSerMetAspLeuLys

GTGGAGTTTGAGACACACTTCGGCATTGCCCACACGCGCT   280
 ValGluPheGluThrHisPheGlyIleAlaHisThrArgT

GGGCCACCCACGGGGTCCCCAGTGCTGTCAACAGCCACCC   320
 rpAlaThrHisGlyValProSerAlaValAsnSerHisPr

TCAGCGCTCAGACAAAGGCAACGAATTTGTTGTCATCCAC   360
 oGlnArgSerAspLysGlyAsnGluPheValValIleHis

AATGGGATCATCACAAATTACAAAGATCTGAGGAAATTTC   400
 AsnGlyIleIleThrAsnTyrLysAspLeuArgLysPheL
```

FIG. 2B

```
TGGAAAGCAAAGGCTACGAGTTTGAGTCAGAAACAGATAC   440
euGluSerLysGlyTyrGluPheGluSerGluThrAspTh

AGAGACCATCGCCAAGCTGATTAAATATGTGTTCGACAAC   480
rGluThrIleAlaLysLeuIleLysTyrValPheAspAsn

AGAGAAACTGAGGACATTACGTTTTCAACGTTGGTCGAGA   520
ArgGluThrGluAspIleThrPheSerThrLeuValGluA

GAGTCATTCAGCAGTTGGAAGGTGCATTCGCGCTGGTTTT   560
rgValIleGlnGlnLeuGluGlyAlaPheAlaLeuValPh

CAAGAGTGTCCACTACCCAGGAGAAGCCGTTGCCACACGG   600
eLysSerValHisTyrProGlyGluAlaValAlaThrArg

AGAGGCAGCCCCCTGCTCATCGGAGTCCGGAGCAAATACA   640
ArgGlySerProLeuLeuIleGlyValArgSerLysTyrL

AGCTCTCCACAGAACAGATCCCTATCTTATACAGGACGTG   680
ysLeuSerThrGluGlnIleProIleLeuTyrArgThrCy

CACTCTGGAGAATGTGAAGAATATCTGTAAGACACGGATG   720
sThrLeuGluAsnValLysAsnIleCysLysThrArgMet

AAGAGGCTGGACAGCTCCGCCTGCCTGCATGCTGTGGGCG   760
LysArgLeuAspSerSerAlaCysLeuHisAlaValGlyA

ACAAGGCCGTGGAATTCTTCTTTGCTTCTGATGCAAGCGC   800
spLysAlaValGluPhePhePheAlaSerAspAlaSerAl
```

FIG. 2C

```
TATCATAGAGCACACCAACCGGGTCATCTTCCTGGAGGAC    840
aIleIleGluHisThrAsnArgValIlePheLeuGluAsp

GATGACATCGCCGCAGTGGCTGATGGAAACTCTCCATTC     880
AspAspIleAlaAlaValAlaAspGlyLysLeuSerIleH

ACCGGGTCAAGCGCTCGGCCAGTGATGACCCATCTCGAGC    920
isArgValLysArgSerAlaSerAspAspProSerArgAl

CATCCAGACCTTGCAGATGGAACTGCAGCAAATCATGAAA    960
aIleGlnThrLeuGlnMetGluLeuGlnGlnIleMetLys

GGTAACTTCAGTGCGTTTATGCAGAAGGAGATCTTCGAAC    1000
GlyAsnPheSerAlaPheMetGlnLysGluIlePheGluG

AGCCAGAATCAGTTTTCAATACTATGAGAGGTCGGGTGAA    1040
lnProGluSerValPheAsnThrMetArgGlyArgValAs

TTTTGAAACCAACACAGTGCTCCTCGGTGGCTTGAAGGAC    1080
nPheGluThrAsnThrValLeuLeuGlyGlyLeuLysAsp

CACTTGAAGGAGATTCGACGATGCCGACGGCTCATCGTGA    1120
HisLeuLysGluIleArgArgCysArgArgLeuIleValI

TTGGCTGTGGAACCAGCTACCACGCTGCCGTGGCTACGCG    1160
leGlyCysGlyThrSerTyrHisAlaAlaValAlaThrAr

GCAAGTTTTGGAGGAACTGACTGAGCTTCCTGTGATGGTT    1200
gGlnValLeuGluGluLeuThrGluLeuProValMetVal
```

FIG. 2D

```
GAACTTGCTAGTGATTTTCTGGACAGGAACACACCTGTGT    1240
GluLeuAlaSerAspPheLeuAspArgAsnThrProValP

TCAGGGATGACGTTTGCTTTTTCATCAGCCAGTCAGGCGA    1280
heArgAspAspValCysPhePheIleSerGlnSerGlyGl

GACCGCGGACACCCTCCTGGCGCTGCGCTACTGTAAGGAC    1320
uThrAlaAspThrLeuLeuAlaLeuArgTyrCysLysAsp

CGCGGCGCTCTCACCGTCGGCGTCACCAACACCGTGGGCA    1360
ArgGlyAlaLeuThrValGlyValThrAsnThrValGlyS

GCTCCATCTCTCGCGAGACCGACTGCGGCGTCCACATCAA    1400
erSerIleSerArgGluThrAspCysGlyValHisIleAs

CGCAGGGCCGGAGATCGGCGTGGCCAGCACCAAGGCTTAT    1440
nAlaGlyProGluIleGlyValAlaSerThrLysAlaTyr

ACCAGTCAGTTCATCTCTCTGGTCATGTTTGGTTTGATGA    1480
ThrSerGlnPheIleSerLeuValMetPheGlyLeuMetM

TGTCTGAAGACCGAATTTCACTACAAACAGGAGGCAAGA    1520
etSerGluAspArgIleSerLeuGlnAsnArgArgGlnGl

GATCATCCGTGGCTTGAGATCTTTACCTGAGCTGATCAAG    1560
uIleIleArgGlyLeuArgSerLeuProGluLeuIleLys

GAAGTCCTGTCTCTGGAGGAGAAGATCCACGACTTGGCCC    1600
GluValLeuSerLeuGluGluLysIleHisAspLeuAlaL
```

FIG. 2E

```
TGGAGCTCTACACGCAGAGATCGCTGCTGGTCATGGGGCG   1640
euGluLeuTyrThrGlnArgSerLeuLeuValMetGlyAr

GGGCTACAACTATGCCACCTGCCTGGAAGGAGCCCTGAAA   1680
gGlyTyrAsnTyrAlaThrCysLeuGluGlyAlaLeuLys

ATTAAAGAGATAACCTACATGCACTCAGAAGGCATCCTGG   1720
IleLysGluIleThrTyrMetHisSerGluGlyIleLeuA

CTGGGGAGCTGAAGCACGGGCCCCTGGCACTGATTGACAA   1760
laGlyGluLeuLysHisGlyProLeuAlaLeuIleAspLy

GCAGATGCCCGTCATCATGGTCATTATGAAGGATCCTTGC   1800
sGlnMetProValIleMetValIleMetLysAspProCys

TTCGCCAAATGCCAGAACGCCCTGCAGCAAGTCACGGCCC   1840
PheAlaLysCysGlnAsnAlaLeuGlnGlnValThrAlaA

GCCAGGGTCGCCCCATTATACTGTGCTCCAAGGACGATAC   1880
rgGlnGlyArgProIleIleLeuCysSerLysAspAspTh

TGAAAGTTCCAAGTTTGCGTATAAGACAATTGAGCTGCCC   1920
rGluSerSerLysPheAlaTyrLysThrIleGluLeuPro

CACACTGTGGACTGCCTCCAGGGCATCCTGAGCGTGATTC   1960
HisThrValAspCysLeuGlnGlyIleLeuSerValIleP

CGCTGCAGCTGCTGTCCTTCCACCTGGCTGTTCTCCGAGG   2000
roLeuGlnLeuLeuSerPheHisLeuAlaValLeuArgGl
```

FIG. 2F

ATATGACGTTGACTTCCCCAGAAATCTGGCCAAGTCTGTA 2040
yTyrAspValAspPheProArgAsnLeuAlaLysSerVal

ACTGTGGAATGAGGCTGAGACCGTGACA 2068
ThrValGlu

FIG. 3A

| | |
|---|---|
| ATGTGCGGAATCTTTGCCTACATGAACTACAGAGTCCCCC<br>MetCysGlyIlePheAlaTyrMetAsnTyrArgValProA | 40 |
| GGACGAGGAAGGAGATCTTCGAAACCCTCATCAAGGGCCT<br>rgThrArgLysGluIlePheGluThrLeuIleLysGlyLe | 80 |
| GCAGCGGCTGGAGTACAGAGGCTACGACTCGGCAGGTGTG<br>uGlnArgLeuGluTyrArgGlyTyrAspSerAlaGlyVal | 120 |
| GCGATCGATGGAATAATCACGAAGTCAAAGAAAGACACA<br>AlaIleAspGlyAsnAsnHisGluValLysGluArgHisI | 160 |
| TTCAGCTGGTCAAGAAAAGGGGAAAGTCAAGGCTCTCGA<br>leGlnLeuValLysLysArgGlyLysValLysAlaLeuAs | 200 |
| TGAAGAACTTTACAAACAAGACAGCATGGACTTAAAAGTG<br>pGluGluLeuTyrLysGlnAspSerMetAspLeuLysVal | 240 |
| GAGTTTGAGACACACTTCGGCATTGCCCACACGCGCTGGG<br>GluPheGluThrHisPheGlyIleAlaHisThrArgTrpA | 280 |
| CCACCCACGGGGTCCCCAGTGCTGTCAACAGCCACCCTCA<br>laThrHisGlyValProSerAlaValAsnSerHisProGl | 320 |
| GCGCTCAGACAAAGGCAACGAATTTGTTGTCATCCACAAT<br>nArgSerAspLysGlyAsnGluPheValValIleHisAsn | 360 |
| GGGATCATCACAAATTACAAGATCTGAGGAAATTTCTGG<br>GlyIleIleThrAsnTyrLysAspLeuArgLysPheLeuG | 400 |

FIG. 3B

```
AAAGCAAAGGCTACgATTTTGAGTCAGAAACAGATACAGA      440
luSerLysGlyTyrAspPheGluSerGluThrAspThrGl

GACCATCGCCAAGCTGATTAAATATGTGTTCGACAACAGA      480
uThrIleAlaLysLeuIleLysTyrValPheAspAsnArg

GAAACTGAGGACATTACGTTTTCAACGTTGGTCGAGAGAG      520
GluThrGluAspIleThrPheSerThrLeuValGluArgV

TCATTCAGCAGTTGGAAGGTGCATTCGCGCTGGTTTTCAA      560
alIleGlnGlnLeuGluGlyAlaPheAlaLeuValPheLy

GAGTGTCCACTACCCAGGAGAAGCCGTTGCCACACGGAGA      600
sSerValHisTyrProGlyGluAlaValAlaThrArgArg

GGCAGCCCCCTGCTCATCGGAGTCCGGAGCAAATACAAGC      640
GlySerProLeuLeuIleGlyValArgSerLysTyrLysL

TCTCCACAGAACAGATCCCTATCTTATACAGGACGTGCAC      680
euSerThrGluGlnIleProIleLeuTyrArgThrCysTh

TCTGGAGAATGTGAAGAATATCTGTAAgACACGGATGAAG      720
rLeuGluAsnValLysAsnIleCysLysThrArgMetLys

AGGCTGGACAGCTCCGCCTGCCTGCATGCTGTGGGCGACA      760
ArgLeuAspSerSerAlaCysLeuHisAlaValGlyAspL

AGGTCGTGGAATTCTTCTTTGCTTCTGATGCAAGCGCTAT      800
ysValValGluPhePhePheAlaSerAspAlaSerAlaIl
```

FIG. 3C

```
CATAGAGCACACCAACCGGGTCATCTTCCTGGAGGACGAT    840
 eIleGluHisThrAsnArgValIlePheLeuGluAspAsp

GACATCGCCGCAGTGGCTGATGGAAACTCTCCATTCACC    880
 AspIleAlaAlaValAlaAspGlyLysLeuSerIleHisA

GGGTCAAGCGCTCGGCCAGTGATGACCCATCTCGAGCCAT    920
 rgValLysArgSerAlaSerAspAspProSerArgAlaIl

CCAGACCTTGCAGATGGAACTGCAGCAAATCATGAAAGGT    960
 eGlnThrLeuGlnMetGluLeuGlnGlnIleMetLysGly

AACTTCAGTGCGTTTATGCAGAAGGAGATCTTCGAACAGC   1000
 AsnPheSerAlaPheMetGlnLysGluIlePheGluGlnP

CAGAATCAGTTTTCAATACTATGAGAGGTCGGGTGAATTT   1040
 roGluSerValPheAsnThrMetArgGlyArgValAsnPh

TGAAACCAACACAGTGCTCCTCGGTGGCTTGAAGGACCAC   1080
 eGluThrAsnThrValLeuLeuGlyGlyLeuLysAspHis

TTGAAGGAGATTCGACGATGCCGACGGCTCATCGTGATTG   1120
 LeuLysGluIleArgArgCysArgArgLeuIleValIleG

GCTGTGGAACCAGCTACCACGCTGCCGTGGCTACGCGGCA   1160
 lyCysGlyThrSerTyrHisAlaAlaValAlaThrArgGl

AGTTTTGGAGGAACTGACTGAGCTTCCTGTGATGGTTGAA   1200
 nValLeuGluGluLeuThrGluLeuProValMetValGlu
```

FIG. 3D

```
CTTGCTAGTGATTTTCTGGACAGGAACACACCTGTGTTCA    1240
LeuAlaSerAspPheLeuAspArgAsnThrProValPheA

GGGATGACGTTTGCTTTTTCATCAGCCAGTCAGGTAAGGG    1280
rgAspAspValCysPhePheIleSerGlnSerGlyLysGl

ACACAGGCATTGTGGCCAGCCTTGCATCAGGTCAGCTCTG    1320
yHisArgHisCysGlyGlnProCysIleArgSerAlaLeu

GGCTCTCTCCTCTTCTCCTTCATTCAGTTAAGTCCTCTGC    1360
GlySerLeuLeuPheSerPheIleGlnLeuSerProLeuH

ATGGCTACCCTGTGCTGCGAACCCTCTCTTGCAGCGGTCA    1400
isGlyTyrProValLeuArgThrLeuSerCysSerGlyHi

TTTAACCCGTAGAGCCATGGATTACTGTCGCCATTGTACG    1440
sLeuThrArgArgAlaMetAspTyrCysArgHisCysThr

GGGAGGGCAAGAGATGTCTAA    1461
GlyArgAlaArgAspVal
```

GLUTAMINE: FRUCTOSE-6-PHOSPHATE AMIDOTRANSFERASE, ITS PRODUCTION AND USE

TECHNICAL FIELD

The present invention relates to a novel protein showing an activity of glutamine:fructose-6-phosphate amidotransferase (hereinafter briefly referred to as GFAT), etc. and to a DNA coding for the protein.

BACKGROUND ART

In recent years, the diabetic population has increased steadily and diabetes is attracting attention as one of adult diseases. Non-insulin-dependent diabetes mellitus (NIDDM) is a type of diabetes frequently found in Japan and its early detection and timely treatment are necessary to prevent the disease. Although the factors causative of NIDDM have not been fully elucidated, recent advances have provided important new insights into this process.

It is now well established that abnormalities in insulin sensitive mechanisms and reduced secretion of insulin are causes of insufficient insulin activity in NIDDM. In Europe and America, insulin resistance is predominant in patients with NIDDM while, in Japan, insulin hyposecretion is often the major cause. With recent advances in molecular biology, the cellular and molecular mechanisms underlying insulin resistance such as the insulin receptor structure and the mechanism of signal transduction downstream of the receptor, have been investigated in detail. During the last decade, glucose transporter genes has been cloned and the relationship between mutations in the genes and the process of diabetes has been studied. However, the insulin, glucokinase and mitochondrial gene abnormalities so far elucidated, taken together, account for not more than 1% of NIDDM cases. Other gene abnormalities are to be revealed in the future.

In recent years, antidiabetic agents quite differing from the conventional oral hypoglycemic agents in the mechanism of action, such as the α-glycosidase inhibitors acarbose and voglibose (Diabetes Frontier, 3, 557–564 (1992); Drugs, 46, 1025–1054 (1994); Igaku no Ayumi, 149, 591–618 (1989); Rinsho to Kenkyu (Japan. J. Clinics Exper. Med.), 67, 219–233 (1990); Rinsho to Kenkyu, 69, 919–932 (1992); Rinshoi (Clinical Medicine), 21 (supplement), 578–587 (1995)) and the insulin resistance improving agents, troglitazone and pioglitazone, (Diabetes, 37, 1549–1558 (1998); Rinsho Iyaku, 9 (supplement 3), 127–150 (1993); New Engl. J. Med., 331, 1188–1193 (1994); "Atarashii Tonyobyo Chiryoyaku (New Antidiabetics)" (edited by Yoshio Goto), published by Iyaku Journal Co., Osaka, (1994)) have been developed. They are expected to be soon on the market.

Meanwhile, in the United States, a biguanide derivative was approved in 1996 as an antidiabetic for general prescription (New Engl. J. Med., 333, 541–549 (1995); Diabetes Spectrum, 8, 194–197 (1995)) and is attracting attention. The above-mentioned drugs, unlike sulfonylureas (SUs) which have been used for many years in routine medical care, produce a hypoglycemic effect without promoting insulin secretion from β cells of the pancreas.

It is considered, at present, that there are nine mechanisms through which antidiabetics might be able to improve insulin resistance as follows: (1) activation of insulin receptor kinase, (2) promotion of translocation of glucose transporters, (3) correction of the action of the rate-limiting enzyme involved in glucose metabolism and correction of abnormalities in glucose metabolism, (4) inhibition of gluconeogenesis in liver, (5) promotion of glucose uptake by liver, (6) enhancement of glycogenesis in liver, (7) reduction in blood lipid level, (8) decrease in gluconeogenesis in liver as resulting from the reduction in blood lipid level, and (9) enhancement of insulin sensitivity as resulting from the reduction in blood lipid level.

GFAT is an important enzyme catalyzing the conversion of fructose-6-phosphate to glucosamine-6-phosphate, which is the rate-limiting step in the hexosamine biosynthesis pathway. Inhibitors of GFAT activity are thought to promote glucose influx by cells and thereby reducing the blood glucose level. Therefore, these inhibitors are expected to be of use as antidiabetics. Their mechanism of action is thought to be associated with the process (2) or (5) mentioned above.

While the hexosamine biosynthesis pathway metabolizes glucosamine-6-phosphate to UDP-N-acetylglucosamine, CMP-N-acetylneuraminic acid, etc., those metabolic intermediates are thought to be utilized as precursors for glycosylation of proteins or as essential substrates for the synthesis of proteoglycan and ganglioside.

Insulin activates its signal transduction pathway through binding insulin receptor and translocates glucose transporters (GLUT4 etc.) pooled within cells to the cell membrane resulting in increasing glucose influx. Glucose is metabolized by glycolysis pathway and ATP is accumulated as an energy source. When the influx of glucose is excessive, however, fructose-6-phosphate enters the hexosamine biosynthesis pathway and is converted to glucosamine-6-phosphate catalyzed by GFAT. Although detailed mechanisms remain unknown, several observations indicate that metabolites of glucosamine-6-phosphate prevent glucose transporters from translocating to cell membrane, resulting in reducing cellular glucose influx (FASEB J., 5, 3031–3036 (1991); Diabetologia, 38, 518–524 (1995); J. Biol. Chem., 266, 10115–10161 (1991): J. Biol. Chem., 266, 4706–4712 (1991); Endocrinology, 136, 2809–2816 (1995)).

Therefore, the hexosamine biosynthesis pathway is considered to control the influx of glucose by a feedback manner. GFAT is the rate-limiting enzyme in this pathway. GFAT activity is also known to be generally high in patients with NIDDM and is considered to be one of the causes of high blood glucose levels (Diabetes, 45, 302–307 (1996)).

Hypoglycemic agents, such as inhibitors of GFAT activity, whose action is mainly directed to some other tissues than pancreas invariably improve insulin resistance in target tissues. These agents have some clinical merits in addition to their hypoglycemic activity, because of their secondary effects. When used in combination with other drugs, they are highly effective and have very bright prospects before them.

Recently a human GFAT gene has been cloned (J. Biol. Chem., 267, 25208–25212 (1992)). The gene product is a 77 kDa protein composed of 681 amino acid residues. GFAT genes have been cloned from other animal species as well. For example, a murine GFAT is highly homologous to the human GFAT (91% at the nucleotide level and 98.6% at the amino acid level), hence it is considered to be the counterpart of the human GFAT (Gene, 140, 289–290 (1994)). In addition, a yeast GFAT (J. Biol. Chem., 264, 8753–8758 (1989)) and a *Escherichia coli*-derived GFAT (Biochem. J., 224, 779–815 (1984)) have also been reported, each having high homology with the human GFAT. It is not known about the occurrence of a new GFAT isoform gene.

Isolation of a novel protein showing GFAT activity, if successful, would make it possible to perform further investigations to elucidate the regulatory function of GFAT in the hexosamine biosynthesis pathway and, if its expression is tissue-specific, to elucidate the tissue-specific mechanisms of glucose metabolism. A specific inhibitor of the novel GFAT protein, if developed, would make it possible to develop a hypoglycemic agent acting through novel mechanisms of action and contributing to the prevention and treatment of diabetes and diabetic complications without producing serious adverse effects.

As the result of intensive research, the inventors of the present invention succeeded in cloning a cDNA having a novel nucleotide sequence from a human brain-derived cDNA library and found that the protein encoded thereby has GFAT activity. As the result of continued investigations based on such findings, the present inventors have now completed the present invention.

Disclosure of Invention

The present invention provides:

(1) A protein comprising an amino acid sequence represented by SEQ ID NO:1 or a substantial equivalent thereto, or a salt thereof;

(2) The protein according to (1), which has an amino acid sequence represented by SEQ ID NO:2 or SEQ ID NO:3, or a substantial equivalent thereto;

(3) The protein according to (1) or (2), which shows an activity of glutamine:fructose-6-phosphate amidotransferase;

(4) A partial peptide of the protein according to (1), or a salt thereof;

(5) An isolated DNA comprising a DNA having a nucleotide sequence coding for the protein according to (1) or the partial peptide according to (4);

(6) The DNA according to (5), which has a nucleotide sequence represented by SEQ ID NO:4;

(7) The DNA according to (5), which has a nucleotide sequence represented by SEQ ID NO:5 or SEQ ID NO:6;

(8) A recombinant vector comprising the DNA according to (5);

(9) A transformant which is transformed with the recombinant vector according to (8);

(10) A method of producing the protein or a salt thereof according to (1), which comprises culturing the transformant according to (9) under conditions suitable to express and accumulate the protein or a salt thereof according to (1) and collect the same;

(11) A pharmaceutical composition comprising the protein according to (1), the partial peptide according to (4) or a salt thereof;

(12) The pharmaceutical composition according to (11), which is a therapeutic or prophylactic agent for hypoglycemia;

(13) A pharmaceutical composition which comprises the DNA according to (5);

(14) The pharmaceutical composition according to (13), which is a therapeutic or prophylactic agent for hypoglycemia;

(15) An antibody against the protein according to (1), the partial peptide according to (4) or a salt thereof;

(16) A method for screening for a compound, or a salt thereof, which inhibits an enzyme activity of the protein or a salt thereof according to (1), which comprises measuring and comparing the enzyme activity of the protein according to (1), the partial peptide according to (4) or a salt thereof, in cases of (i) a substrate is contacted with the protein according to (1), the partial peptide according to (4) or a salt thereof and (ii) the substrate and a test compound are contacted with the protein according to (1), the partial peptide according to (4) or a salt thereof;

(17) A kit for screening for a compound, or a salt thereof, which inhibits an enzyme activity of the protein or a salt thereof according to (1), which comprises the protein according to (1), the partial peptide according to (4) or a salt thereof;

(18) A compound, or a salt thereof, which inhibits an enzyme activity of the protein or a salt thereof according to (1), which is identified by the screening method according to (16) or the screening kit according to (17);

(19) A pharmaceutical composition which comprises a compound, or a salt thereof, which inhibits an enzyme activity of the protein or a salt thereof according to (1), which is identified by the screening method according to (16) or the screening kit according to (17);

(20) The pharmaceutical composition according to (19), which is a therapeutic or prophylactic agent for diabetes;

(21) A method for treating or preventing hypoglycemia in human or a mammal which comprises administering an effective amount of the protein according to (1), the partial peptide according to (4) or a salt thereof to human or a mammal;

(22) A method for treating or preventing hypoglycemia in human or a mammal which comprises administering an effective amount of the DNA according to (5) to human or a mammal;

(23) Use of the protein according to (1), the partial peptide according to (4) or a salt thereof for production of a therapeutic or prophylactic agent for hypoglycemia;

(24) Use of the DNA according to (5) for production of a therapeutic or prophylactic agent for hypoglycemia;

Moreover the present invention provides:

(25) A partial peptide according to (4) which has an amino acid sequence represented by SEQ ID NO:7, SEQ ID NO:8 or SEQ ID NO:9, or an amino acid sequence substantially equivalent thereto;

(26) A DNA comprising a DNA having a nucleotide sequence capable of hybridizing under high stringent condition with the nucleotide sequence of SEQ ID NO:5 or SEQ ID NO: 6.

(27) A recombinant vector comprising the DNA according to (26);

(28) A transformant which is transformed with the vector according to (27);

(29) A method of producing a protein, or a salt thereof, which is encoded by the DNA according to (26), which comprises culturing the transformant according to

(28) under conditions suitable to express and accumulate the protein or a salt thereof and collect the same;

(30) A protein encoded by the DNA according to (26), or a salt thereof which is produced by the method according to (29);

(31) A method of quantitative determination of the protein according to (1), the partial peptide according to (4) or a salt thereof in a test liquid sample, which comprises
  (a) competitively reacting the test liquid sample and a labeled protein according to (1), partial peptide according to (4) or a salt thereof with the antibody according to (15), and (b) measuring the ratio of the labeled protein according to (1), partial peptide according to (4) or a salt thereof which binds to the antibody;

(32) A method of quantitative determination of the protein according to (1), the partial peptide according to (4) or a salt thereof in a test liquid sample, which comprises (a) reacting the test liquid sample with the antibody according to (15) immobilized on an insoluble carrier and a labeled antibody according to (15) simultaneously or continuously, and (b) measuring the activity of the labeling agent on the insoluble carrier;

(33) A pharmaceutical composition which comprises the antibody according to (15) (preferably, the antibody according to (15) which shows an activity to neutralize the activity of the protein according to (1));

(34) The pharmaceutical composition according to (33) which is a therapeutic or prophylactic agent for diabetes;

(35) An antisense DNA which has a nucleotide sequence complementary or substantially complementary to the DNA according to (5) or (26) and capable of suppressing expression of the DNA;

(36) An antisense DNA according to (35), wherein the nucleotide sequence substantially complementary to the DNA according to (5) or (26) is a nucleotide sequence having an identity of not less than about 70% (preferably not less than about 80%, more preferably not less than about 90%, most preferably not less than about 95%) to the total nucleotide sequence or part of the nucleotide sequence of the nucleotide sequence complementary to the DNA according to (5) or (26);

(37) A pharmaceutical composition which comprises the antisense DNA according to (35); and

(38) A pharmaceutical composition according to (37) which is a therapeutic or prophylactic agent for diabetes.

The protein of the present invention has an amino acid sequence represented by SEQ ID NO:1 (a 1st to 425th amino acid sequence of the amino acid sequence represented by SEQ ID NO:2 or FIGS. 1A–1F, or a 1st to 425th amino acid sequence of the amino acid sequence represented by SEQ ID NO:3 or FIGS. 2A–2F), or a substantially equivalent thereto.

The protein of the present invention may be a protein derived from cells of any kind (e.g. splenocytes, neurons, glia cells, splenic β cells, myelocytes, mesangial cells, Langerhan's cells, epidermal cells, epithelial cells, endothelial cells, fibroblasts, fibrous cells, muscle cells, fat cells, immune cells (e.g. macrophages, T cells, B cells, natural killer cells, mast cells, neutrophils, basophils, eosinophils, monocytes), megarkaryocytes, synovial cells, chondrocytes, osteocytes, osteoblasts, osteoclasts, mammary cells, hepatocytes, interstitial cells, progenitor cells of said cells, stem cells, cancer cells, etc.) of human or other warm-blooded animals (e.g. guinea pig, rat, mouse, chicken, rabbit, swine, sheep, bovine, equine, monkey, etc.) and all tissues in which such cells are present, such as brain, various parts of brain (e.g. olfactory bulb, amygdaloid nucleus, cerebral basal nucleus, hippocampus, thalamus, hypothalamus, cerebral cortex, medulla oblongata, cerebellum), spinal cord, pituitary gland, stomach, spleen, kidney, liver, gonad, thyroid, gall-bladder, bone marrow, adrenal gland, skin, muscle, lung, gastrointestinal tract (e.g. large intestine, small intestine), blood vessels, heart, thymus, spleen, submandibular gland, peripheral blood, prostate, testis, ovary, placenta, uterus, bone, joint, skeletal muscle, etc. It may be a synthetic protein as well.

Examples of the amino acid sequence which is substantial equivalent to the amino acid sequence represented by SEQ ID NO:1 are an amino acid sequence which is not less than about 80%, preferably not less than about 85%, more preferably not less than about 90%, still more preferably not less than about 95% identity to the amino acid sequence represented by SEQ ID NO:1, and so on.

Examples of the protein of the present invention which comprises an amino acid sequence substantial equivalent to the amino acid sequence represented by SEQ ID NO:1 are a protein having an amino acid sequence substantial equivalent to the amino acid sequence represented by SEQ ID NO:1 and having a qualitatively equivalent activity to the protein having the amino acid sequence represented by SEQ ID NO:1.

Examples of the substantial equivalent activity are a GFAT activity, etc.

The term "qualitatively equivalent activity" means that the nature of these activities are physiologically chemically or pharmacologically equivalent. The term "substantially equivalent" means the nature of these activities are physiologically, chemically, or pharmacologically equivalent. Therefore, it is preferred that the potency of activities such as a GFAT activity is equivalent (e.g. about 0.01 to 100 times, preferably about 0.5 to 20 times, more preferably about 0.5 to 2 times), and it is allowable that even differences among grades such as the potency of these activities and molecular weight of the protein are present.

GFAT activity may be measured by per se known method or its analogue method. For example, GFAT activity may be measured in accordance with the method for screening for a candidate compound as mentioned below.

And, the protein of the present invention includes, for example, proteins comprising (1) an amino acid sequence wherein one or more amino acid residues (for example 1 to 30, preferably 1 to 20, more preferably about 1 to 10, and still more preferably a few (1 to 5) amino acid residues) are deleted from the amino acid sequence represented by SEQ ID NO:1, (2) an amino acid sequence wherein one or more amino acid residues (for example, 1 to 30, preferably about 1 to 20, more preferably about 1 to 10, and still more. preferably a few (1 to 5) amino acid residues) are added to the amino acid sequence represented by SEQ ID NO:1, (3) an amino acid sequence wherein one or more other amino acid residues in the amino acid sequence represented by SEQ ID NO:1 are substituted with one or more amino acid residues (for example 1 to 30, preferably about 1 to 20, more preferably about 1 to 10, and still more preferably a few (1 to 5) amino acid residues), or (4) combinations thereof.

Preferable examples of proteins comprising the amino acid sequence substantially equivalent to the amino acid sequence represented by SEQ ID NO:1 are a protein comprising the amino acid sequence substantially equivalent to the amino acid sequence represented by SEQ ID NO:2 (FIGS. 1A–1F), a protein comprising the amino acid sequence substantially equivalent to the amino acid sequence represented by SEQ ID NO:3 (FIGS. 2A–2F), and so on.

Examples of the amino acid sequence which is substantially equivalent to the amino acid sequence represented by SEQ ID NO:2 are an amino acid sequence which is not less than about 80%, preferably not less than about 85%, more preferably not less than about 90%, still more preferably not less than 95% identity to the amino acid sequence represented by or SEQ ID NO:2, and so on. Particularly preferable examples are an amino acid sequences which has the amino acid sequence represented by SEQ ID NO:1 and has an identity of not less than about 80%, preferably not less than about 85%, more preferably not less than about 90%, and still more preferably not less than about 95% to the amino acid sequence represented by SEQ ID NO:2.

Examples of the protein of the present invention which comprises an amino acid sequence substantial equivalent to the amino acid sequence represented by SEQ ID NO:2 are a protein having an amino acid sequence substantial equivalent to the amino acid sequence represented by SEQ ID NO:2 and having a qualitatively equivalent activity to the protein having the amino acid sequence represented by SEQ ID NO:2.

Examples of the substantial equivalent activity are a GFAT activity, etc.

The term "qualitatively equivalent activity" means that the nature of these activities are physiologically, chemically, or pharmacologically equivalent. The term "substantially equivalent" means that the nature of these activities are physiologically, chemically, or pharmacologically equivalent. Therefore, it is preferred that the potency of activities such as a GFAT activity is equivalent (e.g. about 0.01 to 100 times, preferably about 0.5 to 20 times, more preferably about 0.5 to 2 times), and it is allowable that even differences among grades such as the potency of these activities and molecular weight of the protein are present.

GFAT activity may be measured by per se known method or its analogue method. For example, the GFAT activity may be measured in accordance with the method for screening for a candidate compound as mentioned below.

And, the protein of the present invention includes, for example, proteins comprising (1) an amino acid sequence wherein one or more amino acid residues (for example 1 to 30, preferably 1 to 20, more preferably about 1 to 10, and still more preferably a few (1 to 5) amino acid residues) are deleted from the amino acid sequence represented by SEQ ID NO:2, (2) an amino acid sequence wherein one or more amino acid residues (for example, 1 to 30, preferably about 1 to 20, more preferably about 1 to 10, and still more preferably a few (1 to 5) amino acid residues) are added to the amino acid sequence represented by SEQ ID NO:2, (3) an amino acid sequence wherein one or more other amino acid residues in the amino acid sequence represented by SEQ ID NO:2 are substituted with one or more amino acid residues (for example 1 to 30, preferably about 1 to 20, more preferably about 1 to 10, and still more preferably a few (1 to 5) amino acid residues), or (4) combinations thereof.

Examples of the amino acid sequence which is substantially equivalent to the amino acid sequence represented by SEQ ID NO:3 are an amino acid sequence which is not less than about 80%, preferably not less than about 85%, more preferably not less than about 90%, still more preferably not less than 95% identity to the amino acid sequence represented by or SEQ ID NO:3, and so on. Particularly preferable examples are an amino acid sequences which has the amino acid sequence represented by SEQ ID NO:1 and has a identity of not less than about 80%, preferably not less than about 85%, more preferably not less than about 90%, and still more preferably not less than about 95% to the amino acid sequence represented by SEQ ID NO:3.

Examples of the protein of the present invention which comprises an amino acid sequence substantial equivalent to the amino acid sequence represented by SEQ ID NO:3 are a protein having an amino acid sequence substantial equivalent to the amino acid sequence represented by SEQ ID NO:3 and having a qualitatively equivalent activity to the protein having the amino acid sequence represented by SEQ ID NO:2.

Examples of the substantial equivalent activity are a GFAT activity, etc.

The term "qualitatively equivalent activity" means that the nature of these activities are physiologically, chemically, or pharmacologically equivalent. The term "substantially equivalent" means that the nature of these activities are physiologically chemically or pharmacologically equivalent. Therefore, it is preferred that the potency of activities such as a GFAT activity is equivalent (e.g. about 0.01 to 100 times, preferably about 0.5 to 20 times, more preferably about 0.5 to 2 times), and it is allowable that even differences among grades such as the potency of these activities and molecular weight of the protein are present.

GFAT activity may be measured by per se known method or its analogue method. For example, the GFAT activity may be measured in accordance with the method for screening for a candidate compound as mentioned below.

And, the protein of the present invention includes, for example, proteins comprising (1) an amino acid sequence wherein one or more amino acid residues (for example 1 to 30, preferably 1 to 20, more preferably about 1 to 10, and still more preferably a few (1 to 5) amino acid residues) are deleted from the amino acid sequence represented by SEQ ID NO:3, (2) an amino acid sequence wherein one or more amino acid residues (for example, 1 to 30, preferably about 1 to 20, more preferably about 1 to 10, and still more preferably a few (1 to 5) amino acid residues) are added to the amino acid sequence represented by SEQ ID NO:3, (3) an amino acid sequence wherein one or more other amino acid residues in the amino acid sequence represented by SEQ ID NO:3 are substituted with one or more amino acid residues (for example 1 to 30, preferably about 1 to 20, more preferably about 1 to 10, and still more preferably a few (1 to 5) amino acid residues), or (4) combinations thereof.

In the above-mentioned deletion, addition or substitution, examples of the positions of deletion, addition or substitution are not so critical but are preferably positions other than (1) the 1st to 425th amino acid sequence of the amino acid sequence represented by SEQ ID NO:2 or SEQ ID NO:3 (that is, the amino acid sequence represented by SEQ ID NO:1).

Throughout this specification, proteins are represented in accordance with the conventions for description of peptides, that is the N-terminus (amino terminus) at left and the C-terminus (carboxyl terminus) at right. The protein of the present invention including the protein containing the amino acid sequence of SEQ ID NO:1 is usually in the carboxyl (—COOH) or carboxylate (—COO—) form at the C-terminus but may be in the amide (—CONH$_2$) or ester (—COOR) form.

R in the ester residue includes a $C_{1-6}$ alkyl group (e.g. methyl, ethyl, n-propyl, isopropyl, n-butyl, etc., a $C_{3-8}$ cycloalkyl group (e.g. cyclopentyl, cyclohexyl, etc.), a $C_{6-12}$ aryl group (e.g. phenyl, α-naphthyl, etc.), a $C_{7-14}$ aralkyl group such as a phenyl-$C_{1-2}$ alkyl group (e.g. benzyl, phenethyl, etc.) and α-naphthyl-$C_{1-2}$ alkyl, (e.g. α-naphthylmethyl, etc.), as well as pivaloyloxymethyl which is universally used for the production of esters for oral administration.

When the protein of the present invention has a carboxyl (or carboxylate) in any position other than the C-terminus, the corresponding amide or ester form is also included in the scope of the present invention. The ester mentioned just above may be any of the esters mentioned for the C-terminal carboxyl function.

Furthermore, the protein of the present invention includes (1) the protein in which the N-terminal amino acid residue has been protected with a protective group (e.g. $C_{1-6}$ acyl such as $C_{1-6}$ alkanoyl such as formyl acetyl, etc.), (2) the protein in which the N-terminal side of Glu has been cleaved in vivo to form pyroglutamic acid, (3) the protein in which the side chain of any relevant constituent amino acid (e.g. OH, SH, $NH_2$, imidazole group, indole group, guanizino group, etc.) has been protected by any protective group (e.g. $C_{1-6}$ acyl group such as $C_{1-6}$ alkanoyl such as formyl or acetyl, etc.), and (4) the complex protein such as glycoproteins available upon attachment of sugar chains.

More preferable examples of the protein of the present invention are a human-derived protein (TGC 028-3) having the amino acid sequence represented by SEQ ID NO:2 (FIGS. 1A–1F), a human-derived protein (TGC 028-4) having the amino acid sequence represented by SEQ ID NO:3 (FIGS. 2A–2F), and so on.

The partial peptide of the protein of the present invention may be any peptide of the above mentioned protein of the present invention such as peptides comprising at least not less than about 10, preferably not less than about 50, more preferably not less than about 100 amino acid residues of the amino acid sequence of the proteins of the present invention, and preferably having a GFAT activity.

Specifical examples of the partial peptide of the present invention are a peptide having (i) an amino acid sequence represented by SEQ ID NO:7 (a 1st to 149th amino acid sequence of the amino acid sequence represented by SEQ ID NO:2 or SEQ ID NO:3), (ii) an amino acid sequence represented by SEQ ID NO:8 (a 150th to 270th amino acid sequence of the amino acid sequence represented by SEQ ID NO:2 or SEQ ID NO:3) or/and (iii) an amino acid sequence represented by SEQ ID NO:9 (a 271th to 425th amino acid sequence of the amino acid sequence represented by SEQ ID NO:2 or SEQ ID NO:3) and so on. More specifical examples of the partial peptide of the present invention are a peptide having (i) a 1st to 270th amino acid sequence of the amino acid sequence represented by SEQ ID NO:1 (that is, an amino acid sequence having the amino acid sequence represented by SEQ ID NO:7 and the amino acid sequence represented by SEQ ID NO:8) or (ii) a 150th to 425th amino acid sequence of the amino acid sequence represented by SEQ ID NO:1, and so on.

The partial peptide of the present invention may include peptides such as peptide comprising (1) an amino acid sequence wherein one or more amino acid residues (for example 1 to 20, preferably 1 to 10, more preferably a few (1 to 5) amino acid residues) are deleted from the amino acid sequence represented by SEQ ID NO:7, SEQ ID NO:8 or SEQ ID NO:9, (2) an amino acid sequence wherein one or more amino acid residues (for example 1 to 20, preferable 1 to 10, more preferably a few (1 to 5) amino acid residues) are added to the amino acid sequence represented by SEQ ID NO:7, SEQ ID NO:8 or SEQ ID NO:9, (3) an amino acid sequence wherein one or more amino acid residues (for example 1 to 20, preferably 1 to 10, more preferably a few (1 to 5) amino acid residues) in the the amino acid sequence represented by SEQ ID NO:7, SEQ ID NO:8 or SEQ ID NO:9 are substituted with one or more amino acid residues (for example 1 to 20, preferably 1 to 10, more preferably a few (1 to 5) amino acid residues), or (4) combinations thereof.

The peptide of the present invention is usually in the carboxyl (—COOH) or carboxylate (—COO—) form at the C-terminus, but may instead be in the amide (—$CONH_2$) or ester (—COOR) form as same as the protein of the present invention as mentioned above.

Furthermore, the partial peptide of the present invention includes (1) the peptide in which the N-terminal amino acid residue (e.g. Met) has been protected with a protective group, (2) the peptide in which the N-terminal side of Glu has been cleaved in vivo to form pyroglutamic acid, (3) the peptide in which the side chain or any relevant constituent amino acid has been protected by any protective group, and (4) the complex peptide such as glycoproteins available upon attachment of sugar chains as same as the protein of the present invention as mentioned above.

As the partial peptide of the present invention is used as an antigen for preparation of an antibody, it does not need to have the GFAT activity.

The salts of the protein or the partial peptide of the present invention includes salts with physiologically acceptable bases (e.g. alkali metals) or acids such as organic or inorganic acids, and is preferably a physiologically acceptable acid addition salt. Examples of such salts are salts thereof with inorganic acids (e.g. hydrochloric acid, phosphoric acid, hydrobromic acid or sulfuric acid, etc.) and salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid, etc.)

The protein, its partial peptide or a salt thereof of the present invention can be produced from the tissues or cells of human or other warm-blooded animals by per se known technology for purification of proteins or peptides or, as described hereinafter, by culturing a transformant carrying a DNA encoding the protein. It can also be produced in accordance with the procedures for peptide synthesis which are described hereinafter.

When the protein of the present invention is produced from the tissues or cells of human or other warm-blooded animals, the tissues or cells of human or other warm-blood animals are homogenized and the protein, its partial peptide or a salt thereof of the present invention is extracted by an acid, etc. The protein, its partial peptide or a salt thereof can be purified and isolated from the extracted solution by a combination of chromatography such as reverse phase chromatography, ion exchange chromatography and so on.

For the synthesis of the protein of the present invention, its partial peptide or a salt thereof, or their amides form, any of commercial resins available for protein synthesis can be employed. Among such resins are chloromethyl resin, hydroxymethyl resin, benzhydrylamino resin, aminomethyl resin, 4-benzyloxybenzyl alcohol resin, 4-methylbenzhydrylamino resin, PAM resin, 4-hydroxymethyl-methylphenylacetamidomethyl resin, polyacrylamide resin, 4-(2',4'-dimethoxyphenyl-hydroxymethyl)phenoxy resin, and 4-(2',4'-dimethoxyphenyl-Fmoc-aminoethyl)phenoxy resin. Using such a resin, amino acids which may be beforehand protected at side-chain functional groups in a suitable manner can be serially condensed with the α-amino group in the order corresponding to the amino acid sequence of the objective protein or peptide by various condensation techniques which are per se known. After completion of the final condensation reaction, the protein or peptide is separated from the resin and the protective groups are removed. Then, in highly diluted solution, the intramolecular disulfide-forming reaction is carried out to provide the objective proteins, its peptides or amides thereof.

Referring to the above condensation of protected amino acids, various activating agents known to be useful for protein synthesis can be utilized, and carbodiimide reagents are especially preferred. The carbodiimide reagents include DCC, N,N'-diisopropylcarbodiimide, and N-ethyl-N'-(3-dimethylaminoprolyl)carbodiimide and so on. For activation by these reagents, the protected amino acid and a racemization inhibitor (e.g. HOBt, HOOBt, etc.) can be directly added to the resin, or the protected amino acid can be activated beforehand in the form of symmetric acid anhydride, HOBt ester or HOOBt ester and, then, added to the resin.

The solvent used for the above-mentioned activation of protected amino acids or the conjugation thereof to the resin can be optionally selected from among the solvents known to be useful for protein condensation reactions. Examples of the solvent are acid amides (e.g. N,N-dimethylformamide, N,N-dimethylacetamide, N-methylpyrrolidone, etc.), halogenated hydrocarbons (e.g. methylene chloride, chloroform, etc.), alcohols (e.g. trifluoroethanol, etc.), sulfoxides (e.g. dimethyl sulfoxide, etc.), ethers (e.g. pyridine, dioxane, tetrahydrofuran, etc.), nitriles (e.g. acetonitrile, propionitrile, etc.), esters (e.g. methyl acetate, ethyl acetate, etc.), and suitable mixtures of these solvents. The reaction temperature can be selected from the range known to be useful for protein-forming reactions, usually the range of about −20° C. to about 50° C. The activated amino acid derivative is generally used in a 1.5 to 4-fold excess. When the condensation is found insufficient by ninhydrin assay, the reaction can be repeated to make the sufficient condensation thoroughly. When sufficient condensation can not be achieved by the repeated reaction, an unreacted amino acid can be acetylated by using acetic anhydride or acetylimidazole so as not to effect a subsequent reaction.

The protective groups for protecting the amino group of the starting compound include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulfenyl, diphenylphosphinothioyl, Fmoc, and so on.

The carboxyl group can be protected in the form of, for example, an alkyl ester (e.g. straight-chain, branched, or cyclic alkyl esters such as methyl, ethyl, propyl, butyl, t-butyl, cyclopentyl, cyclohexyl, cycloheptyl, cyclooctyl, 2-adamantyl, and so on), an aralkyl ester (e.g. benzyl, 4-nitrobenzyl, 4-methoxybenzyl, 4-chlorobenzyl, benzhydryl, and so on), phenacyl ester, benzyloxycarbonylhydrazide, t-butoxycarbonylhydrazide or tritylhydrazide.

The hydroxyl group of serine can be protected in the form of an ester or an ether. The group suitable for esterification includes carboxylic acid-derived acyl groups such as a lower($C_{1-6}$) alkanoyl group (e.g. acetyl, etc.), an aroyl group (e.g. benzoyl, etc.), a benzyloxycarbonyl, an ethoxycarbonyl group and so on. The group suitable for etherification includes a benzyl group, a tetrahydropyranyl group, a t-butyl group and so on.

The protective group used for protecting the phenolic hydroxyl group of tyrosine includes Bzl, $Cl_2$-Bzl, 2-nitrobenzyl, Br-Z, t-butyl and so on.

The protective group for the imidazole group of histidine includes Tos, 4-methoxy-2,3,6-trimethylbenzenesulfonyl, DNP, benzyloxymethyl, Bum, Boc, Trt, Fmoc and so on.

The starting compound with activated carboxyl group includes the corresponding acid anhydride, azide, and active ester (e.g. esters with alcohols such as pentachlorophenol, 2,4,5-trichlorophenol, 2,4-dinitrophenol, cyanomethyl alcohol, p-nitrophenol, HONB, N-hydroxysuccinimide, N-hydroxyphthalimide, HOBt, etc.). The starting compound with activated amino groups includes the corresponding phosphorylamide.

The method for removal of such protective groups includes catalytic reduction in a hydrogen stream in the presence of a catalyst (e.g. Pd black or Pd-on-carbon), acid treatment with anhydrous hydrogen fluoride, methanesulfonic acid, trifluoromethanesulfonic acid, trifluoroacetic acid or a mixture thereof, treatment with a base such as diisopropylethylamine, triethylamine, piperidine, piperazine or the like, and reduction with sodium metal in liquid ammonia. The above deprotection by treatment with acid is generally conducted at a temperature of about −20° C. to 40° C. This acid treatment can be carried out advantageously in the presence of a cation acceptor such as anisole, phenol, thioanisole, m-cresol, p-cresol, dimethyl sulfide, 1,4-butanedithiol, 1,2-ethanedithiol, or the like. The 2,4-dinitrophenyl group used for protecting the imidazole group of histidine can be removed by treatment with thiophenol, and the formyl group used for protecting the indole group of tryptophan can be removed not only by said acid treatment in the presence of 1,2-ethanedithiol, 1,4-butanedithiol or the like as described hereinbefore, but also by alkali treatment with diluted sodium hydroxide solution, diluted liquid ammonia, or the like.

The method for protecting any functional group that should not take part in the contemplated reaction, the protective group to be used for such protection, the method for eliminating the protective group, and the method for activating the functional group to be involved in the contemplated reaction can all be optionally selected from among the known methods and groups.

An alternative method for providing the protein or its partial peptide in amide form typically comprises protecting the α-carboxyl group of the C-terminal amino acid in the form of an amide, extending the peptide (protein) chain to a desired length towards the N-terminus, deprotecting the N-terminal α-amino acid of the resulting peptide chain selectively to provide an N-terminal-deprotected fragment, preparing a peptide (protein) fragment with its C-terminal carboxyl group selectively deprotected, and condensing the two fragments in a solvent such as the mixed solvent as mentioned above. The condensation reaction can be carried out in the same manner as described hereinbefore. After purification of the protected protein thus obtained by condensation, all the protective groups are eliminated by the procedures described hereinbefore to provide the contemplated protein in crude form. This crude protein is purified by suitable known purification techniques and lyophilized to provide the desired protein amide.

A method for providing the protein or its partial peptide in an ester form comprises condensing the α-carboxyl group of the C-terminal amino acid with a suitable alcohol to prepare the corresponding ester and subjecting this ester to the same procedure as described for purification of the protein amide to provide the objective ester of the protein or its partial peptide.

The partial peptide of the present invention or a salt thereof can be produced by per se known procedures for peptide synthesis or by cleaving the protein with a suitable peptidase. The process for peptide synthesis may be a solid-phase synthesis and/or a liquid-phase synthesis. Namely, the objective peptide can be produced by condensing a partial peptide or amino acid capable of constituting the protein with the residual part thereof and, when the product has a protective group, the protective group is removed whereupon a desire peptide can be manufactured. The known technology for condensation and deprotection includes the procedures described in the following literature (1)–(5).

(1) M. Bodanszky and M. A. Ondetti, Peptide Synthesis, Interscience Publishers, New York, 1966

(2) Schroeder and Luebke, The Peptide, Academic Press, New York, 1965

(3) Nobuo Izumiya et al., Fundamentals and Experiments in Peptide Synthesis, Maruzen, 1975

(4) Haruaki Yajima and Shumpei Sakakibara, Biochemical Experiment Series 1, Protein Chemistry IV, 205, 1977

(5) Haruaki Yajima (ed.), Development of Drugs-Continued, 14, Peptide Synthesis, Hirokawa Shoten After the reaction, the partial peptide of the present invention can be purified and isolated by a combination of conventional purification techniques such as solvent extraction, distillation, column chromatography, liquid chromatography, and recrystallization. When the partial peptide isolated as above is in a free form, it can be converted to a suitable salt by known methods or method analogous thereto. On the other hand, when it is isolated as a salt, it can be converted to a free form or to any other salt thereof by known methods or method analogous thereto.

The DNA coding for the protein of the present invention may be any DNA comprising a nucleotide sequence encoding the protein of the present invention as mentioned above. It may also be any one of genomic DNA, genomic DNA library, cDNA derived from the tissues or cells as mentioned above, cDNA library derived from the tissues or cells as mentioned above, and synthetic DNA.

The vector for constructing a library may include bacteriophage, plasmid, cosmid, and phagemid. Furthermore, using a total RNA fraction or a mRNA fraction prepared from the tissues or cells, a direct amplification can be carried out by Reverse Transcriptase Polymerase Chain Reaction (hereinafter, referred to as RT-PCR method) technique.

Examples of DNA coding for the protein having the amino acid sequence represented by SEQ ID NO:1 of the present invention are (1) a DNA comprising a nucleotide sequence represented by SEQ ID NO:4, or (2) a DNA which comprises a nucleotide sequence hybridizing to the nucleotide sequence represented by SEQ ID NO:4 under a high stringent condition and codes for a protein having a substantially equivalent activity (e.g. GFAT activity) to the protein comprising the amino acid sequence represented by ID No:1.

Examples of the DNA which comprises the nucleotide sequence hybridizing to the nucleotide sequence represented by SEQ ID NO:4 are a DNA comprising a nucleotide sequence of not less than about 80%, preferably not less than about 85%, more preferably not less than about 90%, for still better result, not less than about 95% identity to the nucleotide sequence represented by SEQ ID NO:4.

Examples of DNA coding for the protein having the amino acid sequence represented by SEQ ID NO:2 are (1) a DNA comprising a nucleotide sequence represented by SEQ ID NO:5, or (2) a DNA which comprises a nucleotide sequence hybridizing to the nucleotide sequence represented by SEQ ID NO:5 under a high stringent condition and codes for a protein having a substantially equivalent activity (e.g. GFAT activity) to the protein comprising the amino acid sequence represented by ID No:2, and so on.

Examples of the DNA which comprises the nucleotide sequence hybridizing to the nucleotide sequence represented by SEQ ID NO:5 are a DNA comprising a nucleotide sequence of not less than about 80%, preferably not less than about 85%, more preferably not less than about 90%, for still better result, not less than about 95% identity to the nucleotide sequence represented by SEQ ID NO:5.

Examples of DNA coding for the protein having the amino acid sequence represented by SEQ ID NO:3 are (1) a DNA comprising a nucleotide sequence represented by SEQ ID NO:6, or (2) a DNA which comprises a nucleotide sequence hybridizing to the nucleotide sequence represented by SEQ ID NO:6 under a high stringent condition and codes for a protein having a substantially equivalent activity (e.g. GFAT activity) to the protein comprising the amino acid sequence represented by ID No:3, and so on.

Examples of the DNA which comprises the nucleotide sequence hybridizing to the nucleotide sequence represented by SEQ ID NO:6 are a DNA comprising a nucleotide sequence of not less than about 80%, preferably not less than about 85%, more preferably not less than about 90%, for still better result, not less than about 95% identity to the nucleotide sequence represented by SEQ ID NO:6.

The hybridization can be carried out by per se known methods such as the method described in Molecular Cloning, 2nd (J. Sambrook et al., Cold Spring Harbor Lab. Press, 1989) and so on. When a commercially available library is used, the hybridization can be carried out in accordance with the instructions given in the accompanying manual, and particularly, be carried out under a high stringent condition.

Under the high stringent condition, $Na^+$ concentration is at about 19 to 40 mM, preferably about 19 to 20 mM and a temperature is at about 50° to 70° C., preferably about 60° to 65° C. Particularly, the condition at about 19 mM of $Na^+$ and about 65° C. is preferred.

Preferable examples of the DNA coding for the protein comprising the amino acid sequence represented by SEQ ID NO:1 are a DNA comprising the nucleotide sequence represented by SEQ ID NO:4.

Preferable examples of the DNA coding for the protein comprising the amino acid sequence represented by SEQ ID NO:2 are a DNA comprising the nucleotide sequence represented by SEQ ID NO:5.

Preferable example of the DNA coding for the protein comprising the amino acid sequence represented by SEQ ID NO:3 are a DNA comprising the nucleotide sequence represented by SEQ ID NO:6.

The DNA coding for the partial peptide of the present invention may be any DNA comprising a nucleotide sequence encoding the partial peptide of the present invention as mentioned above. It may also be any one of genomic DNA, genomic DNA library, cDNA derived from the tissues or cells as mentioned above, cDNA library derived from the tissues or cells as mentioned above, and synthetic DNA.

The vector for constructing a library may include bacteriophage, plasmid, cosmid, and phagemid. Furthermore, using a total RNA fraction or a mRNA fraction prepared from the tissues or cells, a direct amplification can be carried out by RT-PCR method.

Examples of DNA coding for the partial peptide of the present invention are (i) a DNA comprising a partial nucleotide sequence of DNA which comprises a nucleotide sequence represented by SEQ ID NO: 5 or SEQ ID NO:6, or (ii) a DNA comprising a partial nucleotide sequence of DNA which comprises a nucleotide sequence hybridizing under a high stringent condition to the nucleotide sequence represented by SEQ ID NO:5 or SEQ ID NO:6 and codes for a protein having a substantially equivalent activity (e.g. GFAT activity) to the protein of the present invention.

Examples of the nucleotide sequence hybridizing to the nucleotide sequence represented by SEQ ID NO:5 or SEQ ID NO:6 are a nucleotide sequence of not less than about 80%, preferably not less than about 90%, more preferably not less than about 95% identity to the nucleotide sequence represented by SEQ ID NO:5 or SEQ ID NO:6, and so on.

More specifically, examples of the DNA coding for the partial peptide having the amino acid sequence represented by SEQ ID NO: 7 are (i) a DNA having the nucleotide sequence represented by SEQ ID NO: 10, (ii) a DNA which has the nucleotide sequence hybridizing under a high stringent condition to the nucleotide sequence represented by SEQ ID NO: 10, and so on.

Examples of the the nucleotide sequence hybridizing to the nucleotide sequence represented by SEQ ID NO: 10 are a nucleotide sequence of not less than about 80%, preferably not less than about 90%, more preferably not less than about 95% identity to the nucleotide sequence represented by SEQ ID NO: 10, and so on.

Examples of the DNA coding for the partial peptide having the amino acid sequence represented by SEQ ID NO:8 are (i) a DNA having the nucleotide sequence represented by SEQ ID NO:11 , (ii) a DNA which has the nucleotide sequence hybridizing under a high stringent condition to the nucleotide sequence represented by SEQ ID NO:11, and so on.

Examples of the the nucleotide sequence hybridizing to the nucleotide sequence represented by SEQ ID NO:11 are a nucleotide sequence of not less than about 80%, preferably not less than about 90%, more preferably not less than about 95% identity to the nucleotide sequence represented by SEQ ID NO:11, and so on.

Examples of the DNA coding for the partial peptide having the amino acid sequence represented by SEQ ID NO:9 are (i) a DNA having the nucleotide sequence represented by SEQ ID NO:12, (ii) a DNA which has the nucleotide sequence hybridizing under a high stringent condition to the nucleotide sequence represented by SEQ ID NO:12, and so on.

Examples of the the nucleotide sequence hybridizing to the nucleotide sequence represented by SEQ ID NO:12 are a nucleotide sequence of not less than about 80%, preferably not less than about 90%, more preferably not less than about 95% identity to the nucleotide sequence represented by SEQ ID NO:12, and so on.

The method of hybridization and the high stringent condition are same as mentioned above.

More specifically, the DNA coding for the partial peptide having an amino acid sequence represented by SEQ ID NO:7 includes a DNA having a nucleotide sequence represented by SEQ ID NO:10 and so on. The DNA coding for the partial peptide having an amino acid sequence represented by SEQ ID NO:8 includes a DNA having a nucleotide sequence represented by SEQ ID NO:11 and so on. The DNA coding for the partial peptide having an amino acid sequence represented by SEQ ID NO:9 includes a DNA having a nucleotide sequence represented by SEQ ID NO:12 and so on.

The DNA encoding the protein or the partial peptide of the present invention can be cloned either by PCR amplification by using synthetic DNA primers having a partial nucleotide sequence of the DNA coding for the protein or by hybridization using the DNA inserted in a suitable vector and labeled DNA fragment or synthetic DNA coding for a part or full region of the protein or the partial peptide of the present invention. The hybridization can be carried out by the method described in Molecular Cloning, 2nd (J. Sambrook et al., Cold Spring Harbor Lab. Press, 1989). When a commercially available DNA library is used, the instructions given in the accompanying manual can be followed.

The substitution of the nucleotide sequence of the DNA can be carried out by the per se known method such as Gapped duplex method, Kunkel method and so on by using the known kits such as Mutan™-G (Takara), Mutan™-K (Takara) and so on.

The cloned DNA coding for the protein or the partial peptide of the present invention can be used directly or after digestion with a restriction enzyme or after addition of a linker depending on purposes. This DNA may have ATG as the translation initiation codon at the 5' end and TAA, TGA, or TAG as the termination codon at the 3' end. The translation initiation and termination codons can be added by means of suitable DNA adaptors.

An expression vector for the protein of the present invention can be constructed by, for example, (a) cutting out an objective DNA fragment from the DNA for the protein of the present invention and (b) ligating the objective DNA fragment with the downstream side of a promoter in a suitable expression vector.

The vector may include plasmids derived from *Escherichia coli*, e.g., pBR322, pBR325, pUC12, pUC13, etc.; plasmids derived from *Bacillus subtilis*, e.g., pUB110, pTP5, pC194, etc.; plasmids derived from yeasts e.g., pSH19, pSH15, ,etc.; bacteriophages such as λ-phage; animal virus such as retrovirus, vaccinia virus, etc.; insect virus; and other vectors such as pA1–11, pXT1, pRc/CMV, pRc/RSV, pcDNAI/Neo and so on.

According to the present invention, any promoter can be used as long as it is appropriate for the host cell which is used for expressing a gene. When the host is an animal cell, the promoter include SRα promoter, SV40 promoter, LTR promoter, CMV (cytomegalovirus) promoter, HSV-TK promoter, etc., and CMV promoter and SRa promoter are preferably used. When the host for the transformation is *Escherichia coli*, the promoter are preferably trp promoter, lac promoter, recA promoter, $\lambda P_L$ promoter, lpp promoter, T7 promoter, etc. When the host for the transformation is Bacillus, the promoter are preferably SPO1 promoter, SPO2 promoter, penP promoter, etc. When the host is a yeast, the promoter are preferably PHO5 promoter, PGK promoter, GAP promoter, ADH promoter, AOX1 promoter, etc. When the host is an insect cell, the promoter include polyhedrin promoter, P10 promoter, etc.

The expression vectors may, if necessary, further comprise enhancers, splicing signals, polyadenylation signals, selective markers, SV40 duplicate origin (hereinafter referred to as SV40 ori). Examples of selective markers are dihydrofolic acid reductase (hereinafter referred to as dhfr gene), ampicillin resistant gene (hereinafter referred to as Amp'), neomycin-resistant gene (hereinafter referred to as Neo) and so on. The dhfr gene gives methotrexate (MTX) registant and Neo gives G418 resistant. Particularly, when the dhfr gene is used as a selective marker against dhfr gene-deficient chinese hamster cell lines, cells transfected by the objective gene can be selected in a thymidine-free medium.

Furthermore, an appropriate signal sequence for a host can be added to the N-terminal side of the protein. When the host is *Escherichia coli*, the utilizable signal sequences may include PhoA signal sequence, OmpA signal sequence, etc. When the host is Bacillus, they may include α-amylase signal sequence, subtilisin signal sequence, etc. When the host is a yeast, they may include MFα signal sequence, SUC2 signal sequence, etc. When the host is an animal cell, they may include insulin signal sequence, α-interferon signal sequence, antibody molecule signal sequence, etc.

A transformant or transfectant is produced by using the vector thus constructed, which carries the DNA coding for the protein of the present invention.

The host may be, for example, Escherichia species, Bacillus species, yeast cells, insect cells, insects, animal cells, etc.

Examples of Escherichia species include *Escherichia coli* K12.DH1 (Proc. Natl. Acad. Sci. U.S.A., 60, 160 (1968)), JM103 (Nucleic Acids Research, 9, 309 (1981)), JA221 (J. Mol. Biol. 120, 517 (1978)), HB101 (J. Mol. Biol., 41, 459 (1969)), C600 (Genetics, 39, 440 (1954)), etc.

Examples of Bacillus species are, for example, *Bacillus subtilis* MI114 (Gene, 24, 255 (1983)), 207–21 (J. Biochem., 95, 87 (1984)), etc.

Examples of yeast cells are, for example, *Saccharomyces cerevisiae* AH22, AH22R$^-$, NA87-11A, DKD-5D or 20B-12, *Schizosachcaromyces pombe* NCYC1913 or NCYC2036, or *Pichia pastoris* KM71, etc.

Examples of insect cells are, for example, *Spodoptera frugiperda* cell (Sf cell), MG1 cell derived from center intestine of *Trichoplusia ni*, High Five™ cell derived from eggs of *Trichoplusia ni*, *Mamestra brassicae*-derived cell, Estigmena acrea-derived cell and so on when virus is AcNPV; and *Bombyx mori* N cell (BmN cell) and so on when virus is BmNPV. Examples of the Sf cell are, for example, Sf9 cell (ATCC CRL 1711), Sf21 cell (both, Vaughn J. L. et al., In Vivo, 13, 213–217 (1977)) and so on.

Examples of insects include a larva of silkworm (*Bombyx mori* larva) (Maeda et al., Nature, 315, 592 (1985)).

Examples of animal cells are, for example, monkey-derived COS-7 cell line, Vero cell line, Chinese hamster ovary cell line (hereinafter referred to as CHO cell), dhfr gene-deficient Chinese hamster cell line (hereinafter referred to as CHO(dhfr$^-$) cell), mouse L cell, mouse AtT-20 cell, mouse myeloma cell, rat GH3 cell, human FL cell, 293 cell, C127 cell, BALB/3T3 cell, Sp-2/O cell, etc. Among them, CHO cell, CHO(dhfr$^-$) cell, 293 cell, etc. are preferred.

Depending on host cells used, transformation is done using standard techniques appropriate to such cells.

Transformation of Escherichia species can be carried out in accordance with methods as disclosed in, for example, Proceedings of the National Academy of Sciences of the United State of America, Vol. 69, 2110 (1972), and Gene, Vol. 17, 107 (1982), etc. Transformation of Bacillus species can be carried out in accordance with methods as disclosed in, for example, Molecular & General Genetics, Vol. 168, 111 (1979), etc.

Transformation of yeast cells can be carried out in accordance with methods as disclosed in, for example, Methods in Enzymology, Vol. 194, 182–187 (1991), etc. Transformation of insect cells or insects can be carried out in accordance with methods as disclosed in, for example, Bio/Technology, Vol. 6, 47–55, (1988).

Transformation of animal cells can be carried out by methods as disclosed in, for example, Cell Engineering, separate Vol. 8, New Cell Engineering Experiment Protocol, 263–267 (1995) (Shujun Company), Virology, Vol. 52, 456 (1973), etc.

In introducing the expression vector into cells, known methods such as a calcium phosphate method (Graham, F. L. and van der Eb, A. J., Virology, 52, 456–467 (1973)), an electroporation (Neumann, E. et al., EMBO J., 1,841–845 (1982)), etc. may be used.

The transformants or transfectants wherein the expression vector carrying the DNA coding for the protein of the present invention can be obtained according to the aforementioned techniques.

Examples of methods for expressing the protein of the present invention stably using animal cells are a method for selecting the cells wherein the above-mentioned expression vector is incorporated in the chromosome by means of clone selection. Briefly, the transformant is first selected using the above-mentioned selective marker as an index for selection. Then the animal cell produced as such by using the selective marker is repeatedly subjected to a clone selection to give an animal cell strain which stably exhibits a high ability of expressing the protein of the present invention. When a dhfr gene is used as a selective marker, the drug-resistant cells are selected by a culture with a sequential increase in the MTX concentration to amplify the DNA coding for the protein of the present invention with dhfr gene in the cells whereby an animal cell strain exhibiting far higher expression can be obtained.

The protein of the present invention or a salt thereof can be also manufactured by culturing the transformant under a condition where the DNA coding for the protein of the present invention can be expressed to express and accumulate the protein of the present invention.

Culture of the transformants (or transfectants) of Escherichia or Bacillus species can be carried out preferably in a liquid culture medium. The culture medium may contains carbon sources, nitrogen sources, minerals, etc. which are necessary for growing the transformants. The carbon sources may include glucose, dextrin, soluble starch, sucrose, etc. The nitrogen sources may include organic or inorganic substances such as ammonium salts, nitrates, corn steep liquor, peptone, casein, meat extracts, bean-cakes, potato extracts, etc. Examples of minerals may include calcium chloride, sodium dihydrogen phosphate, magnesium chloride, etc. It is further allowable to add yeast extracts, vitamines, growth factors, etc. It is suitable that the pH of culture medium is at about 5 to 8.

The culture medium for Escherichia species is, for example, preferably M9 medium which contains glucose and casamino acid (Miller, Journal of Experiments in Molecular Genetics, 431–433, Cold Spring Harbor Laboratory, New York, (1972)). If necessary, drugs such as 3β-indolyl acrylic acid can be added to the medium to improve the efficiency of the promoter. In the case of Escherichia organisms as a host, the culture is carried out usually at about 15° to 43° C. for about 3 to 24 hours. As required, aeration and stirring may be applied. In the case of Bacillus organisms as a host, the culture is carried out usually at about 30° to 40° C. for about 6 to 24 hours. As required, aeration and stirring may also be applied.

In the case of yeast transformants, the culture medium used may include, for example, Burkholder minimum medium (Bostian, K. L. et al., Proc. Natl. Acad. Sci. U.S.A., 77, 4505 (1980)), SD medium containing 0.5% casamino acid (Bitter, G. A. et al., Proc. Natl. Acad. Sci. U.S.A., 81, 5330 (1984)), etc. It is preferable that the pH of the culture medium is adjusted to be from about 5 to 8. The culture is carried out usually at about 20° to 35° C. for about 24 to 72 hours. As required, aeration and stirring may be applied.

In the case of the transformants (or transfectants) of insect cells or insects, the culture medium used may include the Grace's insect medium supplemented with additives such as inactivated 10% bovine serum (Grace, T. C. C., Nature, 195, 788 (1962)). It is preferable that the pH of the culture medium is adjusted to be about 6.2 to 6.4. The culture is usually carried out at about 27° C. for about 3 to 5 days. As desired, aeration and stirring may be applied.

In the case of the transformants (or transfectants) of animal cells, the culture medium used may include MEM medium (Science, 122, 501 (1952)), DMEM medium (Virology, 8, 396 (1959)), RPMI 1640 medium (J. Amer. Med. Ass. 199, 519 (1967)), 199 medium (Proc. Sci. Biol.

Med. 73, 1 (1950)), etc. which are containing, for example, about 5 to 20% of fetal calf serum. It is preferable that the pH is from about 6 to 8. The culture is usually carried out at about 30° to 40° C. for about 15 to 72 hours. As required, medium exchange, aeration and stirring may be applied. Especially when CHO (dhfr⁻) cells and dhfr selective marker gene are used, it is preferred to use a DMEM medium containing a dialyzed fetal bovine serum which rarely contains thymidine.

Separation and purification of the protein from the above-mentioned cultures can be carried out according to methods described herein below.

To extract the protein from the cultured microorganisms or cells, the microorganisms or cells are collected by known methods after the culture, suspended in a suitable buffer solution, disrupted by ultrasonication, lysozyme and/or freezing and thawing, etc. and, then, a crude protein extract is obtained by centrifugation or filtration. Other conventional extraction or isolation methods can be applied. The buffer solution may contain a protein-denaturing agent such as urea or guanidine hydrochloride or a surfactant such as Triton X-100™.

In the case where proteins are secreted into culture media, supernatants are separated from the microorganisms or cells after culture and collected by known methods. The culture supernatant containing the protein can be purified by suitable combinations of known methods for separation, isolation and purification. The known methods of separation, isolation and purification may include methods which utilizes solubility, such as salting out or sedimentation with solvents, methods which utilizes chiefly a difference in the molecular size or weight, such as dialysis, ultrafiltration, gel filtration and SDS-polyacrylamide gel electrophoresis, methods utilizing a difference in the electric charge, such as ion-exchange chromatography, methods utilizing specific affinity such as affinity chromatography, methods utilizing a difference in the hydrophobic property, such as reversed-phase high-performance liquid chromatography, and methods utilizing a difference in the isoelectric point such as isoelectric electrophoresis, etc.

In cases where the protein thus obtained is in a free form, it can be converted to a salt thereof by known methods or method analogous thereto. In case, where the protein thus obtained is in a salt form vice versa, it can be converted to a free form or to any other salt thereof by known methods or method analogous thereto.

The protein produced by the transformant can be arbitrarily modified or a polypeptide can be partly removed therefrom, by a suitable protein-modifying enzyme before or after the purification. The protein-modifying enzyme may include trypsin, chymotrypsin, arginyl endopeptidase, protein kinase, glycosidase, etc. The existence or activity of the protein of the present invention thus obtained can be detected or determined by binding assay with a labeled ligand or by enzyme immunoassays (enzyme linked immunoassays) using specific antibodies, respectively.

The antibodies against the protein of the present invention, its partial peptide or a salt thereof are any antibodies such as polyclonal antibodies and monoclonal antibodies which can recognize the protein of the present invention, its partial peptide or a salt thereof (hereinafter referred to as the protein of the present invention).

The antibodies against the protein of the present invention may be manufactured by methods per se known to those of skill in the art or methods similar thereto, using the protein of the present invention as an antigen. For example, polyclonal antibodies can be manufactured by the method as given below.

Preparation of a Monoclonal Antibody (a) Preparation of Monoclonal Antibody-Producing Cells The protein of the present invention is administered to warm-blooded animals either solely or together with carriers or diluents to the site favorable for antibody production. In order to potentiate the antibody productivity upon the administration, complete Freund's adjuvants or incomplete Freund's adjuvants may be administered. The administration is usually carried out once every 2 to 6 weeks and 2 to 10 times in total. Examples of the applicable warm-blooded animals are monkeys, rabbits, dogs, guinea pigs, mice, rats, sheep, goats and chickens. The use of mice and rats is preferred.

In establishing cells which produce monoclonal antibodies, an animal with the detectable antibody titer is selected from animals (e.g. mice) immunized with antigens, then spleen or lymph node is collected after 2 to 5 days from the final immunization and antibody-producing cells contained therein are fused with myeloma cells derived from homogeneous or heterogeneous animals to obtain monoclonal antibody-producing hybridomas. Measurement of the antibody titer in antisera may, for example, be carried out by reacting a labeled protein, which will be mentioned later, with the antiserum followed by determining the binding activity of the labeling agent combined with the antibody. The cell fusion may be carried out, for example, by a method of Koehler and Milstein (Nature, 256, 495 (1975)). Examples of the fusion accelerator are polyethylene glycol (PEG), Sendai virus, etc. and the use of PEG is preferred.

Examples of the myeloma cells are those derived from warm-blooded animals such as NS-1, P3U1, SP2/0, AP-1, etc. and the use of P3U1 is preferred. The preferred fusion ratio of the numbers of antibody-producing cells used (spleen cells) to the numbers of myeloma cells is within a range of about 1:1 to 20:1. When PEG (preferably, PEG 1000 to PEG 6000) is added in a concentration of about 10 to 80% followed by incubating at 20° to 40° C., preferably, at 30° to 37° C., for 1 to 10 minutes, an efficient cell fusion can be carried out.

Various methods may be applied for screening a hybridoma which produces a monoclonal antibody. For example, a supernatant of hybridoma culture is added to a solid phase (e.g. microplate) to which the protein antigen is adsorbed either directly or with a carrier, then anti-immunoglobulin antibody (anti-mouse immunoglobulin antibody is used when the cells used for the cell fusion are those of mouse) which is labeled with a radioactive substance, an enzyme or the like, or protein A is added thereto and then monoclonal antibodies bound on the solid phase are detected; or a supernatant of the hybridoma culture is added to the solid phase to which anti-immunoglobulin or protein A is adsorbed, then the protein labeled with a radioactive substance or an enzyme is added and monoclonal antibodies bound with the solid phase is detected.

Selection and cloning of the monoclonal antibody-producing hybridoma may be carried out by methods per se known to those of skill in the art or methods similar thereto. Usually, it is carried out in a medium for animal cells, containing HAT (hypoxanthine, aminopterin and thymidine). With respect to a medium for the selection, for the cloning and for the growth, any medium may be used so far as hybridoma is able to grow therein. Examples of the medium are an RPMI 1640 medium (Dainippon Pharmaceutical Co., Ltd., Japan) containing 1 to 20% (preferably 10 to 20%) of fetal calf serum (FCS), GIT medium (Wako Pure Chemical, Japan) containing 1 to 20% of fetal calf serum and a suitable serum-free medium for hybridoma (SFM-101;

Nissui Seiyaku, Japan). The culture temperature is usually 20° to 40° C. and, preferably, about 37° C. The culture period is usually from 5 days to 3 weeks and, preferably, 1 to 2 weeks. The culture is usually carried out in 5% carbon dioxide gas. The antibody titer of the supernatant of the hybridoma culture may be measured by the same manner as in the above-mentioned measurement of the antibody titer in the antiserum.

(b) Purification of the Monoclonal Antibody

The separation and purification of the monoclonal antibody may be carried out by methods for separating/purifying immunoglobulin such as salting-out, precipitation with alcohol, isoelectric precipitation, electrophoresis, adsorption/deadsorption using ion exchangers such as DEAE, ultracentrifugation, gel filtration, specific purifying methods in which only an antibody is collected by treatment with an active adsorbent such as an antigen-binding solid phase, protein A or protein G and the bond is dissociated whereupon the antibody is obtained.

Preparation of a Polyclonal Antibody

The polyclonal antibody of the present invention can be produced by per se known methods or methods analogous thereto. The method comprises preparing an immunogen (antigen protein) per se or a conjugate of an imunogen with a carrier protein, immunizing a warm-blooded animal in the same manner as described for the production of the monoclonal antibody, harvesting a fraction containing the antibody against the protein of the present invention from the immunized animal, and purifying the harvested antibody.

Referring to the immunogen-carrier protein conjugate for use in the immunization of a warm-blooded animal, the kind of carrier protein and the ratio of the carrier and hapten are not particularly restricted only if the production of the antibody against the hapten conjugated with the particular carrier protein and used for immunization proceeds efficiently. Thus, for example, bovine serum albumin, bovine thyroglobulin, hemocyanine, or the like is coupled in the weight ratio of about 0.1 to 20, preferably about 1 to about 5, to unity of the hapten.

A variety of condensing agents can be used for this coupling between the hapten and the carrier. Thus, for example, a glutaraldehyde, carbodiimide, maleimide, or a thiol or dithiopyridyl group-containing active ester reagent can be employed.

The condensation reaction product is administered to a warm-blooded animal at a site favorable for antibody production, either as it is alone or together with a carrier or a diluent. Enhancing antibody production, complete Freund's adjuvant or incomplete Freund's adjuvant may be administered. Administration is carried out generally once in about 2 to 6 weeks for a total of about 3 to 10 times.

The polyclonal antibody can be harvested from the blood, ascites fluid, or other body fluid, preferably from the blood, of the host warm-blooded animal.

The polyclonal antibody titer in the antiserum can be determined in the same manner as the determination of a monoclonal antibody described hereinbefore. The separation and purification of the polyclonal antibody can be carried out by the same method as that described for the separation and purification of a monoclonal antibody.

The antisense DNA having a nucleotide sequence complementary or substantially complementary to the DNA or mRNA coding for the protein or the partial peptide of the present invention (hereinafter referred to as the DNA or mRNA of the present invention) can be any antisense DNA which is an oligonucleotide or a derivative thereof having a nucleotide sequence complementary or substantially complementary to that of the DNA or mRNA of the present invention and capable of suppressing expression of the protein.

The nucleotide sequence substantially complementary to the DNA or mRNA of the present invention may, for example, be a nucleotide sequence having an identity of not less than about 80%, preferably not less than about 85%, more preferably not less than about 90%, and for still better results, not less than about 95% to the total nucleotide sequence or partial nucleotide sequence of the nucleotide sequence complementary to that the DNA or mRNA of the present invention. Particularly preferred is an antisense DNA having an identity of not less than about 80%, preferably not less than about 85%, and more preferably not less than about 90%, and for still better results, not less than about 95% to the nucleotide sequence of the domain, of the complete nucleotide sequence complementary to that of the DNA or mRNA of the present invention, which encodes the N-terminal region of the protein of the present invention (e.g. the nucleotide sequence of the domain around the initiation codon). The antisense DNA can be synthesized using a known DNA synthesis hardware.

The protein, its partial peptide or a salt thereof of the present invention shows a GFAT activity, catalyzing the conversion of fructose-6-phosphate to glucosamine-6-phosphate in the hexosamine biosynthesis pathway, and particularly exhibits a relatively high activity in the conversion of fructose-6-phosphate to glucosamine-6-phosphate. Therefore, the protein, its partial peptide or a salt thereof of the present invention can be used in various applications.

Typical applications of the protein, its partial peptide or a salt thereof of the present invention (hereinafter referred to collectively as the protein or equivalent of the present invention), the DNA coding for the protein, etc. of the present invention (hereinafter briefly referred to as the DNA of the present invention), the antibody against the protein, etc. of the present invention (hereinafter briefly referred to as the antibody of the present invention) and the antisense DNA.

(1) Medicinal products such as therapeutic and prophylactic agents for various diseases The protein or equivalent of the present invention and the DNA of the present invention are useful as drugs such as therapeutic or prophylactic agent for a GFAT-encoding gene defect and associated diseases therewith, a GFAT dysfunction and associated diseases therewith (e.g. hypoglycemia) and so on.

For example, when there is a patient whose GFAT in the body cannot function sufficiently or normally because of its decrease or defect, GFAT of the patient can be expected to be functioned sufficiently or normally by:

(a) administering the DNA coding for the protein or equivalent of the present invention to the patient to express it;

(b) inserting the DNA coding for the protein or equivalent of the present invention into cells to express it and transplanting the cells to the patient, or (c) administering the protein or equivalent of the present invention to the patient.

For example, the protein or equivalent of the present invention can be used orally in the form of tablets which may be sugar coated as necessary, capsules, elixirs, microcapsules etc., or non-orally in the form of injectable preparations such as aseptic solutions and suspensions in water or other pharmaceutically acceptable liquids. These preparations can be produced by mixing the protein or equivalent of the present invention with physiologically acceptable carriers, flavoring agents, excipients, vehicles, antiseptics, stabilizers, binders etc. in unit dosage forms required for generally accepted manners of pharmaceutical preparation. Active ingredient contents in these preparations are set so that an appropriate dose within the specified range is obtained.

When the DNA of the present invention is used as the above-mentioned pharmaceutical composition, said DNA may be used alone or after inserting it into a suitable vector such as retrovirus vector, adenovirus vector, adenovirus-associated virus vector, pox virus etc. followed by subjecting the product vector to a conventional means. The DNA can also be administered as "naked" DNA, with physiologically acceptable carriers such as adjuvants to assist in uptake, by "gene" gun or by a catheter such as a catheter with a hydrogel.

If one wishes to use the protein or equivalent of the present invention, one would use it in a purified form, preferably in a purity of at least 90%, more preferably at least 95%, still more preferably at least 98% and most preferably at least 99%.

Additives which can be mixed in tablets, capsules etc. include binders such as gelatin, corn starch, tragacanth and gum arabic, excipients such as crystalline cellulose, swelling agents such as corn starch, gelatin and alginic acid, lubricants such as magnesium stearate, sweetening agents such as sucrose, lactose and saccharin, and flavoring agents such as peppermint, akamono oil and cherry. When the unit dosage form is the capsule, the above-mentioned materials may further incorporate liquid carriers such as oils and fats. Sterile compositions for injection can be formulated by ordinary methods of pharmaceutical preparation such as by dissolving or suspending active ingredients, naturally occurring vegetable oils such as sesame oil and coconut oil, etc. in vehicles such as water for injection to create pharmaceutical compositions.

Aqueous liquids for injection include physiological saline and isotonic solutions containing glucose and other auxiliary agents, e.g., D-sorbitol, D-mannitol and sodium chloride, and may be used in combination with appropriate dissolution aids such as alcohols, e.g., ethanol, polyalcohols, e.g., propylene glycol and polyethylene glycol, nonionic surfactants, e.g., polysorbate 80™ and HCO-50 etc. Oily liquids include sesame oil and soybean oil, and may be used in combination with dissolution aids such as benzyl benzoate and benzyl alcohol. Furthermore the above-mentioned materials may also be formulated with buffers, e.g., phosphate buffer and sodium acetate buffer; soothing agents, e.g., benzalkonium chloride, procaine hydrochloride; stabilizers, e.g., human serum albumin, polyethylene glycol; preservatives, e.g., benzyl alcohol, phenol; antioxidants etc. The thus-prepared pharmaceutical composition such as an injectable liquid is normally filled in an appropriate ampule.

The vector comprising the DNA of the present invention can be formulated as well as mentioned above, and usually can be used non-orally.

Because the thus-obtained preparation is safe and of low toxicity, it can be administered to mammals (e.g., human, rat, mouse, guinia pig, rabbit, sheep, pig, bovine, horse, cat, dog, monkey, etc.).

The dose of the protein or equivalent of the present invention may vary depending on subject of disease, subject of administration, way of administration, and so on. When the protein or equivalent of the present invention is used, for example, for treating hypoglycemia by oral administration, the dose of the protein or equivalent of the present invention is normally about 0.1 to 100 mg, preferably 1.0 to 50 mg, and more preferably 1.0 to 20 mg per day for an adult (weighing 60 kg). When the protein or equivalent of the present invention is used, for example, for treating hypoglycemia by non-oral administration, it is advantageous to administer the protein or equivalent of the present invention in the form of injectable preparation at a daily dose of about 0.01 to 30 mg, preferably about 0.1 to 20 mg, and more preferably about 0.1 to 10 mg per administration by an intravenous injection for an adult (weighing 60 kg), depending on subject of administration, subject disease and so on. For other animal species, corresponding does as converted per 60 kg weight can be administered.

(2) Gene diagnostic agent

By using the DNA of the present invention as a probe, for instance, an abnormality (gene abnormality) of the DNA or mRNA coding for the protein of the present invention or its partial peptide in mammals (e.g. human, rat, mouse, guinea pig, rabbit, sheep, swine, bovine, horse, cat, dog, monkey, chimpanzee, etc.) can be detected. Therefore, the DNA of the present invention is useful as a gene diagnostic agent for the damage to the DNA or mRNA, mutation thereof, or decreased expression thereof, or increased expression or overexpression of the DNA or mRNA.

For example, when the increase of the DNA or mRNA coding for the protein or equivalent of the present invention or the increase of the protein or equivalent of the present invention is detected, it may be lead to the diagnosis of diabetes and so on.

On the other hand, the deficit or lack of the DNA or mRNA expression or the decrease of the protein or equivalent of the present invention is detected, it may be lead to the diagnosis of hypoglycemia and so on.

The above-mentioned gene diagnosis using the DNA of the present invention can be carried out by, for example, the per se known Northern hybridization assay or PCR-SSCP assay (Genomics, 5, 874–879 (1989); Proc. Natl. Acad. Sci. U.S.A., 86, 2766–2770 (1989)).

When an increase in expression of the mRNA coding for the protein or equivalent of the present invention is detected by Northern hybridization assay, it may lead, with high probability, to the diagnosis of diabetes and so on.

When a decrease in expression of the mRNA is detected, it may lead, with high probability, to the diagnosis of hypoglycemia and so on.

When a mutation of the DNA is detected by the PCR-SSCP assay, it may lead, with high probability, to the diagnosis of diabetes, hypoglycemia and so on.

(3) Quantitative determination of the protein of the present invention

The antibody of the present invention is capable of specifically recognizing the protein or equivalent of the present invention and, accordingly, it can be used for quantitative determination of the protein or equivalent of the present invention in test liquid samples and particularly for quantitative determination by sandwich immunoassays.

Thus, the present invention provides, for example, the following methods:

(i) a quantitative determination of the protein or equivalent of the present invention in a test liquid sample, which comprises
  (a) competitively reacting the test liquid sample and a labeled protein or equivalent of the present invention with the antibody of the present invention, and
  (b) measuring the ratio of the labeled protein or equivalent of the present invention binding with said antibody; and
(ii) a quantitative determination of the protein or equivalent of the present invention in a test liquid sample, which comprises (a) reacting the test liquid sample with an antibody immobilized on an insoluble carrier and a labeled antibody simultaneously or continuously, and (b) measuring the activity of the labeling agent on the insoluble carrier, wherein one antibody is capable of recognizing the N-terminal region of the protein or equivalent of the present invention while another antibody is capable of recognizing the C-terminal region of the protein or equivalent of the present invention.

When the monoclonal antibody of the present invention recognizing the protein or equivalent of the present invention (hereinafter, sometimes referred to as "monoclonal antibody of the present invention") is used, the quantity of the protein or equivalent of the present invention can be determined and, moreover, the protein or equivalent of the present invention can be detected by means of a tissue staining, etc. as well. For such an object, antibody molecules per se may be used, or F(ab')$_2$, Fab' or Fab fractions of the antibody molecule may also be used. There is no particular limitation for the measuring method using the antibody of the present invention and any measuring method may be used so far as it relates to a method in which the amount of antibody, antigen or antibody-antigen complex, depending on or corresponding to the amount of antigen, e.g. the amount of the protein or equivalent of the present invention in the liquid sample to be determined, is detected by a chemical or a physical means and then calculated using a standard curve prepared by a standard solution containing the known amount of antigen. For exmaple, nephrometry, competitive method, immunometric method and sandwich method are suitably used and, in terms of sensitivity and specificity, the sandwich method which will be described herein later is particularly preferred.

Examples of the labeling agent used in the measuring method using the labeling substance are radioisotopes, enzymes, fluorescent substances, luminescent substances, colloids, magnetic substances, etc. Examples of the radioisotope are [$^{125}$I], [$^{131}$I], [$^3$H] and [$^{14}$C]. Preferred examples of the enzyme are those which are stable and with much specific activity, such as β-galactosidase, β-glucosidase, alkaline phosphatase, peroxidase and malate dehydrogenase. Examples of the fluorescent substance are fluorescamine, fluorescein isothiocyanate, etc. Examples of the luminescent substance are luminol, luminol derivatives, luciferin, lucigenin, etc. Further, a biotin-avidin system may also be used for binding an antibody or an antigen with a labeling agent.

In an insolubilization (immobilization) of antigens or antibodies, a physical adsorption may be used or a chemical binding which is usually used for insolubilization or immobilization of proteins or enzymes may be used as well. Examples of the carrier are insoluble polysaccharides such as agarose, dextran and cellulose; synthetic resins such as polystyrene, polyacrylamide and silicone; glass; etc.

In a sandwich method, the test liquid is made to react with an insolubilized monoclonal antibody of the present invention (the first reaction), then it is allowed to react with an another labeled monoclonal antibody of the present invention (the second reaction) and the activity of the labeling agent on the insoluble carrier is measued whereupon the amount of the protein or equivalent of the present invention in the test liquid can be determined. The first reaction and the second reaction may be conducted reversely or simultaneously or they may be conducted with an interval. The type of the labeling agent and the method of insolubilization may be the same as those mentioned hereinbefore. In the immunoassay by means of a sandwich method, it is not always necessary that the antibody used for the labeled antibody and the antibody for the solid phase is one type or one species but, with an object of improving the measuring sensitivity, etc., a mixture of two or more antibodies may be used as well.

In the method of measuring the protein or equivalent of the present invention by the sandwich method of the present invention, the preferred monoclonal antibodies of the present invention used for the first and the second reactions are antibodies wherein their sites binding to the protein or equivalent of the present invention are different from each other. Thus, antibodies used in the first and the second reactions are those wherein, when an antibody used in the second reaction recognizes the C-terminal region of the protein or equivalent of the present invention, then another antibody recognizing the site other than C-terminal regions, e.g. recognizing the N-terminal region, is preferably used in the first reaction.

The monoclonal antibody of the present invention may be used in a measuring system other than the sandwich method such as a competitive method, an immunometric method and a nephrometry. In the competitive method, an antigen in the test solution and a labeled antigen are allowed to react with an antibody in a competitive manner, then an unreacted labeled antigen (F) and a labeled antigen (B) binding with an antibody are separated (i.e. B/F separation) and the labeled amount of any of B and F is measured whereupon the amount of the antigen in the test solution is determined. With respect to a method for such a reaction, there are a liquid phase method in which a soluble antibody is used as the antibody and the B/F separation is conducted by polyethylene glycol, a second antibody to the above-mentioned antibody, etc.; and a solid phase method in which an immobilized antibody is used as the first antibody or a soluble antibody is used as the first antibody while an immobilized antibody is used as the second antibody.

In the immunometric method, an antigen in the test solution and an immobilized antigen are subjected to a competitive reaction with a certain amount of a labeled antibody followed by separating into solid and liquid phases or the antigen in the test solution and an excess amount of labeled antibody are allowed to react, then an immobilized antigen is added to bind an unreacted labeled antibody with the solid phase and separated into solid and liquid phases. After that, the labeled amount of any of the phases is measured to determine the antigen amount in the test solution.

In the nephrometry, the amount of insoluble sediment which is produced as a result of the antigen-antibody reaction in a gel or in a solution is measured. Even when the antigen amount in the test solution is small and only a small amount of the sediment is obtained, a laser nephrometry wherein scattering of laser is utilized can be suitably used.

In applying each of those immunological measuring methods (immunoassays) to the measuring method of the present invention, it is not necessary to set up any special condition, operation, etc. therefor. A measuring system (assay system) for the protein of the present invention may be constructed taking the technical consideration of the persons skilled in the art into consideration in the conventional conditions and operations for each of the methods. With details of those conventional technical means, a variety of reviews, reference books, etc. may be referred to.

They are, for example, Hiroshi Irie (ed): "Radioimmunoassay" (Kodansha, Japan, 1974); Hiroshi Irie (ed): "Radioimmunoassay; Second Series" (Kodansha, Japan, 1979); Eiji Ishikawa et al. (ed): "Enzyme Immunoassay" (Igaku Shoin, Japan, 1978); Eiji Ishikawa et al. (ed): "Enzyme Immunoassay" (Second Edition) (Igaku Shoin, Japan, 1982); Eiji Ishikawa et al. (ed): "Enzyme Immunoassay" (Third Edition) (Igaku Shoin, Japan, 1987); "Methods in Enzymology" Vol. 70 (Immunochemical Techniques (Part A)); ibid. Vol. 73 (Immunochemical Techniques (Part B)); ibid. Vol. 74 (Immunochemical Techniques (Part C)); ibid. Vol. 84 (Immunochemical Techniques (Part D: Selected (Immunoassays)); ibid. Vol. 92 (Immunochemical Techniques (Part E: Monoclonal Antibodies and General Immunoassay Methods)); ibid. Vol. 121 (Immunochemical Techniques (Part I: Hybridoma Technology and Monoclonal Antibodies)) (Academic Press); etc.

By using the antibody of the present invention in the above manner, the protein of the present invention can be assayed with high sensitivity.

In addition, by quantitative determination of the protein or equivalent of the present invention using the antibody of the present invention, various desease associated with the protein or equivalent of the present invention can be diagnozed.

When a decrease in concentration of the protein or equivalent of the present invention is detected by determining the concentration of the protein or equivalent of the present invention by using the antibody of the present invention, it may lead, with high probability, to the diagnosis of various diseases such as hypoglycemia and so on.

When an increase in concentration of the protein or equivalent of the present invention is detected, it may lead, with high probability, to the diagnosis of various diseases such as diabetes and so on.

Thus, the antibody of the present invention is useful as a diagnostic agent for the above-mentioned diseases.

Furthermore, the antibody of the present invention can be used for the purpose of detecting the protein of the present invention which may be present in test samples such as body fluids or tissues. The antibody can also be used for the construction of an antibody column for purification of the protein of the present invention, detection of the protein of the present invention in the fractions in the course of purification, and analysis of the behavior of the protein of the present invention in the test cell.

(4) Pharmaceutical compositions containing the antibody of the present invention Of the antibody of the present invention, those species which are capable of binding the protein or equivalent of the present invention to neutralize its GFAT activity inhibits the GFAT activity of the protein or equivalent of the present invention and can therefore be used as drugs, such as therapeutic or prophylactic composition for diabetes and other diseases.

The above-mentioned therapeutic or prophylactic composition containing the antibody of the present invention can be administered either orally or otherwise to mammals (e.g. human, rat, rabbit, sheep, swine, cattle, cat, dog, monkey), in the form of an antibody solution as such or in the form of a pharmaceutical composition having an appropriate dosage form.

The dosage is dependent on the recipient, target disease, symptom, administration route, and other factors. Generally, however, in the therapy or prevention of diabetes in a human adult, for instance, the antibody capable of neutralizing the GFAT activity of the protein or equivalent of the present invention can be administered, by the intravenous route, in a single dose of about 0.01 to 20 mg/kg body weight, preferably 0.1 to 10 mg/kg body weight, or more preferably about 0.1 to 5 mg/kg body weight, about 1 to 5 times a day, or preferably about 1 to 3 times a day. For administration by other routes and for oral administration, the dosage can be selected using the above dosage schedule as a reference. In cases presenting with particularly severe symptoms, the dosage may be increased according to the condition.

The antibody of the present invention which neutralizes the GFAT activity of the protein or equivalent of the present invention can be administered either as it is or in the form of a suitable pharmaceutical composition. The pharmaceutical composition comprises the antibody or its salt and a pharmaceutically acceptable carrier, diluent, or excipient. The composition can be provided in various, dosage forms suited for oral administration or non-oral administration.

The composition for oral administration, for instance, includes solid and liquid dosage forms such as tablets (including dragees, film-coated tablets), pills, granules, powders, capsules (including soft capsules), syrup, emulsion, suspension, etc. Such dosage forms can be manufactured by the per se known procedures and contain a carrier, diluent or excipient which is generally included in pharmaceutical formulations. The carrier or excipient for tablets includes but is not limited to lactose, starch, sucrose, and magnesium stearate.

The composition for non-oral administration may be used, for example, as an injectable product or a suppository. The injectable product includes intravenous, subcutaneous, intradermal, intramuscular, drip, and other injections. Such injections can be prepared by the per se known procedures, for example, by dissolving, suspending, or emulsifying the antibody or salt in a sterile aqueous or oily vehicle which is generally used in the manufacture of injectable products. The aqueous vehicle for injections includes physiological saline and various isotonic solutions containing glucose and/or the like and may be supplemented with a suitable solubilizer such as alcohols (e.g. ethanol), polyols (e.g. propylene glycol, polyethylene glycol), nonionic surfactants (polysorbate 80, HCO-50 (polyoxyethylene (50 mol)-hydrogenated castor oil adduct)), etc. The oily vehicle includes but is not limited to sesame oil and soybean oil. Benzyl benzoate, benzyl alcohol, etc. may also be used as solubilizers. Injections thus prepared are provided as filled in suitable ampules. Suppositories for rectal administration can be manufactured by mixing said antibody or salt with any of the conventional suppository bases.

The above pharmaceutical composition for oral or non-oral administration can be conveniently provided in unit dosage forms suited for delivery of the unit dose of the active ingredient. The unit dosage form may, for example, be the above-mentioned tablet, pill, capsule, injection (ampule) or suppository. Preferably, the amount of said antibody or salt per unit dosage form is generally 5–500 mg and preferably 5–100 mg for injectable products or 10–250 mg for other products.

The foregoing composition may contain other active ingredients unless their formulation with said antibody or salt results in unfavorable interactions.

(5) Screening for a candidate compound for use as a drug for various diseases

A compound, or a salt thereof, which promotes the enzyme activity (e.g. GFAT activity) of the protein of the present invention can be used as a drug such as a therapeutic or prophylactic agent for various diseases such as hypoglycemia.

On the other hand, a compound, or a salt thereof, which inhibits the enzyme activity of the protein of the present invention can be used as a drug such as a therapeutic or prophylactic agent for various diseases such as diabetes.

Therefore, the protein or equivalent of the present invention is useful as a reagent for the screening of compounds or their salts which promote or inhibit the enzyme activity of the protein of the present invention.

Thus, the present invention provides:

(1) A method for screening for a compound, or a salt thereof, which promotes or inhibits the enzyme activity (e.g. GFAT activity) of the protein or equivalent of the present invention (such compounds are hereinafter sometimes referred to as GFAT promoters or GFAT inhibitors), which comprises using the protein or equivalent of the present invention and, more particularly, for example, (2) A method for screening for GFAT promoters or GFAT inhibitors which comprises comparing the result, in cases of (i) a substrate is contacted with the protein or equivalent of the present invention and (ii) the substrate and a test compound are contacted with the protein or equivalent of the present invention.

More specifically, the screening method mentioned above is characterized in that the GFAT activities of the protein or equivalent of the present invention in the above cases (i) and (ii) are assayed and compared.

Examples of the substrate are any substance capable of serving as a substrate for the protein or equivalent of the present invention. For example, fructose-6-phosphate and glutamine are generally used. Fructose-6-phosphate is preferably used in the radiolabeled (e.g. $^{14}$C- or $^{3}$H-labeled) form.

Examples of the test compound are peptides, proteins, nonpeptide compounds, synthetic compounds, fermentation products, cell extracts, plant extracts, animal tissue extracts, blood plasma and so on. They may be novel or known compounds.

For carrying out the above screening method, a standard sample of the protein or equivalent of the present invention is first prepared by suspending the protein or equivalent of the present invention in a buffer suited for purposes of screening. The buffer may be any buffer that does not affect the binding of the protein or equivalent of the present invention to the substrate, thus including but not limited to phosphate buffer and Tris-HCl buffer, with a pH of about 4 to 10 (desirably about 6 to 8).

The GFAT activity of the protein or equivalent of the present invention can be assayed by a per se known method, for example the method of Smith et al. (Anal. Biochem., 98, 478–480 (1979)). Thus, for example, a solution prepared by adding the protein or equivalent of the present invention to a mixed solution comprising 12 $\mu$M fructose-6-phosphate, 5 $\mu$M glutamine and 0.2M phosphate buffer (pH 8.0) is incubated at 25° C. for 30 minutes. To this solution is added 0.5M hydrochloric acid and, after 2 hours of reaction at 98° C., 2.5% $NaNO_2$ and 12.5% $NH_4O_3SNH_2$ are added, followed by further addition of 0.25% 2-methyl-2-benzothiazolone. Then, 0.5% $FeCl_3$ is added and the absorbance (650 nm) of the solution is measured to determine the resulting amount of glucosamine-6-phosphate.

For example, when the GFAT activity is promoted by not less than about 20%, preferably not less than about 30%, more preferably not less than about 50% in the above case (ii), as compared with the case (i), then the compound tested can be selected as a compound capable of promoting the GFAT activity of the protein or equivalent of the present invention. On the other hand, when, for example, the GFAT activity in the above case (ii) is inhibited by not less than about 20%, preferably not less than about 30%, more preferably not less than about 50%, as compared with the case (i), then the compound tested can be selected as a compound capable of inhibiting the GFAT activity of the protein or equivalent of the present invention.

The screening kit of the present invention includes the protein or equivalent of the present invention. As an example of the screening kit of the present invention, the following may be mentioned. Reagents for screening:

(1) Screening buffer 0.2M phosphate buffer (pH 8.0)

(2) Standard protein The protein or equivalent of the present invention (3) Substrate 12 $\mu$M fructose-6-phosphate, 5 $\mu$M glutamine (4) Detection The absorbance at 650 nm is measured. Assay method:

The test compound is added to a reaction mixture comprising 12 $\mu$M fructose-6-phosphate, 5 82 M glutamine, the protein or equivalent of the present invention, and 0.2M phosphate buffer (pH 8.0). The resulting mixture is then incubated at 25° C. for 30 minutes. To this mixture is added 0.5M hydrochloric acid, and a hydrolysis reaction is carried out at 98° C. for 2 hours. Thereafter, 2.5% $NaNO_2$ and 12.5% $NH_4O_3SNH_2$ are added and, then, 0.25% 2-methyl-2-benzothiazolone is added. Then, after further addition of 0.5% $FeCl_3$, the absorbance at 650 nm is measured.

The compound or a salt thereof can be obtained from the test compounds as mentioned above, and may be any one of the test compounds such as peptides, proteins, non-peptide compounds, synthetic compounds, fermentation products, cell extracts, plant extracts, animal tissue extracts or blood plasma. The such compounds may be novel or known compounds. The compound can promote or inhibit the enzyme activity of the protein or equivalent of the present invention.

The salts of the compound identified by the screening method as mentioned above includes salts with physiologically acceptable bases (e.g. alkali metals) or acids such as organic or inorganic acids, and is preferably a physiologically acceptable acid addition salt. Examples of such salts are salts thereof with inorganic acids (e.g. hydrochloric acid, phosphoric acid, hydrobromic acid or sulfunic acid, etc.) and salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid, etc.)

The compound which promotes the enzyme activity of the protein or equivalent of the present invention is useful as a safe and low-toxicity drug such as a therapeutic or prophylactic agent for hypoglycemia and so on.

The compound which inhibits the enzyme activity of the protein or equivalent of the present invention is useful as a safe and low-toxicity drug such as a therapeutic or prophylactic agent for diabetes and so on.

When the compound identified by the screening method of the present invention or by using the screening kit of the present invention is used as the therapeutic or prophylactic agent, it can be formulated to tablets, capsules, elixirs, microcapsules, aspetic solution, suspensions or the like in the same way as the pharmaceutical composition comprising the protein or equivalent of the present invention as mentioned above.

Because the thus-obtained preparation is safe and of low toxicity, it can be administered to mammals (e.g., human, rat, mouse, guinia pig, rabbit, sheep, pig, bovine, horse, cat, dog, monkey, etc.).

The dose of the compound identified by the screening method may vary depending on subject of disease, subject of administration, way of administration, and so on.

When the compound which promotes the enzyme activity of the protein or equivalent of the present invention is used, for example, for treating hypoglycemia by oral administration, the dose of the compound is normally about 0.1 to 100 mg, preferably 1.0 to 50 mg, and more preferably 1.0 to 20 mg per day for an adult (weighing 60 kg). When the compound is used, for example, for treating hypoglycemia by non-oral administration, it is advantageous to administer the compound in the form of injectable preparation at a daily dose of about 0.01 to 30 mg, preferably about 0.1 to 20 mg, and more preferably about 0.1 to 10 mg per administration by an intravenous injection for an adult (weighing 60 kg), depending on subject of administration, subject of disease and so on. For other animal species, corresponding does as converted per 60 kg weight can be administered.

When the compound which inhibits the enzyme activity of the protein or equivalent of the present invention is used, for example, for treating diabetes by oral administration, the dose of the compound is normally about 0.1 to 100 mg, preferably 1.0 to 50 mg, and more preferably 1.0 to 20 mg per day for an adult (weighing 60 kg). When the compound is used, for example, for treating diabetes by non-oral administration, it is advantageous to administer the compound in the form of injectable preparation at a daily dose of-about 0.01 to 30 mg, preferably about 0.1 to 20 mg, and more preferably about 0.1 to 10 mg per administration by an intravenous injection for an adult (weighing 60 kg), depending on subject of administration, subject of disease and so on. For other animal species, corresponding does as converted per 60 kg weight can be administered.

(6) The antisense DNA

The antisense DNA which is capable of complementary binding to the DNA or mRNA coding for the protein or equivalent of the present invention and suppresses the expression of the protein or equivalent of the present invention is capable of inhibiting the function of the protein or equivalent of the present invention or the DNA coding for the protein or equivalent of the present invention which show the above-mentioned activities in vivo. Therefore, this antisense DNA is used for a prophylactic or therapeutic agent for various diseases such as diabetes and so on.

When the antisense DNA is used for the prophylactic or therapeutic composition, it can be formulated in the same way as the prophylactic or therapeutic agent containing the DNA of the present invention and can be administered to human or mammals. The DNA may be used alone or after inserting it into a suitable vector such as retrovirus vector, adenovirus vector, adenovirus-associated virus vector, pox virus etc. followed by subjecting the product vector to a conventional means. The DNA can also be administered as "naked" DNA, with physiologically acceptable carriers such as adjuvants to assist in uptake, by "gene" gun or by a catheter such as a catheter with a hydrogel.

In addition, this antisense DNA can be used as a diagnostic oligonucleotide probe for investigating the presence of the DNA of the present invention or the status of its expression in various tissues and cells.

(7) Construction of a transgenic animal

The present invention further provides a non-human mammalian animal harboring a foreign DNA coding for the protein of the present invention (hereinafter referred to briefly as a foreign DNA) or a mutant thereof (sometimes referred to briefly as a foreign mutant DNA).

Thus, the present invention provides (i) A non-human mammalian animal harboring a foreign DNA of the present invention or a foreign mutant DNA thereof:

(ii) The non-human mammalian animal according to (i) which is a rodent:

(iii) The non-human mammalian according to (ii) wherein the rodent is a mouse or a rat; and (iv) A recombinant vector containing the foreign DNA of the present invention or a foreign mutant DNA thereof and capable of being expressed in a mammalian animal.

The non-human mammalian animal harboring the foreign DNA of the present invention or a foreign mutant DNA thereof (hereinafter referred to briefly as the transgenic animal of the present invention) can be constructed by transferring the objective DNA to a germinal cell such as an unfertilized egg cell, fertilized egg cell, or sperm cell or its primordial cell, preferably in the period of embryogenesis in the ontogenesis of a non-human mammalian animal (more preferably in the stage of a single cell or a fertilized egg cell and generally at the 8-cell stage or earlier), by the calcium phosphate method, electric pulse method, lipofection method, agglutination method, microinjection method, particle gun method, or DEAE-dextran method.

The non-human mammalian animal used includes bovines, swines, sheep, goats, rabbits, dogs, cats, guinea pigs, hamsters, mice, rats, and so on. From the standpoint of construction of a diseased animal model, rodents which have comparatively short ontogenesis and life cycles and can be easily bred, particularly mice (e.g. pure strains such as C57BL/6, DBA2, etc. and hybrid strains such as B6C3F$_1$, BDF$_1$, B6D2F$_1$, BALB/c, ICR, etc.) or rats (e.g. Wistar, S. Dak., etc.) are preferred.

The "mammalian animal" as mentioned with reference to the recombinant vector capable of being expressed in a mammalian animal includes the same non-human mammalian animals as those mentioned above and human.

The foreign DNA of the present invention is not a DNA of the present invention which is inherently harbored by the non-human mammalian animal, but a DNA of the present invention as isolated or extracted from a mammalian animal.

The mutant DNA includes not only the DNAs available upon variation (e.g. mutation) of the nucleotide sequence of the original DNA of the present invention, for example, upon addition or deletion of nucleotide sequence or substitution of other, and includes abnormal DNAs.

The term "abnormal DNA" as used herein means any DNA that causes an expression of an abnormal protein of the present invention, for example, an expression of a protein which suppresses the function of the normal protein of the present invention.

The foreign DNA of the present invention may be one derived from a mammalian animal of the same species as the host animal or a mammalian animal of a different species. For transfer of the DNA of the present invention to the host animal, it is generally advantageous to use a DNA construct prepared by linking the DNA at downstream of a promoter capable of being expressed in animal cells. For example, in transferring the human-derived DNA of the present invention, it can be linked at downstream of a promoter capable of causing expression of DNAs derived from various animals (e.g. rabbit, dog, cat, guinea pig, hamster, rat, murine, etc.) harboring the DNA of the present invention having high homology thereto to prepare a DNA construct (e.g. a vector) which can then be microinjected into the fertilized egg cell of a host mammalian animal such as a fertilized murine egg cell, whereby a transgenic mammalian animal showing a high expression of the DNA of the present invention can be provided.

Examples of the expression vector used for the protein of the present invention are plasmids derived from *E. coli*, plasmids derived from *B. subtilis,* plasmids of the yeast origin, λ phage and other bacteriophages, retroviruses such as Molony leukemia virus, and animal viruses such as vaccinia virus and vaculovirus. Preferable examples are plasmids of the *E. coli* origin, plasmids of the *B. subtilis* origin, and yeast-derived plasmids.

The promoter for the regulation of the expression of the DNA are (1) promoters for DNAs derived from viruses (e.g. simian virus, cytomegalovirus, Molony leukemia virus, JC virus, papilloma virus, poliovirus, etc.), (2) promoters derived from mammalian animals (e.g. man, rabbit, dog, cat, guinea pig, hamster, rat, mouse, etc.) and fowls (e.g. chicken) for albumin, insulin II, uroprakin II, elastase, erythropoietin, endothelin, muscle creatine kinase, glial fibrillary acidic protein, glutathione S-transferase, platelet-derived growth factor β, keratin K1, K10, and K14, collagen type I and type II, cyclic AMP-dependent protein kinase βI subunit, dystrophin, tartaric acid-resistant alkaline phosphatase, atrial natriuretic factor, endothelial receptor tyrosine kinase (generally abbreviated as Tie2), sodium/potassium-exchanging adenosine triphosphatase ($Na^+$, $K^+$-ATPase), neurofilament light chain, metallothionein I and IIA, tissue inhibitor of metalloprotease I, MHC Class I antigen (H-2L), H-ras, renin, dopamine β-hydroxylase, thyroid peroxidase (TPO), polypeptide chain elongation factor 1α (EF-1α), β actin, α- and β-myosin heavy chain, myosin light chains 1 and 2, myelin basic protein, thyroglobulin, Thy-1, immunoglobulin H chain variable region (VNP), serum amyloid P component, myoglobin, troponin C, smooth muscle α-actin, preproenkephalin A or vasopressin, and so on. Preferable promoters are promoters conductive to high expression in the whole body, such as cytomegalovirus promoter, human polypeptide chain elongation factor 1α (EF-1α) promoter, and human and chicken β-actin promoters.

The vector preferably has a sequence for terminating the transcription of the objective mRNA (generally called terminator) in the transgenic mammalian animal. The examples of the sequence are sequences derived from viruses, various mammalian animals or fowls. Preferable examples are the SV40 terminator derived from simian virus, and so on.

In addition, to enhance the expression of the objective DNA, it is possible, depending on the specific objective, to link the splicing signal, enhancer domain, a portion of the eukaryotic DNA intron, etc. at upstream of the 5'-end of the promoter region, between the promoter region and the translated region, or at downstream of the 3'-end of the translated region.

The coding region of the normal protein of the present invention can be acquired, as the whole or part of the genomic DNA, from the DNAs derived from the liver, kidney, or thyroid cells or fibroblasts of various mammals (e.g. rabbit, dog, cat, guinea pig, hamster, rat, murine, man, etc.) or from various commercially available genomic DNA libraries, or starting with the complementary DNAs prepared from mRNAs derived from the liver, kidney, thyroid cells or fibroblasts by the known technique. The foreign abnormal DNA can be constructed by mutating the coding region of the normal protein of the present invention available from the above-mentioned cells or tissues by the point mutation method.

The coding region can be prepared as a DNA construct which can be expressed in a transgenic animal, by the general recombinant DNA technique, i.e. by coupling it at downstream of the promoter and, if desired, at upstream of the transcription termination site.

Transfering the DNA of the present invention at the fertilized egg cell stage, the DNA can be ubiquitous in all the germ cells and somatic cells of the host mammalian animal. The presence of the DNA of the present invention in the germ cells of the transgenic animal following DNA transfer means that all the germ cells and somatic cells of all the progeny of the transgenic animal harbor the DNA of the present invention. Thus, the offspring of animals of this line to which DNA is passed down have the DNA of the present invention in their germ cells and somatic cells.

The non-human mammalian animal to which the foreign normal DNA of the present invention has been transferred can be verified by mating to retain the DNA stably and then bred as a strain harboring the transferred DNA from generation to generation under the usual breeding conditions. The transfer of the DNA of the present invention in the fertilized egg cell stage is carried out in such a manner that the transferred DNA will be present in excess in all the germ cells and somatic cells of the transgenic animal. The presence of an excess of the DNA of the present invention in the germ cells of the transgenic animal means that all the progeny of this line harbor an excess of the DNA of the present invention in their germ cells and somatic cells. By acquiring homozygous animals having the transferred DNA in both homologous chromosomes and mating the animals of both sexes, they can be bred serially so that all the progeny may harbor an excess of the DNA.

The non-human mammalian animal harboring the normal DNA of the present invention features a high expression of the DNA and may eventually develop a hyperergasia of the protein of the present invention through activation of the function of the endogenous normal DNA and, therefore, can be utilized as an animal model of the disease. For example, by using the transgenic animal harboring the normal DNA of the present invention, it is possible to study the hyperergasia of the protein of the present invention to elucidate the mechanisms of diseases with which the protein of the present invention is associated, and explore therapeutic modalities for the diseases.

Furthermore, the mammalian animal to which the foreign normal DNA of the present invention has been transferred presents with symptoms due to an increase in the free protein of the present invention and, therefore, can also be used in the screening of therapeutic drugs for diseases with which the protein of the present invention is associated.

On the other hand, the non-human mammalian animal harboring the foreign abnormal DNA of the present invention can be verified by mating to retain the DNA stably and then bred as a line harboring the DNA from generation to generation under the usual breeding conditions. Moreover, it is possible to incorporate the objective DNA in the above-mentioned plasmid for use as a starting material. The DNA construct with the promoter can be prepared by the general recombinant DNA technique. Transfering the abnormal DNA of the present invention in the fertilized egg cell stage, the transferred DNA can be ubiquitous in all the germ cells and somatic cells of the host mammalian animal. The presence of the abnormal DNA of the present invention in the germ cells of the transgenic animal means that all the offspring of this transgenic animal harbor the abnormal DNA of the present invention in all of their germ cells and somatic cells. The progeny of this animal harbor the abnormal DNA of the present invention in all of their germ cells and somatic cells. By acquiring homozygous male and female animals having the introduced DNA in both homologous chromosomes and mating them, it can be insured that all their offsprings harbor the DNA.

The non-human mammalian animal harboring the abnormal DNA of the present invention features a high expression of the abnormal DNA and, therefore, may eventually develop adiaphoria associated with functional inactivation of the protein of the present invention through inhibition of the function of the endogenous normal DNA and, therefore, can be utilized as an animal model of the disease. For example, by using the transgenic animal harboring the abnormal DNA of the present invention, analysis of the mechanism of this functional inactivation adiaphoria due to the protein of the present invention and therapeutic modalities for the disease can be explored.

As a specific potential use, the transgenic animal with a high expression of the abnormal DNA of the present invention can be used as a model for elucidating the functional inhibition of the normal protein by the abnormal protein of the present invention (dominant negative effect) in adiaphoria of functional inactivation type due to the protein of the present invention. Moreover, the transgenic mammalian animal harboring the foreign abnormal DNA of the present invention develops symptoms due to an increase in the free protein of the present invention and, therefore, can be utilized in the screening for therapeutic compounds for adiaphoria due to functional inactivation of the protein of the present invention.

As other potential uses for transgenic animals harboring the two kinds of DNAs described above, the following uses can be suggested.

(a) Use as a cell source for tissue culture;
(b) Analysis of the relationship of the protein of the present invention to proteins which are specifically expressed or activated by the protein by direct analysis of DNAs or RNAs in the tissues of the transgenic mammalian animal harboring the DNA of the present invention or analysis of the composition of the protein expressed by the DNA;
(c) Study of the functions of cells established from tissues which are generally difficult to culture in the standard tissue culture technique by introducing the DNA into them;
(d) Screening of drugs capable of enhancing the cell functions by using the cells described in (3);
(e) Isolation and purification of the muteins of the present invention and construction of antibodies to the muteins.

Furthermore, by using the transgenic animal of the present invention, clinical symptoms of diseases associated with the protein of the present invention, inclusive of said adiaphoria associated with functional inactivation of the protein of the present invention, can be investigated. In addition, more detailed pathological findings can be generated in various organs of this model of diseases associated with the protein of the present invention, thus contributing to the development of new therapies and the study and treatment of secondary diseases arising from such diseases.

Moreover, following isolation of various organs from the transgenic animal of the present invention and their mincing and digestion with a proteolytic enzyme such as trypsin, free single cells harboring the transferred gene can be recovered and cultured for establishment of a cell line. Furthermore, characterization of cells producing the protein of the present invention can be made and their relationship to glucose metabolism, or the mechanism of signal transduction in it, and abnormalities involved can be explored to thereby generate information useful for a further elucidation of the protein of the present invention and its actions.

Moreover, for the development of therapeutic drugs for diseases associated with the protein of the present invention, such as adiaphoria due to functional inactivation of the protein of the present invention by using the transgenic animal of the present invention, an effective and rapid screening technology for such therapeutic drugs can be established by using the test and assay methods described hereinbefore. In addition, by using the above transgenic animal or the foreign DNA expression vector of the present invention, gene therapies for diseases associated with the protein of the present invention can be explored and developed.

(8) Construction of knockout animals

The present invention further provides a non-human mammalian embryonic stem cell wherein the DNA of the present invention is inactivated and a non-human mammalian animal deficient in expression of the DNA of the present invention wherein the DNA is inactivated.

The present invention, therefore, provides:

(i) A non-human mammalian embryonic stem cell wherein the DNA of the present invention is inactivated;
(ii) The non-human mammalian embryonic stem cell according to in (i) wherein the DNA is inactivated by introducing a reporter gene (e.g. a β-galactosidase gene of the E. coli origin);
(iii) The non-human mammalian embryonic stem cell according to (i) which is neomycin-resistant;
(iv) The non-human mammalian embryonic stem cell according to (i) wherein the non-human mammalian animal is a rodent;
(v) The non-human mammalian embryonic stem cell according to (iv) wherein the rodent is a mouse;
(vi) A non-human mammalian animal deficient in expression of the DNA of the present invention, wherein the DNA is inactivated;
(vii) The non-human mammalian animal according to (vi) wherein the DNA is inactivated by introducing a reporter gene (e.g. a β-galactosidase gene of E. coli origin) and the reporter gene can be expressed under the control of the promoter against the DNA of the present invention;
(viii) The non-human mammalian animal according to (vi) wherein the non-human mammalian animal is a rodent;,
(ix) The non-human mammalian animal according to (viii) wherein the rodent is a mouse; and
(x) A method for screening for a compound or a salt thereof which enhances or inhibits an activity the promoter against the DNA of the present invention, which comprises administering a test compound to the non-human mammalian animal according to (vii) and detecting an expression of the reporter gene.

The term "non-human mammalian embryonic stem cell wherein the DNA of the present invention is inactivated" means the embryonic stem cell (hereinafter referred to briefly as ES cell) of a non-human mammalian animal in which the DNA has been deprived of the capacity to express the protein of the present invention (hereinafter referred to sometimes as the knockout DNA of the present invention) through introduction of an artificial mutation to the DNA of the present invention possessed by the non-human mammalian animal to thereby inhibit expression of the DNA of the present invention or through substantial deprivation of the activity of the protein of the present invention which is encoded by the DNA.

The non-human mammalian animal includes the same animals mentioned hereinbefore.

Examples of the method for introducing an artificial mutation to the DNA of the present invention are a deletion of some or all of the DNA sequence, or an insertion or substitution of a different DNA by the genetic engineering technology. By such a mutation, the codon reading frame can be shifted or the function of the promoter or exon can be disrupted to provide the knockout DNA of the present invention.

The non-human mammalian embryonic stem cell wherein the DNA of the present invention is inactivated (hereinafter referred to as the ES cell wherein the DNA of the present invention is inactivated or the knockout ES cell of the present invention) can be acquired by, for example, a procedure which comprises isolating the DNA of the present invention from an objective non-human mammalian animal, inserting a drug-resistance gene, typically the neomycin-resistance gene or hygromycin-resistance gene, or a reporter gene such as lacZ (β-galactosidase gene) or cat (chloramphenicol acetyltransferase gene) in its exon region to disrupt the function of the exon or inserting a DNA sequence for terminating gene transcription (e.g. poly A coupling signal) in the intron region between exons to thereby inhibit synthesis of a complete mRNA, introducing the thus-constructed DNA chain having a DNA sequence adapted to eventually disrupt the gene (hereinafter referred to briefly as the targeting vector) into the chromosomes of the host animal by homologous recombination technique, subjecting the resulting ES cell to Southern hybridization analysis using the DNA sequence on the DNA of the present invention or in its vicinity as the probe or a PCR procedure using the DNA sequence on the targeting vector and a DNA sequence in the vicinity but not including the DNA of the present invention used in the construction of the targeting vector as primers, and selecting the knockout ES cell of the present invention.

Moreover, the original ES cell used for inactivation of the DNA of the present invention by the homologous recombination technique or the like may be an already established cell line such as those mentioned hereinbefore or a new cell line established de novo by the known method of Evans and Kaufma. Taking, murine ES cells as an example, ES cells of the 129 line are generally employed but the immunological background of this line is not clear. Therefore, the cell line established by using $BDF_1$ mice, which is created by the hybridization of C57BL/6 mice, yielding few eggs, with DBA/2 mice ($BDF_1=F_1$ of C57BL/6 and DBA/2) for acquiring pure-line ES cells with an immunologically defined genetic background can be used with advantage. In addition to the advantage of high egg output and-sturdiness of the egg, BDF, mice have the background of C57BL/6 mice so that in the construction of a disease model with ES cells obtained, the genetic background of the model mice can be converted to that of C57BL/6 mice by back-crossing with C57BL/6.

Moreover, in establishing an ES cell line, it is common practice to use blastocytes 3.5 days following fertilization but, aside from them, a large number of early embryos can be acquired with high efficiency by harvesting the embryos at the 8-cell stage and culturing them into blastocytes.

Furthermore, while ES cells from both male and female animals can be employed, generally ES cells of a male animal are more convenient for the construction of reproduction line chimeras. Moreover, for the purpose of reducing the burden of the complicated cultural procedure, it is preferable to carry out sexing as early as possible.

As a typical method for sexing ES cells, there can be mentioned the method in which the gene in the sex determination region on the Y chromosome is amplified and detected by PCR. Whereas the conventional karyotype analysis requires about $10^6$ cells, the above method requires only about one colony equivalent of ES cells (about 50 cells). Therefore, the primary selection of ES cells in an early stage can be made by this sexing method. Since male cells can thus be selected in the early stage, the trouble in the initial stage of culture can be drastically reduced.

Moreover, the secondary selection can be carried out by G-banding for the number of chromosomes. The number of chromosomes in the resulting ES cell is preferably 100% of the normal number but this goal may not be reached due to the physical and other factors involved in the establishment of the line. In such cases, it is preferable to knockout the gene of the ES cell and reclone it in the normal cell (taking a mouse as an example, the cell in which the number of chromosomes is 2n=40).

The embryonic stem cell line thus established is generally very satisfactory in proliferation characteristic but since it is liable to lose its ontogenic ability, it must be subcultured with sufficient care. For example, this cell line should be cultured on suitable feeder cells such as STO fibroblasts in the presence of LIF (1–10000 U/ml) in a carbon dioxide incubator (preferably 5% $CO_2$-95% air or 5% oxygen-5% $CO_2$-90% air) at about 37° C. and, in subculture, it should be treated with trypsin/EDTA solution (generally 0.001–0.5% trypsin/0.1–5 mM EDTA, preferably about 0.1% trypsin/1 mM EDTA) to provide single cells and seed them on freshly prepared feeder cells. While such subculture is generally performed every 1–3 days, it is good practice to observe the cells on each occasion and, whenever morphologically abnormal cells are discovered, discard the culture.

ES cells can be allowed to differentiate into various types of cells, such as head long muscle cells, visceral muscle cells, heart muscle cells, etc. by conducting monolayer culture to a high density under suitable conditions or suspension culture until a mass of cells is formed (M. J. Evans & M. H. Kaufman, Nature, 292, 154 (1981); G. R. Martin, Proc. Natl. Acad. Sci. U.S.A., 78, 7634 (1981); T. C. Doetschman et al., Journal of Embryology and Experimental Morphology, 87, 27 (1985)), and the cell deficient in expression of the DNA of the present invention differentiated from the ES cell of the present invention is useful for investigating the biological role of the protein of the present invention.

The non-human mammalian animal deficient in expression of the DNA of the present invention can be distinguished from the normal animal by measuring the amount of mRNA in both animals by the known method and comparing them indirectly.

The non-human mammalian animal used for this purpose includes the animals mentioned hereinbefore.

Referring to the non-human mammalian animal deficient in expression of the DNA of the present invention, the DNA of the present invention can be knocked out by introducing the targeting vector constructed as above into, for example, a murine embryonic stem cell or a murine egg cell and thereby causing the DNA sequence of the targeting vector harboring the inactivated DNA of the present invention to undergo homologous recombination with, and accordingly replacing, the DNA of the present invention on the murine embryonic stem cell or egg cell chromosomes.

The cell with the DNA of the present invention thus knocked out can be identified by Southern hybridization analysis using a DNA sequence on the DNA of the present invention or in its vicinity as a probe or by PCR using a DNA sequence on the targeting vector or a murine-derived DNA sequence in a region adjacent to but not including the DNA of the present invention used in the targeting vector as primers. When a non-human mammalian embryonic stem cell is used, a cell line with the DNA of the present invention knocked out by the homologous recombination technique is cloned and injected into the non-human mammalian embryo or blastocyte at a suitable stage of embryogenesis, for example at the 8-cell stage, and the resulting chimera embryo is transplanted in the pseudopregnant uterus of the non-human mammalian animal. The animal thus obtained is a chimera animal constituted by both of the cells harboring the normal DNA of the present invention and the cells harboring the artificially mutated DNA of the present invention.

When some of the gametes of this chemira animal harbor the mutated DNA of the present invention, an individual of which the entire tissues are constituted by cells harboring the mutated DNA of the present invention can be screened from the colony of animals obtained by crossing such a chimera animal with a normal animal, for example, by coat color discrimination. The individuals thus selected are usually animals deficient in hetero-expression of the protein of the present invention and by mating such individuals deficient in hetero-expression of the protein of the present invention with each other, animals deficient in homo-expression of the protein of the present invention can be acquired.

When an egg cell is used, a transgenic non-human mammalian animal with the targeting vector having been introduced into its chromosomes can be acquired by injecting the DNA solution into the egg cell nucleus by the microinjection technique and selecting animals expressing a mutation of the DNA of the present invention by homologous recombination.

The individuals with the DNA of the present invention knocked out are mated to verify that the animals acquired by mating also have the DNA knocked out and they can be sub-bred under the usual breeding conditions.

Acquisition and maintenance of the reproduction line can also be carried out in the routine manner. Thus, by mating male and female animals harboring the inactivated DNA, homozygotes having the inactivated DNA in both homologous chromosomes can be obtained. The homozygotes thus obtained are bred under such conditions that, with regard to the dam, the number of homozygotes is plural per normal individual. By mating male and female heterozygotes, homozygotes and heterozygotes both harboring the inactivated DNA can be sub-bread.

The non-human mammalian embryonic stem cell harboring the inactivated DNA of the present invention is very useful for the construction of non-human mammalian animals deficient in expression of the DNA of the present invention. Moreover, the mouse deficient in expression of the protein of the present invention lacks the various biological activities inducible by the protein of the present invention and can, therefore, be of use as an animal model of diseases arising from inactivation of the biological activities of the protein of the present invention, thus being of use in the etiological studies of diseases and development of therapeutics.

(8a) A method for screening for a compound having therapeutic or prophylactic effect in the various diseases caused by a defect in or a damage to the DNA of the present invention A non-human mammalian animal deficient in expression of the DNA of the present invention can be used in the screening for a compound having therapeutic or prophylactic effect in the diseases (e.g. hypoglycemia) caused by a defect in or a damage to the DNA of the present invention.

Thus, the present invention provides a method for screening for a compound, or a salt thereof, which has therapeutic or prophylactic effect in the diseases caused by a defect in or a damage to the DNA of the present invention, which method comprises administering a test compound to a non-human mammalian animal deffcient in expression of the DNA of the present invention and monitoring or measuring a change of the non-human mammalian animal.

The non-human mammalian animal deficient in expression of the DNA of the present invention, which is to be used in this screening method, includes the same animals as those mentioned above.

The test compound includes peptides, proteins, non-peptide compounds, synthetic compounds, fermentation products, cell extracts, plant extracts, animal tissue extracts, blood plasma and so on. The test compound may be novel or known compounds.

More specifically, a non-human mammalian animal deficient in expression of the DNA of the present invention is treated with the test compound and the treated animal is compared with an untreated control to evaluate the test compound for therapeutic or prophylactic effect by determining a change in some organ or tissue or in a disease symptom as an indicator.

The method of treating a test animal with a test compound can be selected according to the symptom or symptoms manifested by the test animal and the characteristics of the test compound, among other factors and, for example, oral administration or intravenous injection can be employed. The dosage of the test compound can be suitably selected according to the route of administration, the properties of the test compound, and other conditions.

In the screening for a compound with therapeutic or prophylactic efficacy in hypoglycemia, for instance, non-human mammalian animals showing insufficient expression of the DNA of the present invention are subjected to sugar loading. The test compound is administered before or after sugar loading and changes in blood glucose level, body weight, etc. in the animal are determined at timed intervals.

When, in said screening method, the blood sugar level in the test animal is increased about 10% or more, preferably about 30% or more, more preferably about 50% or more, following administration of the test compound, the particular test compound can be selected as a compound capable of producing therapeutic or prophylactic efficacy in hypoglycemia.

The compound obtained by the above screening method has therapeutic or prophylactic effect in the diseases (e.g. hypoglycemia) caused by a defect in or a damage to the protein, etc. of the present invention and, therefore, can be used as a drug, for example, as a safe, low-toxicity therapeutic or prophylactic agent for the diseases. Furthermore, compounds derived from the compound identified by the above screening may also be used in the same manner.

The salts of the compound obtained by the screening method as mentioned above includes salts with physiologically acceptable bases (e.g. alkali metals) or acids such as organic or inorganic acids, and is preferably a physiologically acceptable acid addition salt. Examples of such salts are salts thereof with inorganic acids (e.g. hydrochloric acid, phosphoric acid, hydrobromic acid or sulfunic acid, etc.) and salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid, etc.)

The therapeutic or prophylactic agent comprising the compound identified by the screening method can be prepared in the same as the pharmaceutical composition comprising the protein or equivalent of the present invention as mentioned above.

Because the thus-obtained preparation is safe and of low toxicity, it can be administered to mammals (e.g., human, rat, mouse, guinia pig, rabbit, sheep, pig, bovine, horse, cat, dog, monkey, etc.).

The dose of the compound may vary depending on subject disease, subject of administration, way of administration, and so on. When the compound is used, for example, for treating hypoglycemia by oral administration, the dose of the compound is normally about 0.1 to 100 mg, preferably 1.0 to 50 mg, and more preferably 1.0 to 20 mg per day for an adult (weighing 60 kg). When the compound is used, for example, for treating hypoglycemia by non-oral administration, it is advantageous to administer the compound in the form of injectable preparation at a daily dose of about 0.01 to 30 mg, preferably about 0.1 to 20 mg, and more preferably about 0.1 to 10 mg per administration by an intravenous injection for an adult (weighing 60 kg), depending on subject of administration, subject disease and so on. For other animal species, corresponding dose as converted per 60 kg weight can be administered.

(8b) A method for screening for a compound capable of promoting or inhibiting an activity of the promoter for the DNA of the present invention The present invention provides a method for screening for a compound, or a salt thereof, which promotes or inhibits an activity of the promoter for the DNA of the present invention, which method comprises administering a test compound to a non-human mammalian animal deficient in expression of the DNA of the present invention, wherein the DNA of the present invention is inactivated by introducing of a reporter gene and detecting the expression of the reporter gene.

As the test compound, the same compounds as those mentioned hereinbefore can be used.

Examples of the reporter gene are the same genes as those mentioned hereinbefore. Preferable examples are a β-galactosidase gene (lacZ) and so on.

In non-human mammalian animals deficient in expression of the DNA of the present invention, which is inactivated by introducing a reporter gene, the reporter gene is under the control of the promoter for the DNA of the present invention and, therefore, the activity of the promoter can be detected by tracing the expression of the protein encoded by the reporter gene.

For instance, when part of the DNA coding for the protein of the present present invention has been inactivated by the E. coli-derived β-galactosidase gene (lacZ), β-galactosidase is expressed in those tissues where the protein of the present invention would have been expressed. Therefore, the status of expression of the protein of the present invention in a living animal body can be traced, easily and expediently, for example, by the staining method using a reagent serving as a substrate for β-galactosidase, such as 5-bromo-4-chloro-3-indolyl-β-galactopyranoside (X-gal). More specifically, a mouse defective in the protein of the present invention or a tissue section thereof is fixed with glutaraldehyde or the like, washed with Dulbecco's phosphate-buffered saline (DPBS), and reacted with a staining solution containing X-gal at room temperature or around 37° C. for about 30 minutes to 1 hour. The tissue sample is then washed with 1 mM EDTA/PBS solution to terminate the β-galactosidase reaction and observed for color development. Alternatively, the mRNA coding for lacZ may be detected by a conventional method.

The compound, or a salt thereof, obtained by the above screening method is a compound selected from among the test compounds mentioned above and, as such, is a compound capable of promoting or inhibiting the activity of the promoter for the DNA of the present invention.

The salts of the compound identified by the screening method as mentioned above includes salts with physiologically acceptable bases (e.g. alkali metals) or acids such as organic or inorganic acids, and is preferably a physiologically acceptable acid addition salt. Examples of such salts are salts thereof with inorganic acids (e.g. hydrochloric acid, phosphoric acid, hydrobromic acid or sulfuric acid, etc.) and salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid, etc.)

The compound, or a salt thereof, which promotes the activity of the promoter for the DNA of the present invention is capable of promoting the expression of the protein of the present invention and, hence, the promoting function of the protein. Therefore, the compound is useful as a drug, such as a safe, low-toxicity therapeutic or prophylactic agent for diseases such as hypoglycemia and so on.

On the other hand, the compound, or a salt thereof, which inhibits the activity of the promoter for the DNA of the present invention is capable of inhibiting expression of the protein of the present invention and, hence, inhibiting the function of the protein. Therefore, the compound is useful as a drug, such as a safe, low-toxicity therapeutic or prophylactic agent for diseases such as diabetes and so on.

Furthermore, compounds derived from the compound obtained by the above screening method may also be used in the same way.

The therapeutic or prophylactic agent comprising the compound identified the screening method can be prepared in the same as the pharmaceutical composition comprising the protein or equivalent of the present invention as mentioned above.

Because the thus-obtained preparation is safe and of low toxicity, it can be administered to mammals (e.g., human, rat, mouse, guinia pig, rabbit, sheep, pig, bovine, horse, cat, dog, monkey, etc.).

The dose of the compound may vary depending on subject disease, subject of administration, way of administration, and so on. When the compound which promotes an activity of the promoter is used, for example, for treating hypoglycemia by oral administration, the dose of the compound which promotes the activity of the promoter is normally about 0.1 to 100 mg, preferably 1.0 to 50 mg, and more preferably 1.0 to 20 mg per day for an adult (weighing 60 kg). When the compound which promotes the activity of the promoter is used, for example, for treating hypoglycemia by non-oral administration, it is advantageous to administer the compound which promotes the activity of the promoter in the form of injectable preparation at a daily dose of about 0.01 to 30 mg, preferably about 0.1 to 20 mg, and more preferably about 0.1 to 10 mg per administration by an intravenous injection for an adult (weighing 60 kg), depending on subject of administration, subject disease and so on. For other animal species, corresponding dose as converted per 60 kg weight can be administered.

When the compound which inhibits the activity of the promoter is used, for example, for treating diabetes by oral administration, the dose of the compound which inhibits the activity of the promoter is normally about 0.1 to 100 mg, preferably 1.0 to 50 mg, and more preferably 1.0 to 20 mg per day for an adult (weighing 60 kg). When the compound which inhibits the activity of the promoter is used, for example, for treating diabetes by non-oral administration, it is advantageous to administer the compound which inhibits the activity of the promoter in the form of injectable preparation at a daily dose of about 0.01 to 30 mg, preferably about 0.1 to 20 mg, and more preferably about 0.1 to 10 mg per administration by an intravenous injection for an adult (weighing 60 kg), depending on subject of administration, subject disease and so on. For other animal species, corresponding dose as converted per 60 kg weight can be administered.

In the specification and drawings of the present application, the abbreviations used for bases (nucleotides), amino acids and so forth are those recommended by the IUPAC-IUB Commission on Biochemical Nomenclature or those conventionally used in the art. Examples thereof are given below. Amino acids for which optical isomerism is possible are, unless otherwise specified, in the L form.

DNA: Deoxyribonucleic acid
cDNA: Complementary deoxyribonucleic acid
A: Adenine
T: Thymine
G: Guanine
C: Cytosine
RNA: Ribonucleic acid
mRNA: Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediaminetetracetic acid
SDS: Sodium dodecyl sulfate
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine
pGlu: Pyroglutamic acid Substitution groups, protecting groups and reagents used in the specification of the present application are represented by the symbols set forth below.
Me: Methyl
Et: Ethyl
Bu: Butyl
Ph: Phenyl
TC: Thiazolidine-4(R)-carboxamide
Tos: p-toluene sulfonyl
CHO: Formyl
Bzl: Benzyl
Cl$_2$-Bzl: 2,6-dichlorobenzyl
Bom: Benzyloxymethyl
Z: Benzyloxycarbonyl
Cl-Z: 2-chlorobenzyloxycarbonyl
Br-Z: 2-bromobenzyloxycarbonyl
Boc: Tert-butoxycarbonyl
DNP: Dinitrophenyl
Trt: Trityl
Bum: Tert-butoxymethyl
Fmoc: N-9-fluorenylmethyloxycarbonyl
HOBt: 1-hydroxybenzotriazole
HOOBt: 3,4-dihydro-3-hydroxy-4-oxo-1,2,3-benzotriazine
HONB: 1-hydroxy-5-norbornene-2,3-dicarboximide
DCC: Dicyclohexylcarbodiimide SEQ ID NO:1 shows a partial amino acid sequence common to the proteins: TGC028-3 and TGC028-4 of the present invention.

SEQ ID NO:2 shows an amino acid sequence of the protein: TGC028-3 of the present invention.

SEQ ID NO:3 shows an amino acid sequence of the protein: TGC028-4 of the present invention.

SEQ ID NO:4 shows a nucleotide sequence of a DNA coding for the amino acid sequence represented by SEQ ID NO:1.

SEQ ID NO:5 shows a nucleotide sequence of a DNA coding for the protein: TGC028-3 of the present invention which has the amino acid sequence represented by SEQ ID NO:2.

SEQ ID NO:6 shows a nucleotide sequence of a DNA coding for the protein: TGC028-4 of the present invention which has the amino acid sequence represented by SEQ ID NO:3.

SEQ ID NO:7 shows a partial amino acid sequence common to the proteins: TGC028-3 and TGC028-4 of the present invention which corresponds to the amino acid sequence from the 1st to 149th amino acid residue in the sequence represented by SEQ ID NO:1.

SEQ ID NO:8 shows a partial amino acid sequence common to the proteins: TGC028-3 and TGC028-4 of the present invention which corresponds to the amino acid sequence from the 150th to 270th amino acid residues in the sequence represented by SEQ ID NO:1.

SEQ ID NO:9 shows a partial amino acid sequence common to the proteins: TGC028-3 and TGC028-4 of the present invention which corresponds to the amino acid sequence from the 271th to 425th amino acid residues in the sequence represented by SEQ ID NO:1.

SEQ ID NO:10 shows a nucleotide sequence of a DNA coding for the partial amino acid sequence represented by SEQ ID NO:7.

SEQ ID NO:11 shows a nucleotide sequence of a DNA coding for the partial amino acid sequence represented by SEQ ID NO:8.

SEQ ID NO:12 shows a nucleotide sequence of a DNA coding for the partial amino acid sequence represented by SEQ ID NO:9.

SEQ ID NO:13 shows a nucleotide sequence of the probe used in Reference Example 1 for cloning a DNA coding for the protein: TGC028-2.

SEQ ID NO:14 shows a nucleotide sequence of the probe used in Reference Example 1 for cloning a DNA coding for the protein: TGC028-2 and in Example 1 for cloning a DNA coding for the protein: TGC028-3 of the present invention.

SEQ ID NO:15 shows a nucleotide sequence of the probe used in Reference Example 1 for cloning a DNA coding for the protein: TGC028-2 and in Example 1 for cloning a DNA coding for the protein: TGC028-3 of the present invention.

SEQ ID NO:16 shows a nucleotide sequence of the probe used in Example 1 for cloning a DNA coding for the protein: TGC028-3 of the present invention.

SEQ ID NO:17 shows a nucleotide sequence of the probe used in Example 3 for performing Northern blotting for a DNA coding for the protein: TGC028-3 of the present invention.

SEQ ID NO:18 shows an amino acid sequence of the protein: TGC028-2.

SEQ ID NO:19 shows a nucleotide sequence of a DNA coding for the amino acid sequence represented by SEQ ID NO:18.

SEQ ID NO:20 shows a nucleotide sequence of a synthetic oligonucleotide used for the construction of the expression vector of the protein: TGC028-3 of the present invention in Example 4.

SEQ ID NO:21 shows a nucleotide sequence of a synthetic oligonucleotide used for the construction of the expression vector of the protein: TGC028-3 of the present invention in Example 4.

SEQ ID NO:22 shows a nucleotide sequence of a synthetic oligonucleotide used for the construction of the expression vector of the protein: TGC028-3 of the present invention in Example 4.

SEQ ID NO:23 shows a nucleotide sequence of a synthetic oligonucleotide used for the construction of the expression vector of the protein: TGC028-3 of the present invention in Example 4.

SEQ ID NO:24 shows a nucleotide sequence of a synthetic oligonucleotide used for the construction of the expression vector of the protein: TGC028-4 of the present invention in Example 4.

SEQ ID NO:25 shows a nucleotide sequence of a synthetic oligonucleotide used for the construction of the expression vector of the protein: TGC028-4 of the present invention in Example 4.

The transformant strain of *Escherichia coli*, designated DH10B/pTB1942, which is obtained in the Reference Example 1 mentioned hereinafter, are on deposit under the terms of the Budapest Treaty from Aug. 9, 1996, with the NIBH under the Accession Number of FERM BP-5621. They are also on deposit from Aug. 8, 1996 with the IFO under the Accession Number of IFO 16003.

The transformant strain of *Escherichia coli*, designated DH10B/pTB1943, which is obtained in the Example 1 mentioned hereinafter, is on deposit under the terms of the Budapest Treaty from Aug. 9, 1996, with the NIBH under the Accession Number of FERM BP-5622. It is also on deposit from Aug. 8, 1996 with the IFO under the Accession Number of IFO 16004.

The transformant strain of *Escherichia coli*, designated DH10B/pTB1944, which is obtained in the Example 2 mentioned hereinafter, is on deposit under the terms of the Budapest Treaty from Aug. 9, 1996, with the NIBH under the Accession Number of FERM BP-5623. It is also on deposit from Aug. 8, 1996 with the IFO under the Accession Number of IFO 16005.

BRIEF DESCRIPTION OF THE DRAWINGS

FIGS. 1A–1F shows a nucleotide sequence of the DNA coding for the protein: TGC028-3 of the present invention as obtained in Example 1 as well as the amino acid sequence encoded thereby.

FIGS. 2A–2F shows a nucleotide sequence of the DNA coding for the protein: TGC028-4 of the present invention as obtained in Example 2 as well as the amino acid sequence encoded thereby.

FIGS. 3A–3D shows a nucleotide sequence of the DNA coding for the protein: TGC028-2 as obtained in Reference Example 1 as well as the amino acid sequence encoded thereby.

BEST MODE FOR CARRYING OUT THE PRESENT INVENTION

EXAMPLES

Figure 4:
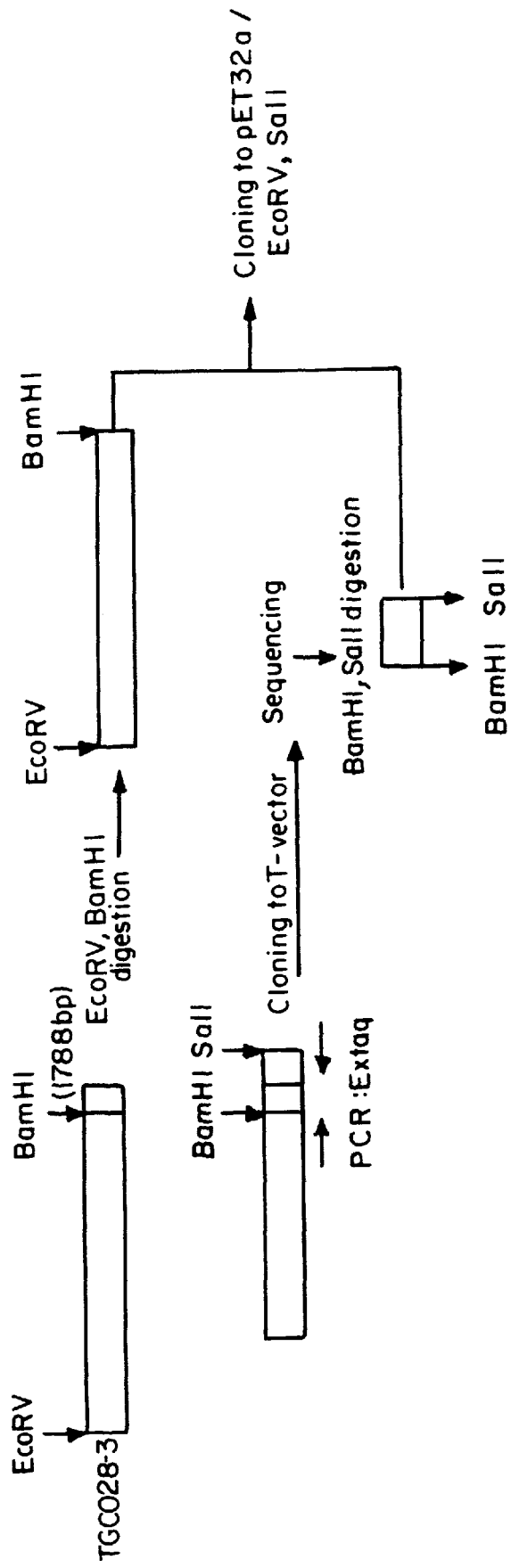
FIG. 4 shows a construction scheme of the plasmid pTB1944 containing the DNA coding for the protein: TGC028-4 of the present invention.

The following examples are intended to describe the present invention in further detail and should by no means be interpreted as defining the scope of the present invention. The gene manipulation using *Escherichia coli* was carried out in accordance with the procedure described in Molecular Cloning 2nd (J. Sambrook et al., Cold Spring Harbor Lab. Press, 1989).

Reference Example 1 Cloning of a gene coding for a novel protein: TGC028-2

Cloning of the cDNA encoding a novel protein: TGC028-2 was performed using the GENETRAPPER™ cDNA Positive Selection System (GIBCO BRL).

The *Escherichia coli* DH12S cells harboring SUPERSCRIPT™ human brain cDNA library (GIBCO BRL) was cultured in terrific broth (12 g/L Bacto-tryptone (Difco), 24 g/L Bacto yeast extract (Difco), 2.3 g/L monopotassium phosphate, 12.5 g/L dipotassium phosphate, 4% glycerol) containing 100 μg/ml ampicillin at 30° C. for 16 hours, and the plasmid cDNA library was extracted and purified using a QIAGEN Plasmid Kit (QIAGEN). The purified plasmid cDNA library was digested with Gene II and ExoIII (each from GIBCO BRL) to give the single-stranded cDNA library.

On the other hand, a synthetic oligonucleotide (SEQ ID NO:13) was used as a probe for screening a positive cDNA clone. The probe was biotinylated at the 3'-end by using TdT and biotin-14-dCTP (GIBCO BRL). The single-stranded cDNA library was treated at 95° C. for 1 minute, chilled on ice, and hybridized with the biotinylated probe at 37° C. for 1 hour. After the hybridization, MPG®-streptavidin beads (GIBCO BRL) were added to the reaction tube and the tube was incubated at room temperature for 30 minutes, with stirring at 2-minute intervals. Then, the tube was inserted into a GIBCO BRL Magna-Sep™ Magnetic Particle Separator (GIBCO BRL) and allowed to stand for 2 minutes. After the supernatant was discarded, the magnet beads were resuspended in 100 μl of wash buffer and the supernatant was removed and discarded. This washing was performed three times. Then, the tube was placed in the magnet separator and allowed to stand fpr 5 min. After the supernatant was discarded, the magnet beads were resuspended in elution buffer was added, incubated at room temperature for 5 minutes, and the supernatant DNA solution was recovered.

To the thus-obtained DNA solution was added the synthetic oligonucleotide (SEQ ID NO:13) as a primer. After the mixture was incubated at 95° C. for 1 minute, 15 μl of the prewarmed repair mixture containing 10 mM dNTP mix, repair buffer and repair enzyme was added to the mixture and the mixture was incubated at 70° C. for 15 minutes for repaining the captured DNA. The thus-obtained double-stranded DNA was introduced into the *Escherichia coli* DH10B cells by an electroporation apparatus (Bio-Rad).

The thus-obtained transformants were screened by the colony PCR technique using two oligonucleotides (SEQ ID NO:14 and SEQ ID NO:15) as primers. One colony which formed a PCR-amplified 612 bp fragment was selected as a positive clone.

The *Escherichia coli* strain thus selected was cultured, DNA was extracted therefrom and subjected to reaction using a Taq Dideoxy Terminator Cycle Sequencing Kit (Perkin-Elmer) and the nucleotide sequence of the cDNA was determined using a model 373A DNA sequencer (Perkin-Elmer). The insert DNA of the plasmid obtained from the clone contained a poly(A)$^+$ chain and had the 1458 nucleotide sequence of SEQ ID NO:19 (FIG. 3). This DNA fragment was found encoding a novel protein: TGC028-2, composed of 486 amino acid residues represented by SEQ ID NO:18, and the predicted gene product had 68% homology with the human GFAT at the amino acid level.

The plasmid pTB1942 containing the DNA coding for the protein: TGC028-2 was introduced into *Escherichia coli* DH10B to provide a transformant: *Escherichia coli* DH10B/pTB1942.

Example 1

Cloning of a gene coding for the novel protein: TGC028-3

Cloning of the cDNA encoding the novel protein: TGC028-3 was performed using the GENETRAPPER™ cDNA Positive Selection System (GIBCO BRL).

The *Escherichia coli* DH12S cells harboring a human brain-derived cDNA library (GIBCO BRL) was cultured in terrific broth (12 g/L Bacto-tryptone (Difco), 24 g/L Bacto yeast extract (Difco), 2.3 g/L monopotassium phosphate, 12.5 g/L dipotassium phosphate) at 30° C. for 16 hours, and the plasmid cDNA library was extracted and purified using QIAGEN Plasmid Kit (QIAGEN). The purified plasmid cDNA library was digested with Gene II and ExoIII (each from GIBCO BRL) to provide a single-stranded cDNA library.

On the other hand, a synthetic oligonucleotide (SEQ ID NO:16) was used as a probe for screening the positive cDNA clone. The probe was biotinylated at the 3'-end by using TdT and biotin-14-dCTP (GIBCO BRL). After the single-stranded cDNA library was treated at 95° C. for 1 minute, chilled on ice, and hybridized with the biotinylated probe at 37° C. for 1 hour. After the hybridization, MPG®-streptavidin beads (GIBCO BRL) were added to the reaction mixture and the tube was incubated at room temperature for 30 minutes with stirring at 2-minute intervals. Then, the tube was inserted in to a GIBCO BRL Magna-Sep™ (GIBCO BRL) and allowed to stand for 2 minutes. After the supernatant was discarded, the magnet beads were resuspended in wash buffer, and the supernatant was removed and discarded. This washing procedure was performed three times. Then, the tube was inserted in to the separator and allowed to stand for 5 min. After the supernatant was discarded, the beads were resuspended in 20 μl of elution buffer incubated at room temperature for 5 minutes, and the supernatant DNA solution was recovered.

To the thus-obtained DNA solution was added the synthetic oligonucleotide (SEQ ID NO:16) as a primer, and the mixture was incubated at 95° C. for 1 minute. 15 μl of the prewarmed repair mixture containing repair buffer, 10 mM sdNTP mix, and repair enzyme was added to the mixture and the mixture was incubated at 70° C. for 15 minutes for repaining the captured DNA. The thus-synthesized double-stranded DNA was introduced into *Escherichia coli* DH10B cells using an electroporation apparatus (Bio-Rad).

The thus-obtained transformants were screened by colony PCR using two oligonucleotides (SEQ ID NO:14 and SEQ ID NO:15) as primers. One colony which showed formation of a PCR-amplified 612 bp fragment was selected as a positive clone.

The *Escherichia coli* strain thus selected was cultured, DNA was extracted therefrom and subjected to reaction using a Taq Dideoxy Terminator Cycle Sequencing Kit (Perkin-Elmer), and the nucleotide sequence of the cDNA was determined using a model 373A DNA sequencer (Perkin-Elmer). The inserted DNA of the clone obtained contained a poly(A)$^+$ chain and had a 2773 base long nucleotide sequence (FIG. 1) containing the 1845-base open reading frame represented by SEQ ID NO:5. This cDNA fragment was found encoding a novel GFAT protein: TGC028-3, which is composed of 615 amino acid residues represented by SEQ ID NO:2, and the predicted gene product had 74% and 87.7% homology with human GFAT and TGC028-2 at the amino acid level, respectively.

The plasmid pTB1943 containing the DNA coding for the protein: TGC028-3 of the present invention was introduced into *Escherichia coli* DH10B cells to provide a transformant: *Escherichia coli* DH10B/pTB1943.

Example 2

Construction of a gene coding for the novel protein: TGC028-4

A 1788-base long nucleotide sequence was obtained from a plasmid DNA containing the open reading frame for TGC028-3 by digesting with the restriction enzymes EcoRV and BamHI. Separately, a strain of *Escherichia coli* harboring a plasmid containing a GFAT-like DNA fragment was cultured, the plasmid DNA was extracted therefrom, and the fragment excised with the restriction enzymes BamHI and SalI was recovered. Each fragment was inserted into a plasmid vector (pET 32a (+), Novagen) treated with the restriction enzymes EcoRV and SalI to thereby construct a plasmid named pTB1944 (FIG. 4). pTB1944 contained, in the vicinity of the termination codon, a sequence for 65 amino acid residues not found in TGC028-3. It contained an open reading frame consisting of the 2046-base long nucleotide sequence represented by SEQ ID NO:6 which encodes a gene product composed of 682 amino acid residues represented by in SEQ ID NO:3 (FIG. 2).

The plasmid pTB1944 containing the DNA coding for the protein: TGC028-4 of the present invention was introduced into *Escherichia coli* DH10B cells to provide a transformant: *Escherichia coli* DH10B/pTB1944.

Example 3

Determination of the tissue specificity of the gene expression by Northern blot

The determination of the tissue specificity of the gene expression by Northern blot analysis was performed using a Human Multiple Tissue Northern Blot Kit (Clontech) and a Human Multiple Tissue Northern Blot II (Clontech) membrane. These membranes were prehybridized in a hybridization buffer (50% deionized formamide, 5× SSPE, 2× Denhardt's solution, 2% SDS, 100 μg/ml heat-denatured herring sperm DNA) at 50° C. for 3 hours. Separately, as a probe a 1796-base nucleotide sequence represented by SEQ ID NO:17, coding for a partial sequence of the protein: TGP028-3 of the present invention, was labeled with ($\alpha$-$^{32}$P) dCTP (Amersham) by using Bca Best Labeling Kit (Takara Shuzo). By adding the labled probe in a hyridization buffer, hybridization was performed at 50° C. for 12 hours.

Figure 5:
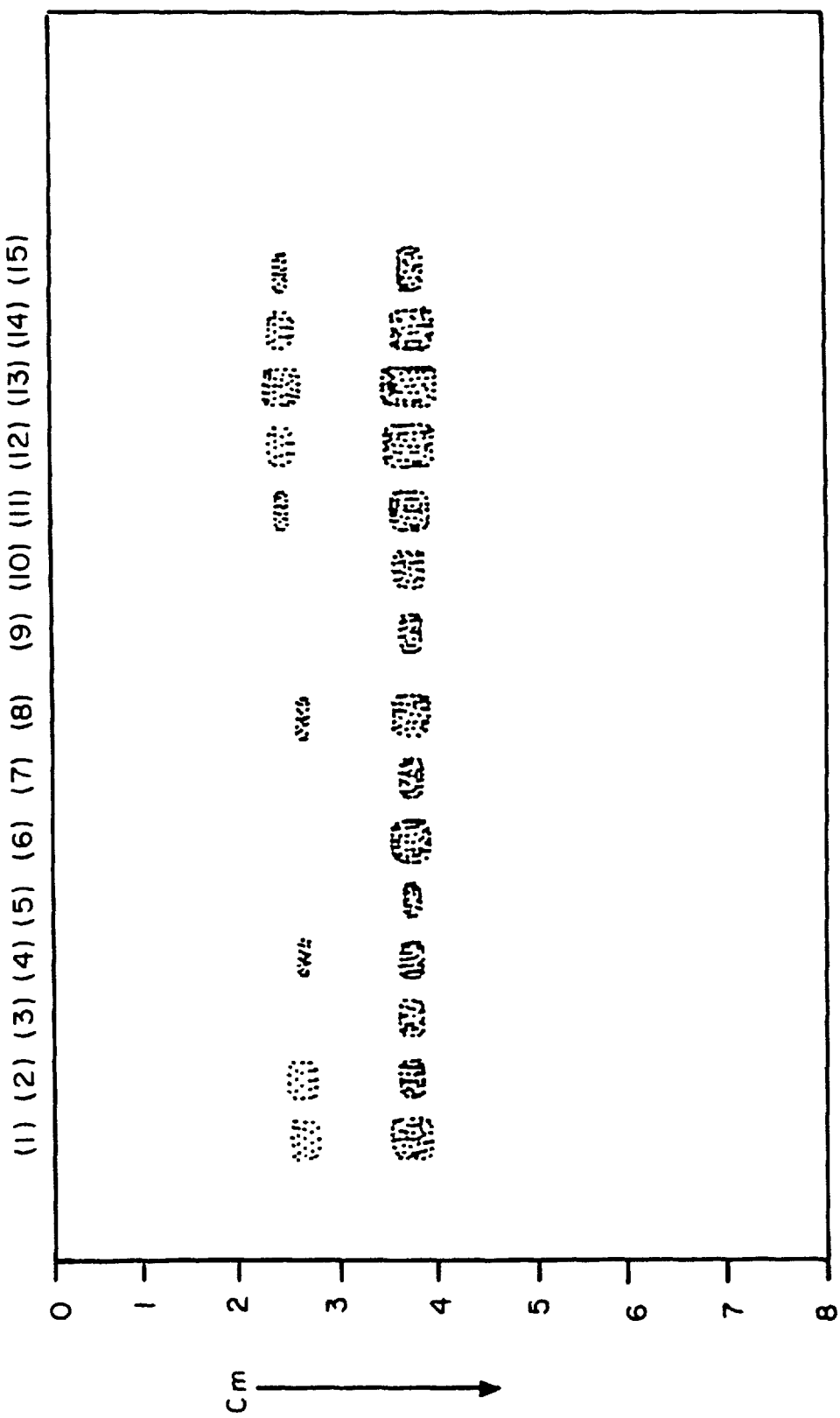
FIG. 5 shows the result of Northern blot analysis for the expression of the protein: TGC028-3 prepared from various human tissues, where lane 1 represents heart, lane 2 brain, lane 3 placenta, lane 4 lung, lane 5 liver, lane 6 skeletal muscle, lane 7 kidney, lane 8 pancreas, lane 9 spleen, lane 10 thymus, lane 11 prostate, lane 12 testis, lane 13 ovary, lane 14 small intestine and lane 15 large intestine.
Figure 6:
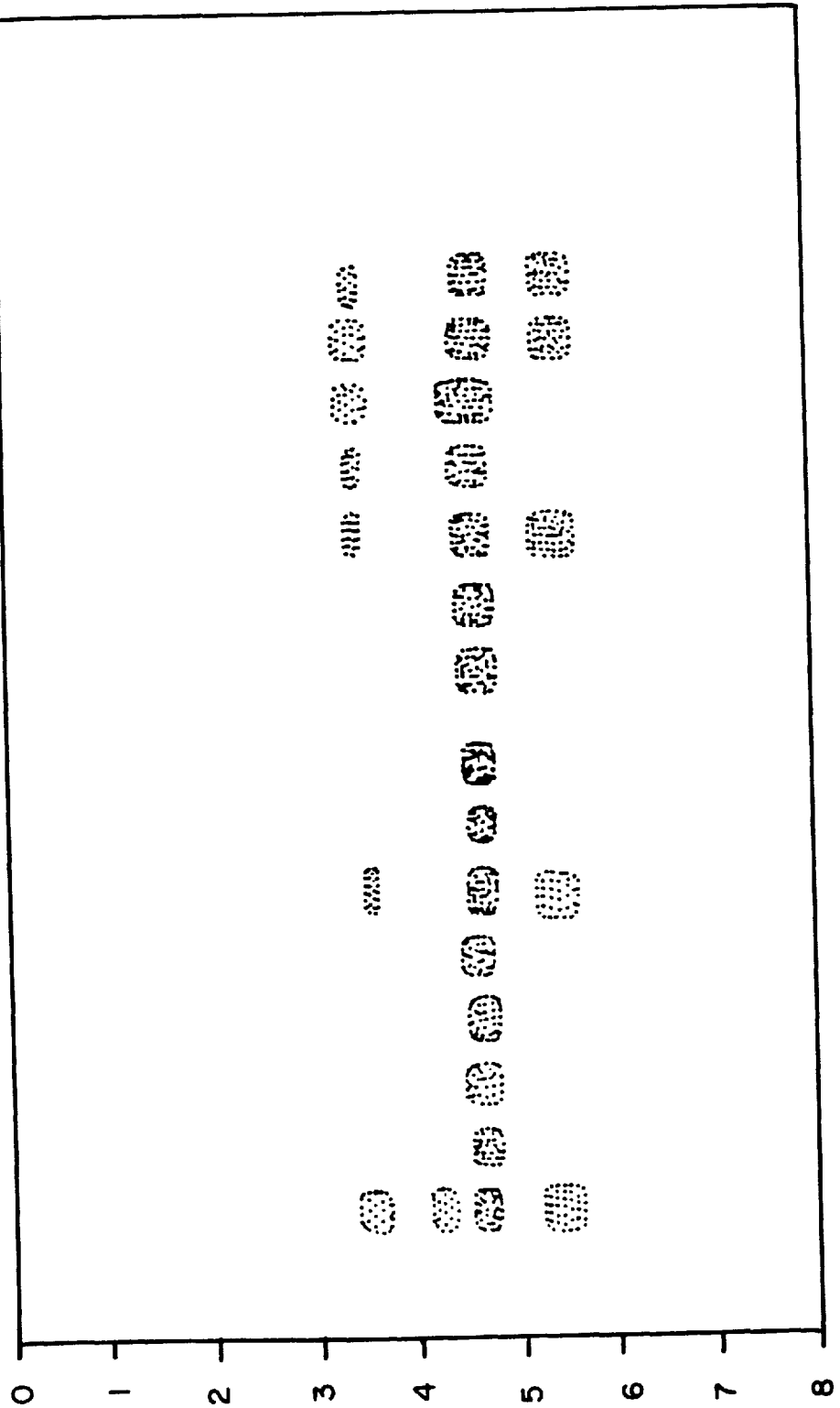
FIG. 6 shows the result of Northern blot analysis for the expression of human β-actin prepared from various human tissues, where lane 1 represents heart, lane 2 brain, lane 3 placenta, lane 4 lung, lane 5 liver, lane 6 skeletal muscle, lane 7 kidney, lane 8 pancreas, lane 9 spleen, lane 10 thymus, lane 11 prostate, lane 12 testis, lane 13 ovary, lane 14 small intestine and lane 15 large intestine.

After the hybridization, the membrames were washed twice in 2× SSC plus 0.05% SDS at room temperature and further twice with 0.1× SSC plus 0.1% SDS at 50° C. An autoradiogram for the filters was prepared to check for a band hybridized with the probe. As a result, one band was detected with all the tissues tested, namely heart, brain, placenta, lung, liver, smooth muscle, kidney, pancreas, spleen, thymus, prostate gland, testis, ovary, small intestine and large intestine. The size of the RNA was about 4.0 kb for all tissues (FIG. 5). This filter was deprived of the hybridized probe by boiling in 0.5% SDS for 10 minutes and, as a control run, hybridization with a human β-actin prove (Wako Pure Chemical) was performed; β-actin was detected as well in all tissues (FIG. 5).

Example 4

Expression of recombinant proteins: TGC028-3 and TGC028-4 using *Escherichia coli*

An expression vector for the protein: TGC028-3 of the present invention was constructed as follows. First, using the plasmid pTB1943 containing the DNA coding for TGC028-3 as the template and the two synthetic oligonucleotides represented by SEQ ID NO:20 and SEQ ID NO:21 as primers, together with TaKaRa Ex Taq™ (Takara Shuzo), and using a GeneAmp® PCR System 2400 thermal cycler (Perkin-Elmer), the DNA fragment coding for the protein: TGC028-3 of the present invention was amplified by repeating the following cycle 30 times following 1 minute at 94° C.: 1 minute at 94° C., 1 minute at 60° C., 2 minutes at 72° C. The DNA fragment thus-obtained was electrophoresed on a 1% agarose gel and, after identification of the desired DNA fragment, it was recovered and purified using QIAquick Gel Extraction Kit (QIAGEN). After the above DNA fragment was ligated to pT7 Blue T-Vector (Novagen) using DNA Ligation Kit Version 2 (Takara Shuzo), the ligation product was introduced into *Escherichia coli* JM109 cells and the objective plasmid DNA was selected and isolated from one of the ampicillin-resistant strains obtained. As for the nucleotide sequence of the cloned DNA fragment, a sequencing reaction was carried out on the GeneAmp® PCR system 2400 using an ABI PRISM™ Dye Terminator Cycle Sequencing FS Ready Reaction Kit (Perkin-Elmer) with various synthetic oligonucleotides as primers, under the conditions described in the document attached to the kit, followed by sample analysis on a model 373A DNA sequencer (Perkin-Elmer); The nucleotide sequences obtained were confirmed using the gene analysis software LASERGENE (DNASTAR). From among the thus-obtained plasmid DNAs, a clone giving no doubt about the nucleotide sequence was selected. The 5'- and 3'-ends of the DNA fragment were digested using the restriction enzymes EcoRV and SalI and a DNA fragment coding for TGC028-3 was recovered and purified in the same manner as mentioned above. Separately, pET-32a(+) vector (Novagen) was digested using the restriction enzymes EcoRV and SalI, followed by the same recovery and purification procedure as mentioned above. The DNA fragment coding for TGC028-3 as obtained previously was ligated to said pET-32a(+) vector using DNA Ligation Kit Version 2 (Takara Shuzo), the ligation product was introduced into *Escherichia coli* JM109 cells and the desired plasmid DNA was selected and isolated from one of the ampicillin-resistant strains obtained. The thus-constructed plasmid DNA was designated as pET-32a (+)/TGC028-3.

Then, for expressing the protein: TGC028-3, a DNA fragment coding for the protein was isolated from the plasmid pET-32a(+)/TGC028-3 and introduced into the pET32b(+) vector (Novagen). Then, for adding a site recognizable by the restriction enzyme NdeI to the N-terminal side of the DNA fragment coding for the protein: TGC028-3 and a site recognizable by the restriction enzyme SalI to the C-terminal side, amplification was performed on a Gene-Amp® PCR System 9600 thermal cycler (Perkin-Elmer) using pET-32a(+)/TGC028-3 as the template and the two synthetic oligonucleotides shown in SEQ ID NO:22 and SEQ ID NO:23 as primers, together with TaKaRa Ex Taq™ (Takara Shuzo), by repeating the following cycle 35 times following 1 minute at 94° C.: 10 seconds at 98° C., 1 minute at 55° C., 2 minutes at 72° C. The DNA fragment obtained was electrophoresed on a 1% agarose gel and, after identification of the desired DNA fragment, it was recovered and purified using QIAquick Gel Extraction Kit (QIAGEN). After thus-obtained DNA fragment was ligated to pT7Blue T-vector (Novagen) using DNA Ligation Kit Version 2 (Takara Shuzo), the ligation product was introduced into *Escherichia coli* JM109, cells and the objective plasmid DNA was selected and isolated from one of the ampicillin-resistant strains obtained. The nucleotide sequence of the cloned DNA fragment was confirmed by DNA sequencing in the same manner as mentioned above. From among the thus-obtained plasmid DNAs, the DNA of a clone giving no doubt about the nucleotide sequence was prepared, and the 5'- and 3'-ends thereof were digested using the restriction enzymes NdeI and SalI, followed by the same recovery and purification procedure as mentioned above. Separately, pET-32b(+) Vector (Novagen) was digested with the restriction enzymes NdeI and XhoI, followed by the same recovery and purification procedure as mentioned above. To this vector was ligated the DNA fragment coding for TGC028-3 obtained previously using DNA Ligation Kit Version 2 (Takara Shuzo), the ligation product was introduced into *Escherichia coli* BL21(DE3)pLysS cells and the objective plasmid DNA was selected and isolated from one of the ampicillin-resistant strains obtained. The thus-obtained plasmid DNA was designated as pET-32b(+)/TGC028-3. Consequently, TGC028-3 is expressed in the form of a fusion protein having 8 amino acid residues, Val, Glu, His, His, His, His, His, and His, added to the C terminal side.

On the other hand, an expression vector for the protein: TGC028-4 of the present invention was constructed as follows. First, for adding a site recognizable by the restriction enzyme NdeI to the N-terminal side of the DNA coding for the protein: TGC028-4 and a site recognizable by the restriction enzyme SalI to the C-terminal side, the DNA fragment coding for the protein: TGC028-4 of the present invention was amplified by PCR using the plasmid pTB1944 containing the DNA coding for TGC028-4 as the template and the two synthetic oligonucleotides shown in SEQ ID NO:24 and SEQ ID NO:25 as primers, together with TaKaRa Ex Taq™ (Takara Shuzo), and using GeneAmp® PCR System 9600 thermal cycler (Perkin-Elmer). The following cycle was repeated 35 times following 1 minute at 94° C.: 10 seconds at 98° C., 1 minute at 55° C., 2 minutes at 72° C. The PCR product thus-obtained was electrophoresed on a 1% agarose gel and, after identification of the objective DNA fragment, it was recovered and purified using QIAquick Gel Extraction Kit (QIAGEN). The above DNA fragment was ligated to pT7 Blue T-Vector (Novagen) using DNA Ligation Kit Version 2 (Takara Shuzo), the ligation product was introduced into *Escherichia coli* JM109, cells and the objective plasmid DNA was selected and isolated from one of the ampicillin-resistant strains obtained. The nucleotide sequence of the cloned DNA fragment was confirmed by DNA sequencing in the same manner as mentioned above. From among the thus-obtained plasmid DNAs, a clone giving no doubt about the nucleotide sequence was selected. The 5'- and 3'-ends of the DNA fragment were digested using the restriction enzymes NdeI and SalI and the DNA fragment coding for TGC028-4 was recovered and purified in the same manner as mentioned above. Separately, pET-32b(+) Vector (Novagen) was digested with the restriction enzymes NdeI and XhoI, followed by the same recovery and purification procedure as mentioned above. To this vector was ligated the DNA fragment coding for TGC028-4 as obtained previously using DNA Ligation Kit Version 2 (Takara Shuzo), the ligation product was introduced into *Escherichia coli* BL21(DE3) pLysS cells and the objective plasmid DNA was selected and isolated from one of the ampicillin-resistant strains obtained. The thus-obtained plasmid DNA was designated as pET32b (+)/TGC028-4-2. As a result, TGC028-4 is expressed as a fusion protein having 8 amino acid residues, Val Glu, His, His, His, His, His, His, added to the C-terminal side.

For expressing the recombinant proteins: TGC028-3 and TGC028-4 using *Escherichia coli*, the *E. coli* strain harboring pET32b(+)/TGC028-3-2 or pET32b(+)/TGC028-4-2 was cultured in 500 ml of L broth at 37° C. for 3 hours, IPTG was then added at a final concentration of 0.1 mM, and cultivation was continued at 23° C. for 15 hours. Then, cells were harvested by centrifugation (7,000 rpm, 10 minutes, 4° C.), suspended in 10 ml of saline (PBS) containing 1M urea, 0.25% sarcosyl, 0.5% NP-40 and 1 mM phenylmethylsulfonyl fluoride (PMSF), and sonicated. The cell lysate was centrifuged at 7,000 rpm (4° C.) for 10 minutes. Ammonium sulfate was added to the supernatant to 40% saturation and the resulting mixture was further centrifuged at 7,000 rpm (4° C.) for 10 minutes. To the supernatant obtained was added ammonium sulfate to 54% saturation, followed again by centrifugation (7,000 rpm, 10 minutes, 4° C.). The pellet thus obtained was dissolved in 10 ml of PBS and dialyzed against a large volume of PBS. The thus-obtained crude extract containing the recombinant protein: TGC028-3 or TGC028-4 was applied to a 2.5-ml His Bind column (Novagen), the column was washed with 25 ml of binding buffer and then with 15 ml of binding buffer containing 20 mM imidazole, and the recombinant protein: TGC028-3 or TGC028-4 was eluted with 15 ml of binding buffer containing 60 mM imidazole.

Example 5

Detection of GFAT activity of the proteins: TGC028-3 and TGC028-4

GFAT activity of the proteins: TGC028-3 and TGC028-4 was measured in the following manner. In a solution (0.1M $K_2HPO_4$, 50 mM KCl, 50 mM HEPES, 1 mM EDTA, 5 mM DTT, pH 7.5) were added glutamine and fructose-6-phosphate to final concentrations of 6 mM and 10 mM, respectively. Then, in 100 μl of this reaction mixture was added 1 μl of TGC028-3 or TGC028-4 protein, and the reaction mixture was incubated at room temperature for 5 hours. Thereafter, the reaction mixture was subjected to centrifugal filtration using a Ultrafree C3GC (cut-off molecular weight: 10,000; Millipore) and the filtrate obtained was mixed with an equal volume of a solution consisted of methanol, water, and triethylamine at the ratio of 2:2:1. After the mixture was dried in vacuo, the residue was dissolved in 20 μl of a mixed solution of methanol, water, and triethylamine-phenyl isothiocyanate (PITC) at the ratio of 7:1:1:1 and the reaction was carried out at room temperature for 20 minutes. The reaction mixture was dried in vacuo, the residue was dissolved in 100 μl of a mixed solution of 5 mM $NaH_2PO_4$ and 5% acetonitrile and the produced PITC-bound glucosamine-6-phosphate was checked by HPLC (Hitachi L-4200 UV-VIS Detector, L-6200 Intelligent Pump). As a control, PITC-bound glucosamine-6-phosphate was used. The column used was a TOSOH TSK-GEL ODS80TM column (Tosoh). Elution was carried out using a mobile phase comprising 232 mM sodium acetate, 0.1% triethylamine and 5% acetonitrile (pH 6.0) at a flow rate of 1 ml/minute and PITC-bound glucosamine-6-phosphate was detected at UV 254 nm. As a result, a peak was confirmed at the position corresponding to PITC-bound glucosamine-6-phosphate only when the protein: TGC028-3 or TGC028-4 had been added, together with fructose-6-phosphate, to the reaction mixture.

Industrial Applicability

The protein, its partial peptide or a salt thereof of the present invention has GFAT activity and so on.

The protein, its partial peptide or a salt thereof of the present invention and the DNA coding for the protein or the partial peptide of the present invention are useful as drugs such as a therapeutic or prophylactic agent for diseases such as hypoglycemia. Furthermore, the DNA of the present invention, with which an abnormal expression of the DNA of the present invention can be detected, is useful as an agent for gene diagnosis of diseases such as hypoglycemia or diabetes.

The antibody against the protein, its partial peptide or a salt thereof of the present invention specifically recognizes the protein or equivalent of the present invention, and can be used in assaying the protein or equivalent of the present invention in test liquid samples.

Furthermore, the protein, its partial peptide or a salt thereof of the present invention is useful as a reagent for the screening for compounds which promote or inhibit the GFAT activity of the protein or equivalent of the present invention.

We claim:

1. An isolated and purified protein comprising an amino acid sequence represented by SEQ ID No:1, or a salt thereof.

2. The protein according to claim 1, which has an amino acid sequence represented by SEQ ID No:2 or SEQ ID No:3.

3. The protein according to claim 1 or 2, wherein said protein has the activity of a glutamine:fructose-6-phosphate amidotranferase.

4. A partial peptide of the protein according to claim 1, or salt thereof, wherein said partial peptide, or a salt thereof, has the activity of a glutamine:fructose-6-phosphate amidotranferase.

5. A pharmaceutical composition comprising the protein according to claim 1, the partial peptide according to claim 4 or a salt thereof.

6. The pharmaceutical composition according to claim 5, which is a therapeutic or prophylactic agent for hypoglycemia.

7. A method for treating or preventing hypoglycemia in a mammal which comprises administering an effective amount of the protein according to claim 1, the partial peptide according to claim 4 or a salt thereof to said mammal.

8. Use of the protein according to claim 1, the partial peptide according to claim 4 or a salt thereof for production of a therapeutic or prophylactic agent for hypoglycemia.

* * * * *

UNITED STATES PATENT AND TRADEMARK OFFICE
CERTIFICATE OF CORRECTION

PATENT NO. : 5,876,713
DATED : March 2, 1999
INVENTOR(S) : Nishi, et al.

It is certified that error appears in the above-identified patent and that said Letters Patent is hereby corrected as shown below:

On the cover page, after "[76] Inventors: ..."

insert item [73]:   Assignee: Takeda Chemical Industries, Ltd., Osaka, Japan--

Signed and Sealed this

Eighteenth Day of April, 2000

Attest:

Q. TODD DICKINSON

*Attesting Officer*   *Director of Patents and Trademarks*

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 425 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Met  Cys  Gly  Ile  Phe  Ala  Tyr  Met  Asn  Tyr  Arg  Val  Pro  Arg  Thr  Arg
1                   5                        10                       15
```

Lys Glu Ile Phe Glu Thr Leu Ile Lys Gly Leu Gln Arg Leu Glu Tyr
                20                  25                  30

Arg Gly Tyr Asp Ser Ala Gly Val Ala Ile Asp Gly Asn Asn His Glu
            35                  40                  45

Val Lys Glu Arg His Ile Gln Leu Val Lys Lys Arg Gly Lys Val Lys
    50                  55                  60

Ala Leu Asp Glu Glu Leu Tyr Lys Gln Asp Ser Met Asp Leu Lys Val
65                  70                  75                  80

Glu Phe Glu Thr His Phe Gly Ile Ala His Thr Arg Trp Ala Thr His
                85                  90                  95

Gly Val Pro Ser Ala Val Asn Ser His Pro Gln Arg Ser Asp Lys Gly
            100                 105                 110

Asn Glu Phe Val Val Ile His Asn Gly Ile Ile Thr Asn Tyr Lys Asp
        115                 120                 125

Leu Arg Lys Phe Leu Glu Ser Lys Gly Tyr Glu Phe Glu Ser Glu Thr
    130                 135                 140

Asp Thr Glu Thr Ile Ala Lys Leu Ile Lys Tyr Val Phe Asp Asn Arg
145                 150                 155                 160

Glu Thr Glu Asp Ile Thr Phe Ser Thr Leu Val Glu Arg Val Ile Gln
                165                 170                 175

Gln Leu Glu Gly Ala Phe Ala Leu Phe Lys Ser Val His Tyr Pro
            180                 185                 190

Gly Glu Ala Val Ala Thr Arg Arg Gly Ser Pro Leu Leu Ile Gly Val
        195                 200                 205

Arg Ser Lys Tyr Lys Leu Ser Thr Glu Gln Ile Pro Ile Leu Tyr Arg
    210                 215                 220

Thr Cys Thr Leu Glu Asn Val Lys Asn Ile Cys Lys Thr Arg Met Lys
225                 230                 235                 240

Arg Leu Asp Ser Ser Ala Cys Leu His Ala Val Gly Asp Lys Ala Val
                245                 250                 255

Glu Phe Phe Phe Ala Ser Asp Ala Ser Ala Ile Ile Glu His Thr Asn
            260                 265                 270

Arg Val Ile Phe Leu Glu Asp Asp Ile Ala Ala Val Ala Asp Gly
        275                 280                 285

Lys Leu Ser Ile His Arg Val Lys Arg Ser Ala Ser Asp Asp Pro Ser
    290                 295                 300

Arg Ala Ile Gln Thr Leu Gln Met Glu Leu Gln Gln Ile Met Lys Gly
305                 310                 315                 320

Asn Phe Ser Ala Phe Met Gln Lys Glu Ile Phe Glu Gln Pro Glu Ser
                325                 330                 335

Val Phe Asn Thr Met Arg Gly Arg Val Asn Phe Glu Thr Asn Thr Val
            340                 345                 350

Leu Leu Gly Gly Leu Lys Asp His Leu Lys Glu Ile Arg Arg Cys Arg
        355                 360                 365

Arg Leu Ile Val Ile Gly Cys Gly Thr Ser Tyr His Ala Ala Val Ala
    370                 375                 380

Thr Arg Gln Val Leu Glu Glu Leu Thr Glu Leu Pro Val Met Val Glu
385                 390                 395                 400

Leu Ala Ser Asp Phe Leu Asp Arg Asn Thr Pro Val Phe Arg Asp Asp
                405                 410                 415

Val Cys Phe Phe Ile Ser Gln Ser Gly
            420                 425

( 2 ) INFORMATION FOR SEQ ID NO:2:

( i ) SEQUENCE CHARACTERISTICS:
        ( A ) LENGTH: 615 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met Cys Gly Ile Phe Ala Tyr Met Asn Tyr Arg Val Pro Arg Thr Arg
 1               5                  10                  15
Lys Glu Ile Phe Glu Thr Leu Ile Lys Gly Leu Gln Arg Leu Glu Tyr
                20                  25                  30
Arg Gly Tyr Asp Ser Ala Gly Val Ala Ile Asp Gly Asn Asn His Glu
            35                  40                  45
Val Lys Glu Arg His Ile Gln Leu Val Lys Lys Arg Gly Lys Val Lys
    50                  55                  60
Ala Leu Asp Glu Glu Leu Tyr Lys Gln Asp Ser Met Asp Leu Lys Val
65                  70                  75                  80
Glu Phe Glu Thr His Phe Gly Ile Ala His Thr Arg Trp Ala Thr His
                85                  90                  95
Gly Val Pro Ser Ala Val Asn Ser His Pro Gln Arg Ser Asp Lys Gly
                100                 105                 110
Asn Glu Phe Val Val Ile His Asn Gly Ile Ile Thr Asn Tyr Lys Asp
            115                 120                 125
Leu Arg Lys Phe Leu Glu Ser Lys Gly Tyr Glu Phe Glu Ser Glu Thr
    130                 135                 140
Asp Thr Glu Thr Ile Ala Lys Leu Ile Lys Tyr Val Phe Asp Asn Arg
145                 150                 155                 160
Glu Thr Glu Asp Ile Thr Phe Ser Thr Leu Val Glu Arg Val Ile Gln
                165                 170                 175
Gln Leu Glu Gly Ala Phe Ala Leu Val Phe Lys Ser Val His Tyr Pro
            180                 185                 190
Gly Glu Ala Val Ala Thr Arg Arg Gly Ser Pro Leu Leu Ile Gly Val
            195                 200                 205
Arg Ser Lys Tyr Lys Leu Ser Thr Glu Gln Ile Pro Ile Leu Tyr Arg
    210                 215                 220
Thr Cys Thr Leu Glu Asn Val Lys Asn Ile Cys Lys Thr Arg Met Lys
225                 230                 235                 240
Arg Leu Asp Ser Ser Ala Cys Leu His Ala Val Gly Asp Lys Ala Val
                245                 250                 255
Glu Phe Phe Phe Ala Ser Asp Ala Ser Ala Ile Ile Glu His Thr Asn
            260                 265                 270
Arg Val Ile Phe Leu Glu Asp Asp Ile Ala Ala Val Ala Asp Gly
    275                 280                 285
Lys Leu Ser Ile His Arg Val Lys Arg Ser Ala Ser Asp Asp Pro Ser
    290                 295                 300
Arg Ala Ile Gln Thr Leu Gln Met Glu Leu Gln Gln Ile Met Lys Gly
305                 310                 315                 320
Asn Phe Ser Ala Phe Met Gln Lys Glu Ile Phe Glu Gln Pro Glu Ser
                325                 330                 335
Val Phe Asn Thr Met Arg Gly Arg Val Asn Phe Glu Thr Asn Thr Val
                340                 345                 350
Leu Leu Gly Gly Leu Lys Asp His Leu Lys Glu Ile Arg Arg Cys Arg
            355                 360                 365
```

```
Arg  Leu  Ile  Val  Ile  Gly  Cys  Gly  Thr  Ser  Tyr  His  Ala  Ala  Val  Ala
     370                 375                      380

Thr  Arg  Gln  Val  Leu  Glu  Glu  Leu  Thr  Glu  Leu  Pro  Val  Met  Val  Glu
385                      390                      395                           400

Leu  Ala  Ser  Asp  Phe  Leu  Asp  Arg  Asn  Thr  Pro  Val  Phe  Arg  Asp  Asp
               405                      410                           415

Val  Cys  Phe  Phe  Ile  Ser  Gln  Ser  Gly  Glu  Thr  Ala  Asp  Thr  Leu  Leu
               420                 425                      430

Ala  Leu  Arg  Tyr  Cys  Lys  Asp  Arg  Gly  Ala  Leu  Thr  Val  Gly  Val  Thr
          435                      440                      445

Asn  Thr  Val  Gly  Ser  Ser  Ile  Ser  Arg  Glu  Thr  Asp  Cys  Gly  Val  His
     450                      455                      460

Ile  Asn  Ala  Gly  Pro  Glu  Ile  Gly  Val  Ala  Ser  Thr  Lys  Ala  Tyr  Thr
465                      470                      475                           480

Ser  Gln  Phe  Ile  Ser  Leu  Val  Met  Phe  Gly  Leu  Met  Met  Ser  Glu  Asp
                    485                      490                      495

Arg  Ile  Ser  Leu  Gln  Asn  Arg  Arg  Gln  Glu  Ile  Ile  Arg  Gly  Leu  Arg
               500                      505                      510

Ser  Leu  Pro  Glu  Leu  Ile  Lys  Glu  Val  Leu  Ser  Leu  Glu  Glu  Lys  Ile
          515                      520                      525

His  Asp  Leu  Ala  Leu  Glu  Leu  Tyr  Thr  Gln  Arg  Ser  Leu  Leu  Val  Met
     530                      535                      540

Gly  Arg  Gly  Tyr  Asn  Tyr  Ala  Thr  Cys  Leu  Glu  Gly  Ala  Leu  Lys  Ile
545                      550                      555                           560

Lys  Glu  Ile  Thr  Tyr  Met  His  Ser  Glu  Gly  Ile  Leu  Ala  Gly  Glu  Leu
               565                      570                      575

Lys  His  Gly  Pro  Leu  Ala  Leu  Ile  Asp  Lys  Gln  Met  Pro  Val  Ile  Met
               580                      585                      590

Val  Ile  Met  Lys  Asp  Pro  Cys  Phe  Ala  Lys  Cys  Gln  Asn  Ala  Leu  Gln
          595                      600                      605

Gln  Val  Thr  Ala  Arg  Gln  Val
     610                 615
```

(2) INFORMATION FOR SEQ ID NO:3:

(i) SEQUENCE CHARACTERISTICS:
        (A) LENGTH: 682 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met  Cys  Gly  Ile  Phe  Ala  Tyr  Met  Asn  Tyr  Arg  Val  Pro  Arg  Thr  Arg
1                   5                   10                       15

Lys  Glu  Ile  Phe  Glu  Thr  Leu  Ile  Lys  Gly  Leu  Gln  Arg  Leu  Glu  Tyr
               20                  25                       30

Arg  Gly  Tyr  Asp  Ser  Ala  Gly  Val  Ala  Ile  Asp  Gly  Asn  Asn  His  Glu
          35                      40                       45

Val  Lys  Glu  Arg  His  Ile  Gln  Leu  Val  Lys  Lys  Arg  Gly  Lys  Val  Lys
     50                      55                       60

Ala  Leu  Asp  Glu  Glu  Leu  Tyr  Lys  Gln  Asp  Ser  Met  Asp  Leu  Lys  Val
65                       70                  75                            80

Glu  Phe  Glu  Thr  His  Phe  Gly  Ile  Ala  His  Thr  Arg  Trp  Ala  Thr  His
               85                      90                       95
```

```
Gly  Val  Pro  Ser  Ala  Val  Asn  Ser  His  Pro  Gln  Arg  Ser  Asp  Lys  Gly
               100                      105                     110

Asn  Glu  Phe  Val  Val  Ile  His  Asn  Gly  Ile  Ile  Thr  Asn  Tyr  Lys  Asp
          115                      120                     125

Leu  Arg  Lys  Phe  Leu  Glu  Ser  Lys  Gly  Tyr  Glu  Phe  Glu  Ser  Glu  Thr
     130                      135                     140

Asp  Thr  Glu  Thr  Ile  Ala  Lys  Leu  Ile  Lys  Tyr  Val  Phe  Asp  Asn  Arg
145                      150                     155                          160

Glu  Thr  Glu  Asp  Ile  Thr  Phe  Ser  Thr  Leu  Val  Glu  Arg  Val  Ile  Gln
                    165                     170                     175

Gln  Leu  Glu  Gly  Ala  Phe  Ala  Leu  Val  Phe  Lys  Ser  Val  His  Tyr  Pro
               180                     185                     190

Gly  Glu  Ala  Val  Ala  Thr  Arg  Arg  Gly  Ser  Pro  Leu  Leu  Ile  Gly  Val
               195                     200                     205

Arg  Ser  Lys  Tyr  Lys  Leu  Ser  Thr  Glu  Gln  Ile  Pro  Ile  Leu  Tyr  Arg
     210                      215                     220

Thr  Cys  Thr  Leu  Glu  Asn  Val  Lys  Asn  Ile  Cys  Lys  Thr  Arg  Met  Lys
225                      230                     235                          240

Arg  Leu  Asp  Ser  Ser  Ala  Cys  Leu  His  Ala  Val  Gly  Asp  Lys  Ala  Val
                    245                     250                     255

Glu  Phe  Phe  Phe  Ala  Ser  Asp  Ala  Ser  Ala  Ile  Ile  Glu  His  Thr  Asn
               260                     265                     270

Arg  Val  Ile  Phe  Leu  Glu  Asp  Asp  Ile  Ala  Ala  Val  Ala  Asp  Gly
          275                     280                     285

Lys  Leu  Ser  Ile  His  Arg  Val  Lys  Arg  Ser  Ala  Ser  Asp  Asp  Pro  Ser
     290                      295                     300

Arg  Ala  Ile  Gln  Thr  Leu  Gln  Met  Glu  Leu  Gln  Gln  Ile  Met  Lys  Gly
305                      310                     315                          320

Asn  Phe  Ser  Ala  Phe  Met  Gln  Lys  Glu  Ile  Phe  Glu  Gln  Pro  Glu  Ser
                    325                     330                     335

Val  Phe  Asn  Thr  Met  Arg  Gly  Arg  Val  Asn  Phe  Glu  Thr  Asn  Thr  Val
                    340                     345                     350

Leu  Leu  Gly  Gly  Leu  Lys  Asp  His  Leu  Lys  Glu  Ile  Arg  Arg  Cys  Arg
               355                     360                     365

Arg  Leu  Ile  Val  Ile  Gly  Cys  Gly  Thr  Ser  Tyr  His  Ala  Ala  Val  Ala
     370                      375                     380

Thr  Arg  Gln  Val  Leu  Glu  Glu  Leu  Thr  Glu  Leu  Pro  Val  Met  Val  Glu
385                      390                     395                          400

Leu  Ala  Ser  Asp  Phe  Leu  Asp  Arg  Asn  Thr  Pro  Val  Phe  Arg  Asp  Asp
                    405                     410                     415

Val  Cys  Phe  Phe  Ile  Ser  Gln  Ser  Gly  Glu  Thr  Ala  Asp  Thr  Leu  Leu
               420                     425                     430

Ala  Leu  Arg  Tyr  Cys  Lys  Asp  Arg  Gly  Ala  Leu  Thr  Val  Gly  Val  Thr
          435                     440                     445

Asn  Thr  Val  Gly  Ser  Ser  Ile  Ser  Arg  Glu  Thr  Asp  Cys  Gly  Val  His
450                      455                     460

Ile  Asn  Ala  Gly  Pro  Glu  Ile  Gly  Val  Ala  Ser  Thr  Lys  Ala  Tyr  Thr
465                      470                     475                          480

Ser  Gln  Phe  Ile  Ser  Leu  Val  Met  Phe  Gly  Leu  Met  Met  Ser  Glu  Asp
                    485                     490                     495

Arg  Ile  Ser  Leu  Gln  Asn  Arg  Arg  Gln  Glu  Ile  Ile  Arg  Gly  Leu  Arg
               500                     505                     510

Ser  Leu  Pro  Glu  Leu  Ile  Lys  Glu  Val  Leu  Ser  Leu  Glu  Glu  Lys  Ile
          515                     520                     525
```

| | | | | | | | | | | | | | | |
|---|---|---|---|---|---|---|---|---|---|---|---|---|---|---|
|  | His | Asp | Leu | Ala | Leu | Glu | Leu | Tyr | Thr | Gln | Arg | Ser | Leu | Leu | Val | Met |
|  |  | 530 |  |  |  |  | 535 |  |  |  |  | 540 |  |  |  |  |
|  | Gly | Arg | Gly | Tyr | Asn | Tyr | Ala | Thr | Cys | Leu | Glu | Gly | Ala | Leu | Lys | Ile |
|  | 545 |  |  |  |  | 550 |  |  |  |  | 555 |  |  |  |  | 560 |
|  | Lys | Glu | Ile | Thr | Tyr | Met | His | Ser | Glu | Gly | Ile | Leu | Ala | Gly | Glu | Leu |
|  |  |  |  |  | 565 |  |  |  |  | 570 |  |  |  |  | 575 |  |
|  | Lys | His | Gly | Pro | Leu | Ala | Leu | Ile | Asp | Lys | Gln | Met | Pro | Val | Ile | Met |
|  |  |  |  | 580 |  |  |  |  | 585 |  |  |  |  | 590 |  |  |
|  | Val | Ile | Met | Lys | Asp | Pro | Cys | Phe | Ala | Lys | Cys | Gln | Asn | Ala | Leu | Gln |
|  |  |  | 595 |  |  |  |  | 600 |  |  |  |  | 605 |  |  |  |
|  | Gln | Val | Thr | Ala | Arg | Gln | Gly | Arg | Pro | Ile | Ile | Leu | Cys | Ser | Lys | Asp |
|  |  | 610 |  |  |  |  | 615 |  |  |  |  | 620 |  |  |  |  |
|  | Asp | Thr | Glu | Ser | Ser | Lys | Phe | Ala | Tyr | Lys | Thr | Ile | Glu | Leu | Pro | His |
|  | 625 |  |  |  |  | 630 |  |  |  |  | 635 |  |  |  |  | 640 |
|  | Thr | Val | Asp | Cys | Leu | Gln | Gly | Ile | Leu | Ser | Val | Ile | Pro | Leu | Gln | Leu |
|  |  |  |  |  | 645 |  |  |  |  | 650 |  |  |  |  | 655 |  |
|  | Leu | Ser | Phe | His | Leu | Ala | Val | Leu | Arg | Gly | Tyr | Asp | Val | Asp | Phe | Pro |
|  |  |  |  | 660 |  |  |  |  | 665 |  |  |  |  | 670 |  |  |
|  | Arg | Asn | Leu | Ala | Lys | Ser | Val | Thr | Val | Glu |  |  |  |  |  |  |
|  |  |  |  | 675 |  |  |  | 680 |  |  |  |  |  |  |  |  |

( 2 ) INFORMATION FOR SEQ ID NO:4:

( i ) SEQUENCE CHARACTERISTICS:
        ( A ) LENGTH: 1275 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:4:

```
ATGTGCGGAA   TCTTTGCCTA   CATGAACTAC   AGAGTCCCCC   GGACGAGGAA   GGAGATCTTC      60
GAAACCCTCA   TCAAGGGCCT   GCAGCGGCTG   GAGTACAGAG   GCTACGACTC   GGCAGGTGTG     120
GCGATCGATG   GGAATAATCA   CGAAGTCAAA   GAAAGACACA   TTCAGCTGGT   CAAGAAAAGG     180
GGGAAAGTCA   AGGCTCTCGA   TGAAGAACTT   TACAAACAAG   ACAGCATGGA   CTTAAAAGTG     240
GAGTTTGAGA   CACACTTCGG   CATTGCCCAC   ACGCGCTGGG   CCACCCACGG   GGTCCCCAGT     300
GCTGTCAACA   GCCACCCTCA   GCGCTCAGAC   AAAGGCAACG   AATTTGTTGT   CATCCACAAT     360
GGGATCATCA   CAAATTACAA   AGATCTGAGG   AAATTTCTGG   AAAGCAAAGG   CTACGAGTTT     420
GAGTCAGAAA   CAGATACAGA   GACCATCGCC   AAGCTGATTA   AATATGTGTT   CGACAACAGA     480
GAAACTGAGG   ACATTACGTT   TTCAACGTTG   GTCGAGAGAG   TCATTCAGCA   GTTGGAAGGT     540
GCATTCGCGC   TGGTTTTCAA   GAGTGTCCAC   TACCCAGGAG   AAGCCGTTGC   CACACGGAGA     600
GGCAGCCCCC   TGCTCATCGG   AGTCCGGAGC   AAATACAAGC   TCTCCACAGA   ACAGATCCCT     660
ATCTTATACA   GGACGTGCAC   TCTGGAGAAT   GTGAAGAATA   TCTGTAAGAC   ACGGATGAAG     720
AGGCTGGACA   GCTCCGCCTG   CCTGCATGCT   GTGGGCGACA   AGGCCGTGGA   ATTCTTCTTT     780
GCTTCTGATG   CAAGCGCTAT   CATAGAGCAC   ACCAACCGGG   TCATCTTCCT   GGAGGACGAT     840
GACATCGCCG   CAGTGGCTGA   TGGGAAACTC   TCCATTCACC   GGGTCAAGCG   CTCGGCCAGT     900
GATGACCCAT   CTCGAGCCAT   CCAGACCTTG   CAGATGGAAC   TGCAGCAAAT   CATGAAAGGT     960
AACTTCAGTG   CGTTTATGCA   GAAGGAGATC   TTCAACAGC   CAGAATCAGT   TTTCAATACT    1020
ATGAGAGGTC   GGGTGAATTT   TGAAACCAAC   ACAGTGCTCC   TGGGTGGCTT   GAAGGACCAC    1080
```

| | | | | | |
|---|---|---|---|---|---|
|TTGAAGGAGA|TTCGACGATG|CCGACGGCTC|ATCGTGATTG|GCTGTGGAAC|CAGCTACCAC|1140|
|GCTGCCGTGG|CTACGCGGCA|AGTTTTGGAG|GAACTGACTG|AGCTTCCTGT|GATGGTTGAA|1200|
|CTTGCTAGTG|ATTTTCTGGA|CAGGAACACA|CCTGTGTTCA|GGGATGACGT|TTGCTTTTTC|1260|
|ATCAGCCAGT|CAGGC| | | | |1275|

( 2 ) INFORMATION FOR SEQ ID NO:5:

( i ) SEQUENCE CHARACTERISTICS:
        ( A ) LENGTH: 1845 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:5:

| | | | | | |
|---|---|---|---|---|---|
|ATGTGCGGAA|TCTTTGCCTA|CATGAACTAC|AGAGTCCCCC|GGACGAGGAA|GGAGATCTTC|60|
|GAAACCCTCA|TCAAGGGCCT|GCAGCGGCTG|GAGTACAGAG|GCTACGACTC|GGCAGGTGTG|120|
|GCGATCGATG|GGAATAATCA|CGAAGTCAAA|GAAAGACACA|TTCAGCTGGT|CAAGAAAAGG|180|
|GGGAAAGTCA|AGGCTCTCGA|TGAAGAACTT|TACAAACAAG|ACAGCATGGA|CTTAAAAGTG|240|
|GAGTTTGAGA|CACACTTCGG|CATTGCCCAC|ACGCGCTGGG|CCACCCACGG|GGTCCCCAGT|300|
|GCTGTCAACA|GCCACCCTCA|GCGCTCAGAC|AAAGGCAACG|AATTTGTTGT|CATCCACAAT|360|
|GGGATCATCA|CAAATTACAA|AGATCTGAGG|AAATTTCTGG|AAAGCAAAGG|CTACGAGTTT|420|
|GAGTCAGAAA|CAGATACAGA|GACCATCGCC|AAGCTGATTA|AATATGTGTT|CGACAACAGA|480|
|GAAACTGAGG|ACATTACGTT|TTCAACGTTG|GTCGAGAGAG|TCATTCAGCA|GTTGGAAGGT|540|
|GCATTCGCGC|TGGTTTTCAA|GAGTGTCCAC|TACCCAGGAG|AAGCCGTTGC|CACACGGAGA|600|
|GGCAGCCCCC|TGCTCATCGG|AGTCCGGAGC|AAATACAAGC|TCTCCACAGA|ACAGATCCCT|660|
|ATCTTATACA|GGACGTGCAC|TCTGGAGAAT|GTGAAGAATA|TCTGTAAGAC|ACGGATGAAG|720|
|AGGCTGGACA|GCTCCGCCTG|CCTGCATGCT|GTGGGCGACA|AGGCCGTGGA|ATTCTTCTTT|780|
|GCTTCTGATG|CAAGCGCTAT|CATAGAGCAC|ACCAACCGGG|TCATCTTCCT|GGAGGACGAT|840|
|GACATCGCCG|CAGTGGCTGA|TGGGAAACTC|TCCATTCACC|GGGTCAAGCG|CTCGGCCAGT|900|
|GATGACCCAT|CTCGAGCCAT|CCAGACCTTG|CAGATGGAAC|TGCAGCAAAT|CATGAAAGGT|960|
|AACTTCAGTG|CGTTTATGCA|GAAGGAGATC|TTCGAACAGC|CAGAATCAGT|TTTCAATACT|1020|
|ATGAGAGGTC|GGGTGAATTT|TGAAACCAAC|ACAGTGCTCC|TGGGTGGCTT|GAAGGACCAC|1080|
|TTGAAGGAGA|TTCGACGATG|CCGACGGCTC|ATCGTGATTG|GCTGTGGAAC|CAGCTACCAC|1140|
|GCTGCCGTGG|CTACGCGGCA|AGTTTTGGAG|GAACTGACTG|AGCTTCCTGT|GATGGTTGAA|1200|
|CTTGCTAGTG|ATTTTCTGGA|CAGGAACACA|CCTGTGTTCA|GGGATGACGT|TTGCTTTTTC|1260|
|ATCAGCCAGT|CAGGCGAGAC|CGCGGACACC|CTCCTGGCGC|TGCGCTACTG|TAAGGACCGC|1320|
|GGCGCTCTCA|CCGTGGGCGT|CACCAACACC|GTGGGCAGCT|CCATCTCTCG|CGAGACCGAC|1380|
|TGCGGCGTCC|ACATCAACGC|AGGGCCGGAG|ATCGGCGTGG|CCAGCACCAA|GGCTTATACC|1440|
|AGTCAGTTCA|TCTCTCTGGT|GATGTTTGGT|TTGATGATGT|CTGAAGACCG|AATTTCACTA|1500|
|CAAAACAGGA|GGCAAGAGAT|CATCCGTGGC|TTGAGATCTT|TACCTGAGCT|GATCAAGGAA|1560|
|GTGCTGTCTC|TGGAGGAGAA|GATCCACGAC|TTGGCCCTGG|AGCTCTACAC|GCAGAGATCG|1620|
|CTGCTGGTGA|TGGGGCGGGG|CTACAACTAT|GCCACCTGCC|TGGAAGGAGC|CCTGAAAATT|1680|
|AAAGAGATAA|CCTACATGCA|CTCAGAAGGC|ATCCTGGCTG|GGGAGCTGAA|GCACGGGCCC|1740|
|CTGGCACTGA|TTGACAAGCA|GATGCCCGTC|ATCATGGTCA|TTATGAAGGA|TCCTTGCTTC|1800|

| GCCAAATGCC | AGAACGCCCT | GCAGCAAGTC | ACGGCCCGCC | AGGTT | | 1845 |

(2) INFORMATION FOR SEQ ID NO:6:

(i) SEQUENCE CHARACTERISTICS:
        (A) LENGTH: 2046 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:6:

| ATGTGCGGAA | TCTTTGCCTA | CATGAACTAC | AGAGTCCCCC | GGACGAGGAA | GGAGATCTTC | 60 |
| GAAACCCTCA | TCAAGGGCCT | GCAGCGGCTG | GAGTACAGAG | GCTACGACTC | GGCAGGTGTG | 120 |
| GCGATCGATG | GAATAATCA | CGAAGTCAAA | GAAAGACACA | TTCAGCTGGT | CAAGAAAAGG | 180 |
| GGGAAAGTCA | AGGCTCTCGA | TGAAGAACTT | TACAAACAAG | ACAGCATGGA | CTTAAAAGTG | 240 |
| GAGTTTGAGA | CACACTTCGG | CATTGCCCAC | ACGCGCTGGG | CCACCCACGG | GGTCCCCAGT | 300 |
| GCTGTCAACA | GCCACCCTCA | GCGCTCAGAC | AAAGGCAACG | AATTTGTTGT | CATCCACAAT | 360 |
| GGGATCATCA | CAAATTACAA | AGATCTGAGG | AAATTTCTGG | AAAGCAAAGG | CTACGAGTTT | 420 |
| GAGTCAGAAA | CAGATACAGA | GACCATCGCC | AAGCTGATTA | AATATGTGTT | CGACAACAGA | 480 |
| GAAACTGAGG | ACATTACGTT | TTCAACGTTG | GTCGAGAGAG | TCATTCAGCA | GTTGGAAGGT | 540 |
| GCATTCGCGC | TGGTTTTCAA | GAGTGTCCAC | TACCCAGGAG | AAGCCGTTGC | CACACGGAGA | 600 |
| GGCAGCCCCC | TGCTCATCGG | AGTCCGGAGC | AAATACAAGC | TCTCCACAGA | ACAGATCCCT | 660 |
| ATCTTATACA | GGACGTGCAC | TCTGGAGAAT | GTGAAGAATA | TCTGTAAGAC | ACGGATGAAG | 720 |
| AGGCTGGACA | GCTCCGCCTG | CCTGCATGCT | GTGGGCGACA | AGGCCGTGGA | ATTCTTCTTT | 780 |
| GCTTCTGATG | CAAGCGCTAT | CATAGAGCAC | ACCAACCGGG | TCATCTTCCT | GGAGGACGAT | 840 |
| GACATCGCCG | CAGTGGCTGA | TGGGAAACTC | TCCATTCACC | GGGTCAAGCG | CTCGGCCAGT | 900 |
| GATGACCCAT | CTCGAGCCAT | CCAGACCTTG | CAGATGGAAC | TGCAGCAAAT | CATGAAAGGT | 960 |
| AACTTCAGTG | CGTTTATGCA | GAAGGAGATC | TTCGAACAGC | CAGAATCAGT | TTTCAATACT | 1020 |
| ATGAGAGGTC | GGGTGAATTT | TGAAACCAAC | ACAGTGCTCC | TGGGTGGCTT | GAAGGACCAC | 1080 |
| TTGAAGGAGA | TTCGACGATG | CCGACGGCTC | ATCGTGATTG | GCTGTGGAAC | CAGCTACCAC | 1140 |
| GCTGCCGTGG | CTACGCGGCA | AGTTTTGGAG | GAACTGACTG | AGCTTCCTGT | GATGGTTGAA | 1200 |
| CTTGCTAGTG | ATTTTCTGGA | CAGGAACACA | CCTGTGTTCA | GGGATGACGT | TTGCTTTTTC | 1260 |
| ATCAGCCAGT | CAGGCGAGAC | CGCGGACACC | CTCCTGGCGC | TGCGCTACTG | TAAGGACCGC | 1320 |
| GGCGCTCTCA | CCGTGGGCGT | CACCAACACC | GTGGGCAGCT | CCATCTCTCG | CGAGACCGAC | 1380 |
| TGCGGCGTCC | ACATCAACGC | AGGGCCGGAG | ATCGGCGTGG | CCAGCACCAA | GGCTTATACC | 1440 |
| AGTCAGTTCA | TCTCTCTGGT | GATGTTTGGT | TTGATGATGT | CTGAAGACCG | AATTTCACTA | 1500 |
| CAAAACAGGA | GGCAAGAGAT | CATCCGTGGC | TTGAGATCTT | TACCTGAGCT | GATCAAGGAA | 1560 |
| GTGCTGTCTC | TGGAGGAGAA | GATCCACGAC | TTGGCCCTGG | AGCTCTACAC | GCAGAGATCG | 1620 |
| CTGCTGGTGA | TGGGGCGGGG | CTACAACTAT | GCCACCTGCC | TGGAAGGAGC | CCTGAAAATT | 1680 |
| AAAGAGATAA | CCTACATGCA | CTCAGAAGGC | ATCCTGGCTG | GGGAGCTGAA | GCACGGGCCC | 1740 |
| CTGGCACTGA | TTGACAAGCA | GATGCCCGTC | ATCATGGTCA | TTATGAAGGA | TCCTTGCTTC | 1800 |
| GCCAAATGCC | AGAACGCCCT | GCAGCAAGTC | ACGGCCCGCC | AGGGTCGCCC | CATTATACTG | 1860 |
| TGCTCCAAGG | ACGATACTGA | AAGTTCCAAG | TTTGCGTATA | AGACAATTGA | GCTGCCCCAC | 1920 |

```
ACTGTGGACT GCCTCCAGGG CATCCTGAGC GTGATTCCGC TGCAGCTGCT GTCCTTCCAC     1980
CTGGCTGTTC TCCGAGGATA TGACGTTGAC TTCCCCAGAA ATCTGGCCAA GTCTGTAACT     2040
GTGGAA                                                                2046
```

(2) INFORMATION FOR SEQ ID NO:7:

(i) SEQUENCE CHARACTERISTICS:
        (A) LENGTH: 149 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Met Cys Gly Ile Phe Ala Tyr Met Asn Tyr Arg Val Pro Arg Thr Arg
1               5                   10                  15
Lys Glu Ile Phe Glu Thr Leu Ile Lys Gly Leu Gln Arg Leu Glu Tyr
            20                  25                  30
Arg Gly Tyr Asp Ser Ala Gly Val Ala Ile Asp Gly Asn Asn His Glu
        35                  40                  45
Val Lys Glu Arg His Ile Gln Leu Val Lys Lys Arg Gly Lys Val Lys
50                  55                  60
Ala Leu Asp Glu Glu Leu Tyr Lys Gln Asp Ser Met Asp Leu Lys Val
65                  70                  75                  80
Glu Phe Glu Thr His Phe Gly Ile Ala His Thr Arg Trp Ala Thr His
                85                  90                  95
Gly Val Pro Ser Ala Val Asn Ser His Pro Gln Arg Ser Asp Lys Gly
            100                 105                 110
Asn Glu Phe Val Val Ile His Asn Gly Ile Ile Thr Asn Tyr Lys Asp
        115                 120                 125
Leu Arg Lys Phe Leu Glu Ser Lys Gly Tyr Glu Phe Glu Ser Glu Thr
    130                 135                 140
Asp Thr Glu Thr Ile
145
```

(2) INFORMATION FOR SEQ ID NO:8:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Ala Lys Leu Ile Lys Tyr Val Phe Asp Asn Arg Glu Thr Glu Asp Ile
1               5                   10                  15
Thr Phe Ser Thr Leu Val Glu Arg Val Ile Gln Gln Leu Glu Gly Ala
            20                  25                  30
Phe Ala Leu Val Phe Lys Ser Val His Tyr Pro Gly Glu Ala Val Ala
        35                  40                  45
Thr Arg Arg Gly Ser Pro Leu Leu Ile Gly Val Arg Ser Lys Tyr Lys
50                  55                  60
Leu Ser Thr Glu Gln Ile Pro Ile Leu Tyr Arg Thr Cys Thr Leu Glu
65                  70                  75                  80
Asn Val Lys Asn Ile Cys Lys Thr Arg Met Lys Arg Leu Asp Ser Ser
                85                  90                  95
```

|     |     |     |     |     |     |     |     |     |     |     |     |     |     |
| --- | --- | --- | --- | --- | --- | --- | --- | --- | --- | --- | --- | --- | --- |
| Ala | Cys | Leu | His 100 | Ala | Val | Gly | Asp | Lys 105 | Ala | Val | Glu | Phe | Phe 110 | Phe | Ala |
| Ser | Asp | Ala 115 | Ser | Ala | Ile | Ile | Glu 120 | His | | | | | |

(2) INFORMATION FOR SEQ ID NO:9:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Thr Asn Arg Val Ile Phe Leu Glu Asp Asp Ile Ala Ala Val Ala
 1               5                  10                 15

Asp Gly Lys Leu Ser Ile His Arg Val Lys Arg Ser Ala Ser Asp Asp
             20                 25                 30

Pro Ser Arg Ala Ile Gln Thr Leu Gln Met Glu Leu Gln Gln Ile Met
             35                 40                 45

Lys Gly Asn Phe Ser Ala Phe Met Gln Lys Glu Ile Phe Glu Gln Pro
 50                 55                 60

Glu Ser Val Phe Asn Thr Met Arg Gly Arg Val Asn Phe Glu Thr Asn
 65                 70                 75                 80

Thr Val Leu Leu Gly Gly Leu Lys Asp His Leu Lys Glu Ile Arg Arg
             85                 90                 95

Cys Arg Arg Leu Ile Val Ile Gly Cys Gly Thr Ser Tyr His Ala Ala
             100                105                110

Val Ala Thr Arg Gln Val Leu Glu Glu Leu Thr Glu Leu Pro Val Met
             115                120                125

Val Glu Leu Ala Ser Asp Phe Leu Asp Arg Asn Thr Pro Val Phe Arg
             130                135                140

Asp Asp Val Cys Phe Phe Ile Ser Gln Ser Gly
145                 150                155
```

(2) INFORMATION FOR SEQ ID NO:10:

(i) SEQUENCE CHARACTERISTICS:
        (A) LENGTH: 447 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:10:

```
ATGTGCGGAA TCTTTGCCTA CATGAACTAC AGAGTCCCCC GGACGAGGAA GGAGATCTTC    60
GAAACCCTCA TCAAGGGCCT GCAGCGGCTG GAGTACAGAG CTACGACTC GGCAGGTGTG   120
GCGATCGATG GGAATAATCA CGAAGTCAAA GAAAGACACA TTCAGCTGGT CAAGAAAAGG   180
GGGAAAGTCA AGGCTCTCGA TGAAGAACTT TACAAACAAG ACAGCATGGA CTTAAAAGTG   240
GAGTTTGAGA CACACTTCGG CATTGCCCAC ACGCGCTGGG CCACCCACGG GGTCCCCAGT   300
GCTGTCAACA GCCACCCTCA GCGCTCAGAC AAAGGCAACG AATTTGTTGT CATCCACAAT   360
GGGATCATCA CAAATTACAA AGATCTGAGG AAATTTCTGG AAAGCAAAGG CTACGAGTTT   420
GAGTCAGAAA CAGATACAGA GACCATC                                       447
```

(2) INFORMATION FOR SEQ ID NO:11:

( i ) SEQUENCE CHARACTERISTICS:
  ( A ) LENGTH: 363 base pairs
  ( B ) TYPE: nucleic acid
  ( C ) STRANDEDNESS: double
  ( D ) TOPOLOGY: linear ( i i ) MOLECULE TYPE: cDNA ( x i ) SEQUENCE DESCRIPTION: SEQ ID NO:11:

| | | | | | | |
|---|---|---|---|---|---|---|
| GCCAAGCTGA | TTAAATATGT | GTTCGACAAC | AGAGAAACTG | AGGACATTAC | GTTTTCAACG | 60 |
| TTGGTCGAGA | GAGTCATTCA | GCAGTTGGAA | GGTGCATTCG | CGCTGGTTTT | CAAGAGTGTC | 120 |
| CACTACCCAG | GAGAAGCCGT | TGCCACACGG | AGAGGCAGCC | CCCTGCTCAT | CGGAGTCCGG | 180 |
| AGCAAATACA | AGCTCTCCAC | AGAACAGATC | CCTATCTTAT | ACAGGACGTG | CACTCTGGAG | 240 |
| AATGTGAAGA | ATATCTGTAA | GACACGGATG | AAGAGGCTGG | ACAGCTCCGC | CTGCCTGCAT | 300 |
| GCTGTGGGCG | ACAAGGCCGT | GGAATTCTTC | TTTGCTTCTG | ATGCAAGCGC | TATCATAGAG | 360 |
| CAC | | | | | | 363 |

( 2 ) INFORMATION FOR SEQ ID NO:12:

( i ) SEQUENCE CHARACTERISTICS:
  ( A ) LENGTH: 465 base pairs
  ( B ) TYPE: nucleic acid
  ( C ) STRANDEDNESS: double
  ( D ) TOPOLOGY: linear ( i i ) MOLECULE TYPE: cDNA ( x i ) SEQUENCE DESCRIPTION: SEQ ID NO:12:

| | | | | | | |
|---|---|---|---|---|---|---|
| ACCAACCGGG | TCATCTTCCT | GGAGGACGAT | GACATCGCCG | CAGTGGCTGA | TGGGAAACTC | 60 |
| TCCATTCACC | GGGTCAAGCG | CTCGGCCAGT | GATGACCCAT | CTCGAGCCAT | CCAGACCTTG | 120 |
| CAGATGGAAC | TGCAGCAAAT | CATGAAAGGT | AACTTCAGTG | CGTTTATGCA | GAAGGAGATC | 180 |
| TTCGAACAGC | CAGAATCAGT | TTTCAATACT | ATGAGAGGTC | GGGTGAATTT | TGAAACCAAC | 240 |
| ACAGTGCTCC | TGGGTGGCTT | GAAGGACCAC | TTGAAGGAGA | TTCGACGATG | CCGACGGCTC | 300 |
| ATCGTGATTG | GCTGTGGAAC | CAGCTACCAC | GCTGCCGTGG | CTACGCGGCA | AGTTTTGGAG | 360 |
| GAACTGACTG | AGCTTCCTGT | GATGGTTGAA | CTTGCTAGTG | ATTTCTGGA | CAGGAACACA | 420 |
| CCTGTGTTCA | GGGATGACGT | TTGCTTTTTC | ATCAGCCAGT | CAGGT | | 465 |

( 2 ) INFORMATION FOR SEQ ID NO:13:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "SYNTHETIC DNA"

( x i ) SEQUENCE DESCRIPTION: SEQ ID NO:13:

| | | | |
|---|---|---|---|
| AAGGAGCCCG | AGAAGCAGCC | ACGAT | 25 |

( 2 ) INFORMATION FOR SEQ ID NO:14:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: other nucleic acid (A) DESCRIPTION: /desc = "SYNTHETIC DNA"

(xi) SEQUENCE DESCRIPTION: SEQ ID NO:14:

CACTTCGGCA TTGCCCACAC GC 22

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:15:

GTGAATGGAG AGTTTTCCAT 20

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:16:

CGACAACAGA GAAACTGAGG AC 22

(2) INFORMATION FOR SEQ ID NO:17:

(i) SEQUENCE CHARACTERISTICS:
        (A) LENGTH: 1796 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:17:

GATCCACGAT GTGCGGAATC TTTGCCTACA TGAACTACAG AGTCCCCCGG ACGAGGAAGG 60

AGATCTTCGA AACCCTCATC AAGGGCCTGC AGCGGCTGGA GTACAGAGGC TACGACTCGG 120

CAGGTGTGGC GATCGATGGG AATAATCACG AAGTCAAAGA AAGACACATT CAGCTGGTCA 180

AGAAAAGGGG GAAAGTCAAG GCTCTCGATG AAGAACTTTA CAAACAAGAC AGCATGGACT 240

TAAAAGTGGA GTTTGAGACA CACTTCGGCA TTGCCCACAC GCGCTGGGCC ACCCACGGGG 300

TCCCCAGTGC TGTCAACAGC CACCCTCAGC GCTCAGACAA AGGCAACGAA TTTGTTGTCA 360

TCCACAATGG GATCATCACA AATTACAAAG ATCTGAGGAA ATTTCTGGAA AGCAAAGGCT 420

ACGAGTTTGA GTCAGAAACA GATACAGAGA CCATCGCCAA GCTGATTAAA TATGTGTTCG 480

ACAACAGAGA AACTGAGGAC ATTACGTTTT CAACGTTGGT CGAGAGAGTC ATTCAGCAGT 540

TGGAAGGTGC ATTCGCGCTG GTTTTCAAGA GTGTCCACTA CCCAGGAGAA GCCGTTGCCA 600

CACGGAGAGG CAGCCCCCTG CTCATCGGAG TCCGGAGCAA ATACAAGCTC TCCACAGAAC 660

AGATCCCTAT CTTATACAGG ACGTGCACTC TGGAGAATGT GAAGAATATC TGTAAGACAC 720

GGATGAAGAG GCTGGACAGC TCCGCCTGCC TGCATGCTGT GGGCGACAAG GCCGTGGAAT 780

TCTTCTTTGC TTCTGATGCA AGCGCTATCA TAGAGCACAC CAACCGGGTC ATCTTCCTGG 840

AGGACGATGA CATCGCCGCA GTGGCTGATG GGAAACTCTC CATTCACCGG GTCAAGCGCT 900

```
CGGCCAGTGA TGACCCATCT CGAGCCATCC AGACCTTGCA GATGGAACTG CAGCAAATCA      960

TGAAAGGTAA CTTCAGTGCG TTTATGCAGA AGGAGATCTT CGAACAGCCA GAATCAGTTT     1020

TCAATACTAT GAGAGGTCGG GTGAATTTTG AAACCAACAC AGTGCTCCTG GGTGGCTTGA     1080

AGGACCACTT GAAGGAGATT CGACGATGCC GACGGCTCAT CGTGATTGGC TGTGGAACCA     1140

GCTACCACGC TGCCGTGGCT ACGCGGCAAG TTTTGGAGGA ACTGACTGAG CTTCCTGTGA     1200

TGGTTGAACT TGCTAGTGAT TTTCTGGACA GGAACACACC TGTGTTCAGG GATGACGTTT     1260

GCTTTTTCAT CAGCCAGTCA GGCGAGACCG CGGACACCCT CCTGGCGCTG CGCTACTGTA     1320

AGGACCGCGG CGCTCTCACC GTGGGCGTCA CCAACACCGT GGGCAGCTCC ATCTCTCGCG     1380

AGACCGACTG CGGCGTCCAC ATCAACGCAG GGCCGGAGAT CGGCGTGGCC AGCACCAAGG     1440

CTTATACCAG TCAGTTCATC TCTCTGGTGA TGTTTGGTTT GATGATGTCT GAAGACCGAA     1500

TTTCACTACA AAACAGGAGG CAAGAGATCA TCCGTGGCTT GAGATCTTTA CCTGAGCTGA     1560

TCAAGGAAGT GCTGTCTCTG GAGGAGAAGA TCCACGACTT GGCCCTGGAG CTCTACACGC     1620

AGAGATCGCT GCTGGTGATG GGGCGGGGCT ACAACTATGC CACCTGCCTG GAAGGAGCCC     1680

TGAAAATTAA AGAGATAACC TACATGCACT CAGAAGGCAT CCTGGCTGGG GAGCTGAAGC     1740

ACGGGCCCCT GGCACTGATT GACAAGCAGA TGCCCGTCAT CATGGTCATT ATGAAG        1796
```

(2) INFORMATION FOR SEQ ID NO:18:

(i) SEQUENCE CHARACTERISTICS:
        (A) LENGTH: 486 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

```
Met Cys Gly Ile Phe Ala Tyr Met Asn Tyr Arg Val Pro Arg Thr Arg
 1               5                  10                  15

Lys Glu Ile Phe Glu Thr Leu Ile Lys Gly Leu Gln Arg Leu Glu Tyr
                20                  25                  30

Arg Gly Tyr Asp Ser Ala Gly Val Ala Ile Asp Gly Asn Asn His Glu
            35                  40                  45

Val Lys Glu Arg His Ile Gln Leu Val Lys Lys Arg Gly Lys Val Lys
    50                  55                  60

Ala Leu Asp Glu Glu Leu Tyr Lys Gln Asp Ser Met Asp Leu Lys Val
65                  70                  75                  80

Glu Phe Glu Thr His Phe Gly Ile Ala His Thr Arg Trp Ala Thr His
                85                  90                  95

Gly Val Pro Ser Ala Val Asn Ser His Pro Gln Arg Ser Asp Lys Gly
            100                 105                 110

Asn Glu Phe Val Val Ile His Asn Gly Ile Ile Thr Asn Tyr Lys Asp
            115                 120                 125

Leu Arg Lys Phe Leu Glu Ser Lys Gly Tyr Glu Phe Glu Ser Glu Thr
        130                 135                 140

Asp Thr Glu Thr Ile Ala Lys Leu Ile Lys Tyr Val Phe Asp Asn Arg
145                 150                 155                 160

Glu Thr Glu Asp Ile Thr Phe Ser Thr Leu Val Glu Arg Val Ile Gln
                165                 170                 175

Gln Leu Glu Gly Ala Phe Ala Leu Val Phe Lys Ser Val His Tyr Pro
            180                 185                 190
```

```
Gly Glu Ala Val Ala Thr Arg Arg Gly Ser Pro Leu Leu Ile Gly Val
        195                 200                 205

Arg Ser Lys Tyr Lys Leu Ser Thr Glu Gln Ile Pro Ile Leu Tyr Arg
    210                 215                 220

Thr Cys Thr Leu Glu Asn Val Lys Asn Ile Cys Lys Thr Arg Met Lys
225                 230                 235                 240

Arg Leu Asp Ser Ser Ala Cys Leu His Ala Val Gly Asp Lys Val Val
                245                 250                 255

Glu Phe Phe Phe Ala Ser Asp Ala Ser Ala Ile Ile Glu His Thr Asn
            260                 265                 270

Arg Val Ile Phe Leu Glu Asp Asp Ile Ala Ala Val Ala Ala Asp Gly
        275                 280                 285

Lys Leu Ser Ile His Arg Val Lys Arg Ser Ala Ser Asp Asp Pro Ser
        290                 295                 300

Arg Ala Ile Gln Thr Leu Gln Met Glu Leu Gln Gln Ile Met Lys Gly
305                 310                 315                 320

Asn Phe Ser Ala Phe Met Gln Lys Glu Ile Phe Glu Gln Pro Glu Ser
                325                 330                 335

Val Phe Asn Thr Met Arg Gly Arg Val Asn Phe Glu Thr Asn Thr Val
            340                 345                 350

Leu Leu Gly Gly Leu Lys Asp His Leu Lys Glu Ile Arg Arg Cys Arg
        355                 360                 365

Arg Leu Ile Val Ile Gly Cys Gly Thr Ser Tyr His Ala Ala Val Ala
    370                 375                 380

Thr Arg Gln Val Leu Glu Glu Leu Thr Glu Leu Pro Val Met Val Glu
385                 390                 395                 400

Leu Ala Ser Asp Phe Leu Asp Arg Asn Thr Pro Val Phe Arg Asp Asp
                405                 410                 415

Val Cys Phe Phe Ile Ser Gln Ser Gly Lys Gly His Arg His Cys Gly
            420                 425                 430

Gln Pro Cys Ile Arg Ser Ala Leu Gly Ser Leu Leu Phe Ser Phe Ile
        435                 440                 445

Gln Leu Ser Pro Leu His Gly Tyr Pro Val Leu Arg Thr Leu Ser Cys
    450                 455                 460

Ser Gly His Leu Thr Arg Arg Ala Met Asp Tyr Cys Arg His Cys Thr
465                 470                 475                 480

Gly Arg Ala Arg Asp Val
                485
```

( 2 ) INFORMATION FOR SEQ ID NO:19:

( i ) SEQUENCE CHARACTERISTICS:
        ( A ) LENGTH: 1458 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:19:

```
ATGTGCGGAA TCTTTGCCTA CATGAACTAC AGAGTCCCCC GGACGAGGAA GGAGATCTTC      60

GAAACCCTCA TCAAGGGCCT GCAGCGGCTG GAGTACAGAG CTACGACTC  GGCAGGTGTG     120

GCGATCGATG GAATAATCA  CGAAGTCAAA GAAAGACACA TTCAGCTGGT CAAGAAAAGG     180

GGGAAAGTCA AGGCTCTCGA TGAAGAACTT TACAAACAAG ACAGCATGGA CTTAAAAGTG     240

GAGTTTGAGA CACACTTCGG CATTGCCCAC ACGCGCTGGG CCACCCACGG GGTCCCCAGT     300
```

-continued

| | | | | | | |
|---|---|---|---|---|---|---|
| GCTGTCAACA | GCCACCCTCA | GCGCTCAGAC | AAAGGCAACG | AATTTGTTGT | CATCCACAAT | 360 |
| GGGATCATCA | CAAATTACAA | AGATCTGAGG | AAATTTCTGG | AAAGCAAAGG | CTACGAGTTT | 420 |
| GAGTCAGAAA | CAGATACAGA | GACCATCGCC | AAGCTGATTA | AATATGTGTT | CGACAACAGA | 480 |
| GAAACTGAGG | ACATTACGTT | TTCAACGTTG | GTCGAGAGAG | TCATTCAGCA | GTTGGAAGGT | 540 |
| GCATTCGCGC | TGGTTTTCAA | GAGTGTCCAC | TACCCAGGAG | AAGCCGTTGC | CACACGGAGA | 600 |
| GGCAGCCCCC | TGCTCATCGG | AGTCCGGAGC | AAATACAAGC | TCTCCACAGA | ACAGATCCCT | 660 |
| ATCTTATACA | GGACGTGCAC | TCTGGAGAAT | GTGAAGAATA | TCTGTAAGAC | ACGGATGAAG | 720 |
| AGGCTGGACA | GCTCCGCCTG | CCTGCATGCT | GTGGGCGACA | AGGTCGTGGA | ATTCTTCTTT | 780 |
| GCTTCTGATG | CAAGCGCTAT | CATAGAGCAC | ACCAACCGGG | TCATCTTCCT | GGAGGACGAT | 840 |
| GACATCGCCG | CAGTGGCTGA | TGGGAAACTC | TCCATTCACC | GGGTCAAGCG | CTCGGCCAGT | 900 |
| GATGACCCAT | CTCGAGCCAT | CCAGACCTTG | CAGATGGAAC | TGCAGCAAAT | CATGAAGGT | 960 |
| AACTTCAGTG | CGTTTATGCA | GAAGGAGATC | TTCGAACAGC | CAGAATCAGT | TTTCAATACT | 1020 |
| ATGAGAGGTC | GGGTGAATTT | TGAAACCAAC | ACAGTGCTCC | TGGGTGGCTT | GAAGGACCAC | 1080 |
| TTGAAGGAGA | TTCGACGATG | CCGACGGCTC | ATCGTGATTG | GCTGTGGAAC | CAGCTACCAC | 1140 |
| GCTGCCGTGG | CTACGCGGCA | AGTTTTGGAG | GAACTGACTG | AGCTTCCTGT | GATGGTTGAA | 1200 |
| CTTGCTAGTG | ATTTTCTGGA | CAGGAACACA | CCTGTGTTCA | GGGATGACGT | TTGCTTTTTC | 1260 |
| ATCAGCCAGT | CAGGTAAGGG | ACACAGGCAT | TGTGGCCAGC | CTTGCATCAG | GTCAGCTCTG | 1320 |
| GGCTCTCTCC | TCTTCTCCTT | CATTCAGTTA | AGTCCTCTGC | ATGGCTACCC | TGTGCTGCGA | 1380 |
| ACCCTCTCTT | GCAGCGGTCA | TTTAACCCGT | AGAGCCATGG | ATTACTGTCG | CCATTGTACG | 1440 |
| GGGAGGGCAA | GAGATGTC | | | | | 1458 |

( 2 ) INFORMATION FOR SEQ ID NO:20:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:20:

| | | | |
|---|---|---|---|
| GATATCACGA | TGTGCGGAAT | CTTTGCCTAC | AT | 32 |

( 2 ) INFORMATION FOR SEQ ID NO:21:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "SYNTHETIC DNA"

( x i ) SEQUENCE DESCRIPTION: SEQ ID NO:21:

| | | |
|---|---|---|
| GTCGACTTCT | GGGGAAGTCA | AACCTGGCGG G | 31 |

( 2 ) INFORMATION FOR SEQ ID NO:22:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear (  i  i  ) MOLECULE TYPE: other nucleic acid
            ( A ) DESCRIPTION: /desc = "SYNTHETIC DNA"

( x i ) SEQUENCE DESCRIPTION: SEQ ID NO:22:

GCCATATGTG CGGAATCTTT GC                                                                        22

( 2 ) INFORMATION FOR SEQ ID NO:23:

(  i  ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear (  i  i  ) MOLECULE TYPE: other nucleic acid
            ( A ) DESCRIPTION: /desc = "SYNTHETIC DNA"

( x i ) SEQUENCE DESCRIPTION: SEQ ID NO:23:

GCGTCGACAA CCTGGCGGGC CG                                                                        22

( 2 ) INFORMATION FOR SEQ ID NO:24:

(  i  ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear (  i  i  ) MOLECULE TYPE: other nucleic acid
            ( A ) DESCRIPTION: /desc = "SYNTHETIC DNA"

( x i ) SEQUENCE DESCRIPTION: SEQ ID NO:24:

GCCATATGTG CGGAATCTTT GC                                                                        22

( 2 ) INFORMATION FOR SEQ ID NO:25:

(  i  ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear (  i  i  ) MOLECULE TYPE: other nucleic acid
            ( A ) DESCRIPTION: /desc = "SYNTHETIC DNA"

( x i ) SEQUENCE DESCRIPTION: SEQ ID NO:25:

GCGTCGACTT CCACAGTTAC AG                                                                        22